United States Patent [19]

Matsuo et al.

[11] Patent Number: 5,164,400

[45] Date of Patent: Nov. 17, 1992

[54] PYRROLOQUINOLINE COMPOUNDS

[75] Inventors: Masaaki Matsuo, Osaka; Takashi Manabe, Kawanishi; Hiroyuki Okumura, Toyono; Hiroshi Matsuda; Naoaki Fujii, both of Osaka, all of Japan

[73] Assignee: Fujisawa Pharmaceutical Co., Ltd., Osaka, Japan

[21] Appl. No.: 552,127

[22] Filed: Jul. 13, 1990

[30] Foreign Application Priority Data

Aug. 22, 1989 [GB] United Kingdom ............. 8919091
Feb. 13, 1990 [GB] United Kingdom ............. 9003252

[51] Int. Cl.$^5$ .............. A61K 31/535; A61K 31/54; A61K 31/435; C07D 498/02; C07D 513/00; C07D 455/08

[52] U.S. Cl. .............. 514/296; 514/224.5; 514/230.2; 544/32; 544/69; 544/101; 546/14; 546/96

[58] Field of Search ............. 544/32, 101, 69; 546/94, 14; 514/224.5, 230.2, 296

[56] References Cited

U.S. PATENT DOCUMENTS 4,739,073 4/1988 Kathawala et al. ............. 548/406

OTHER PUBLICATIONS

J. of Medicinal Chemistry, 1973, vol. 16, No. 3, 251.

*Primary Examiner*—Cecilia Tsang
*Attorney, Agent, or Firm*—Oblon, Spivak, McClelland, Maier & Neustadt

[57] ABSTRACT

The invention relates to a compound of the formula:

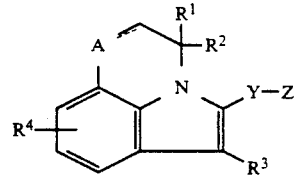

in which $R^1$ and $R^2$ are each hydrogen or lower alkyl, $R^3$ is aryl or unsaturated, 5- or 6-membered heterocyclic group containing a sulfur atom, each of which may be substituted by one or more substituent(s) selected from the group consisting of halogen, hydroxy, lower alkyl, aryloxy, trihalo(lower)alkyl, lower alkoxy and mono- or di(lower)alkylamino, $R^4$ is hydrogen, halogen or lower alkyl, A is methylene, methine, oxa, thia, sulfinyl or sulfonyl, Y is vinylene or ethylene.

Z is a group of the formula:

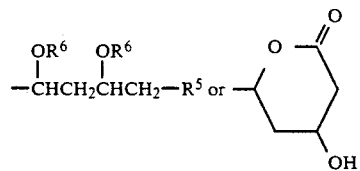

wherein $R^5$ is carboxy or protected carboxy, and $R^6$ is hydrogen or hydroxy-protective group, and the line of ⸺ is a single or double bond, or a pharmaceutically acceptable salt thereof, useful as a 3-hydroxy-3-methylglutaryl-coenzyme A reductase inhibitor.

14 Claims, No Drawings

PYRROLOQUINOLINE COMPOUNDS

This invention relates to novel pyrroloquinoline compounds and pharmaceutically acceptable salts thereof.

More particularly, it relates to novel pyrroloquinoline compounds and pharmaceutically acceptable salts thereof, which have inhibitory activity against the enzyme 3-hydroxy-3-methylglutaryl-coenzyme A reductase (HMG-CoA reductase), to a process for preparation thereof, to a pharmaceutical composition containing the same, to a use of the same as a medicament, and to a method for treating hypercholesterolaemic and hyperlipoproteinaemic states and associated conditions.

Accordingly, one object of the present invention is to provide pyrroloquinoline compounds and pharmaceutically acceptable salts thereof, which function as antihypercholesterolemic or antihyperproteinamic agents by limiting biosynthesis via inhibiting the activity of HMG-CoA reductase and therefore are capable of lowering blood serum cholesterol levels and blood lipid levels.

Another object of the present invention is to provide a process for preparation of pyrroloquinoline compounds and pharmaceutically acceptable salts thereof.

Another object of the present invention is to provide a pharmaceutical composition comprising, as an active ingredient, said pyrroloquinoline compounds and pharmaceutically acceptable salts thereof.

Still further object of the present invention is to provide a use of said pyrroloquinoline compounds and pharmaceutically acceptable salts thereof as a medicament and a method for treating hypercholesterolemic states, hyperlipoproteinemic states and associated conditions in human being or animal.

High levels of blood cholesterol and blood lipids are conditions which are involved in the onset of arteriosclerosis. It is well known that inhibitors of HMG-CoA reductase are effective in lowering the level of blood plasma cholesterol, especially low density lipoprotein cholesterol (LDL-C). It has now been established that lowering LDL-C levels affords protection from coronary heart disease, cerebral infarction, and the like.

The pyrroloquinoline compounds of this invention inhibit HMG-CoA reductase and so inhibit cholesterol biosynthesis. They lower concentrations of chlesterol in blood. Thus they are useful for treating hypercholesterolemic and hyperlipoproteinemic states (e.g. atherosclerosis), associated conditions (e.g. angina, myocardial infarction, cerebral vascular occlusion, arterial aneurism, peripheral vascular disease, recurrent pancreatitis and xanthomas), diabetic nephropathy, and the like.

The object pyrroloquinoline compounds of this invention are novel and can be represented by the following general formula:

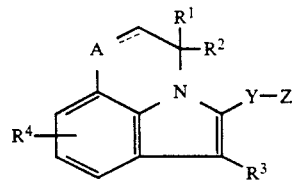

in which
$R^1$ and $R^2$ are each hydrogen or lower alkyl,
$R^3$ is aryl or heterocyclic group, each of which may be substituted by suitable substituent(s),
$R^4$ is hydrogen, halogen or lower alkyl,
A is methylene, methine, oxa, thia, sulfinyl or sulfonyl,
Y is vinylene or ethylene,
Z is a group of the formula:

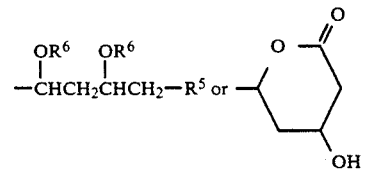

wherein
$R^5$ is carboxy or protected carboxy, and
$R^6$ is hydrogen or hydroxy-protective group, and the line of ⸺ is a single or double bond, or pharmaceutically acceptable salts thereof.

Suitable pharmaceutically acceptable salts of the object compound (I) are conventional non-toxic salts and may include a salt with a base such as an inorganic base salt, for example, an alkali metal salt (e.g. sodium salt, potassium salt, etc.), an alkaline earth metal salt (e.g. calcium salt, magnesium salt, etc.), an ammonium salt, an organic base salt, for example, an organic amine salt (e.g. triethylamine salt, pyridine salt, picoline salt, ethanolamine salt, triethanolamine salt, dicyclohexylamine salt, N,N'-dibenzylethylenediamine salt, etc.); a salt with a basic amino acid (e.g. arginine, etc.); a salt with an acid such as an inorganic acid addition salt (e.g. hydrochloride, hydrobromide, sulfate, phosphate, etc.), an organic acid addition salt (e.g. formate, acetate, trifluoroacetate, maleate, tartrate, methanesulfonate, benzenesulfonate, etc.); a salt with an acidic amino acid (e.g. aspartic acid, glutamic acid, etc.); and the like.

In the object compound (I) and the intermediary compounds mentioned below, it is to be understood that there may be one or more stereo-isomeric pair(s) such as optical and/or geometrical isomers due to asymmetric carbon atom(s) and/or double bond(s), and such isomers are also included within the scope of the present invention.

According to the present invention, the object compound (I) or pharmaceutically acceptable salts thereof can be prepared by the processes as illustrated by the following reaction schemes.

Process 1:

-continued

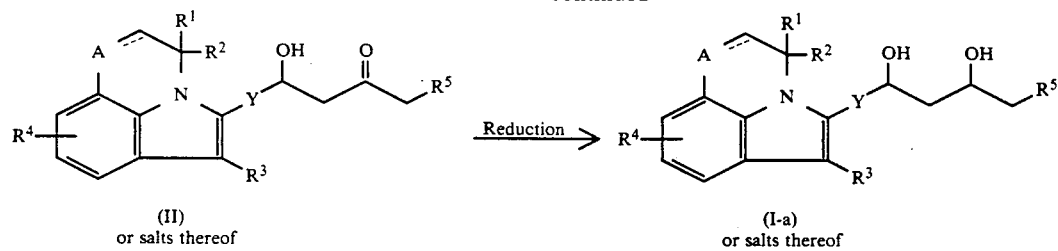

(II) or salts thereof

Reduction →

(I-a) or salts thereof

Process 2:

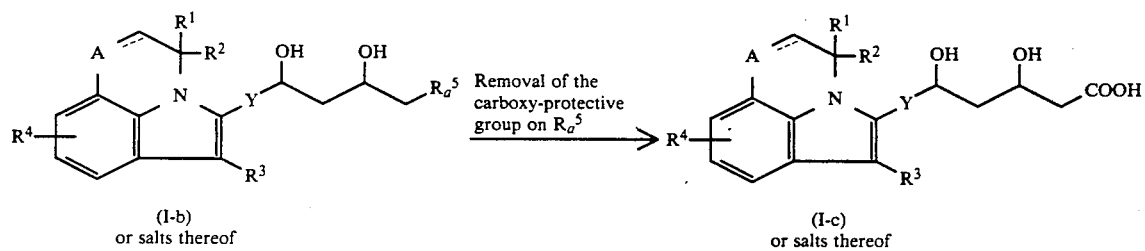

(I-b) or salts thereof

Removal of the carboxy-protective group on $R_a^5$ →

(I-c) or salts thereof

Process 3:

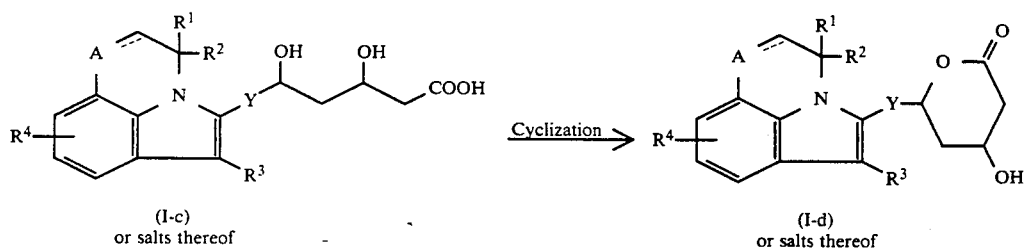

(I-c) or salts thereof

Cyclization →

(I-d) or salts thereof

Process 4:

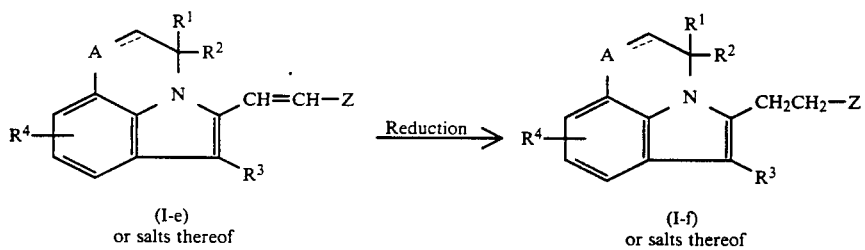

(I-e) or salts thereof

Reduction →

(I-f) or salts thereof

Process 5:

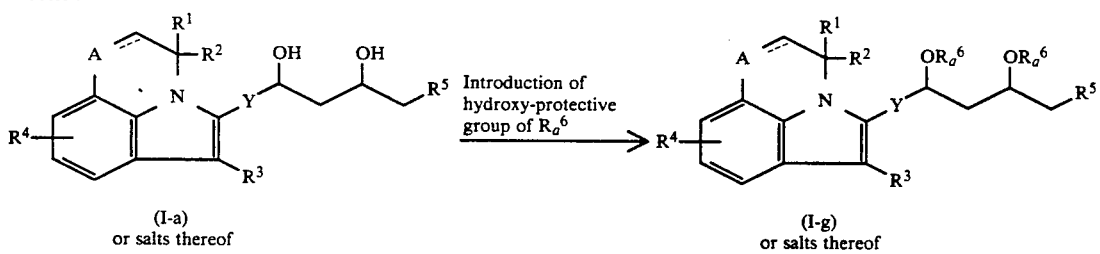

(I-a) or salts thereof

Introduction of hydroxy-protective group of $R_a^6$ →

(I-g) or salts thereof

Process 6:

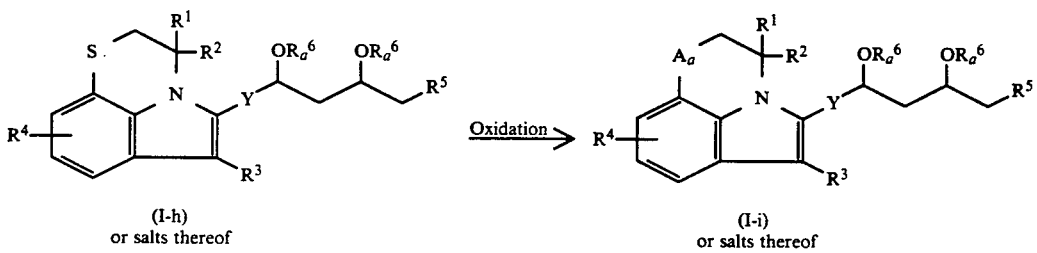

(I-h) or salts thereof

Oxidation →

(I-i) or salts thereof

Process 7:

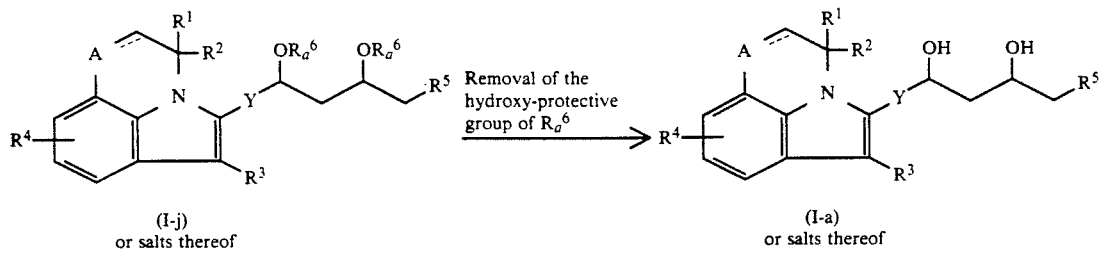

(I-j) or salts thereof → Removal of the hydroxy-protective group of $R_a^6$ → (I-a) or salts thereof Process 8:

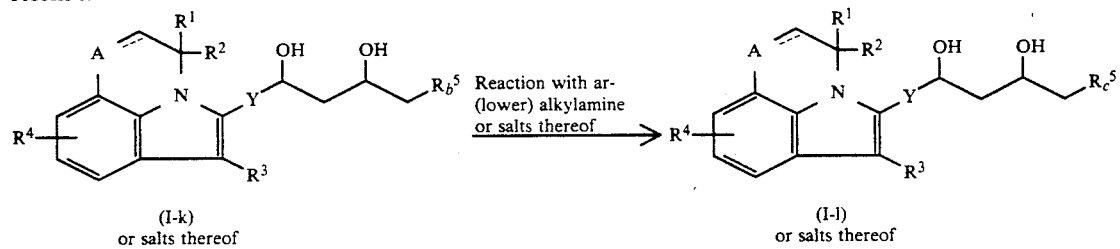

(I-k) or salts thereof → Reaction with ar-(lower) alkylamine or salts thereof → (I-l) or salts thereof Process 9:

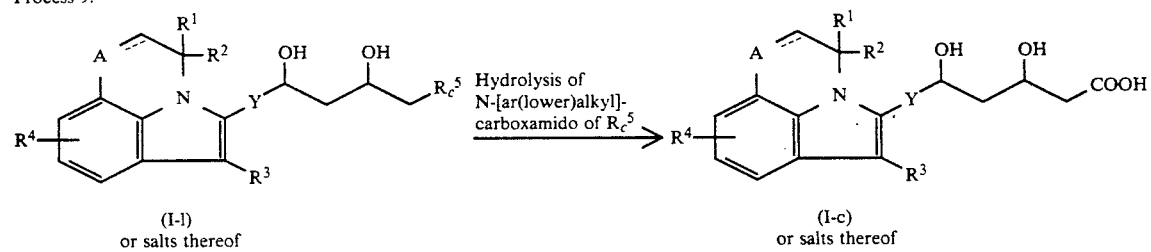

(I-l) or salts thereof → Hydrolysis of N-[ar(lower)alkyl]-carboxamido of $R_c^5$ → (I-c) or salts thereof in which $R^1$, $R^2$, $R^3$, $R^4$, $R^5$, A, Y, Z and the line of ---- are each as defined above.

$R_a^5$ is protected carboxy,
$R_b^5$ is esterified carboxy,
$R_c^5$ is N-[ar(lower)alkyl]carboxamido,
$R_a^6$ is hydroxy-protective group, and
$A_a$ is sulfinyl or sulfonyl.

The compound (II) used in the Process 1 is new and can be prepared, for example, by the following methods or a conventional manner.

Method A:

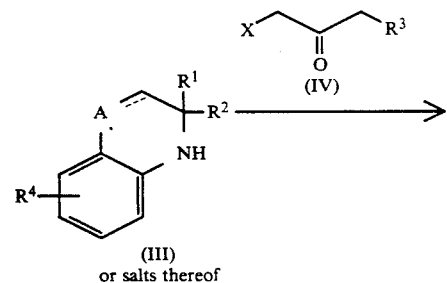

(III) or salts thereof

Method B:

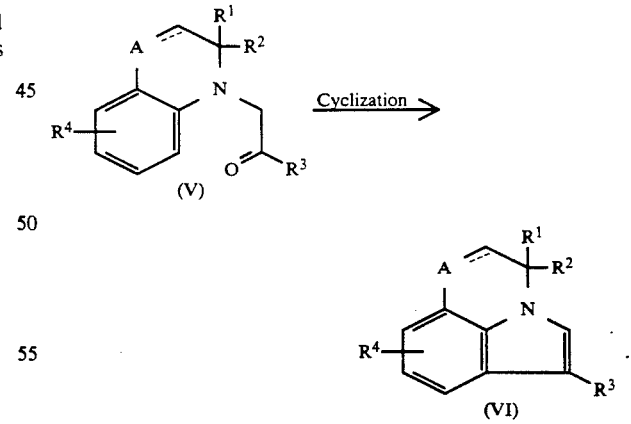

(V) → Cyclization → (VI)

Method C:

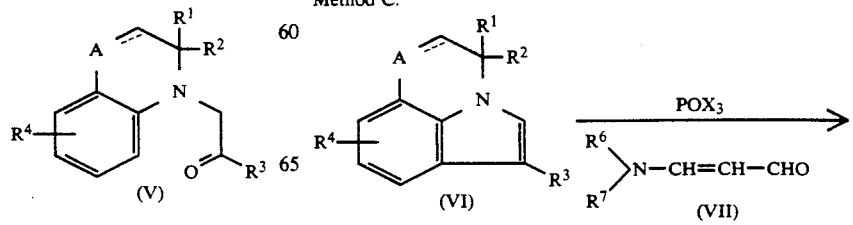

(VI) + $R^6R^7$N—CH=CH—CHO (VII) → POX₃ →

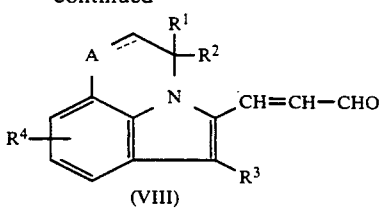

(VIII)

Method D:

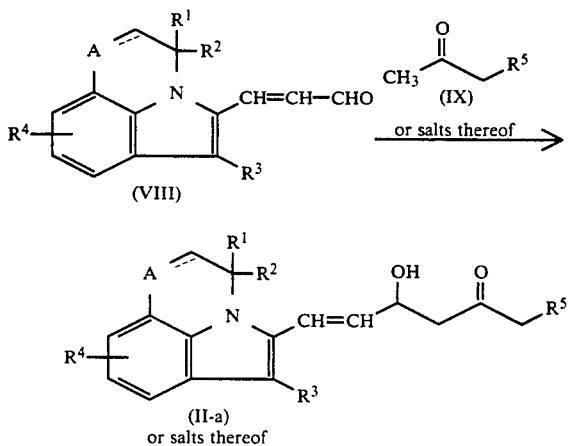

in which
R$^1$, R$^2$, R$^3$, R$^4$, R$^5$, A and the line of are each as defined above.
R$^6$ and R$^7$ are each lower alkyl, and
X is halogen.

In the above and subsequent descriptions of the present specification, suitable examples and illustrations of the various definitions which the present invention includes within the scope thereof are explained in detail as follows.

The term "lower" is intended to mean 1 to 6 carbon atom(s), unless otherwise indicated.

Suitable "lower alkyl" may include straight or branched one such as methyl, ethyl, propyl, isopropyl, butyl, t-butyl, pentyl, hexyl, and the like, in which more preferable example may be C$_1$–C$_4$ alkyl and the most preferable one may be methyl.

Suitable "aryl" may include phenyl, tolyl, xylyl, cumenyl, mesityl, naphthyl and the like, in which more preferable example may be phenyl and naphthyl, wherein said aryl may be substituted by one or more, preferably one to three suitable substituent(s) such as:
halogen as mentioned below (e.g. chlorine, fluorine, etc.);
hydroxy;
lower alkyl as mentioned above (e.g. methyl, t-butyl, etc.);
aryloxy wherein aryl moiety is as mentioned above (e.g. phenoxy, etc.);
trihalo(lower)alkyl as mentioned below (e.g. trifluoromethyl, etc.);
lower alkoxy as mentioned below (e.g. metoxy, etc.);
mono- or di(lower)alkylamino such as mentioned below (e.g. dimethylamino, etc.); and the like.

Preferable example of "aryl, which may be substituted by suitable substituent(s)" thus defined may be phenyl or naphthyl, each of which may be substituted by one to three suitable substituent(s) selected from a group consisting of halogen, hydroxy, C$_1$–C$_4$ alkyl, phenoxy, trihalo(C$_1$–C$_4$)alkyl, C$_1$–C$_4$ alkoxy and di(C$_1$–C$_4$)alkylamino, and the more preferable may be:
phenyl;
mono- or di- or trihalophenyl [e.g. 2-(or 3- or 4-)-fluorophenyl, 2,4-(or 3, 4-)difluorophenyl, 4-chlorophenyl, 3,4-dichlorophenyl, 2-chloro-4-fluorophenyl, 2,4,6-trifluorophenyl, etc.);
mono- or di(C$_1$–C$_4$)alkylphenyl [e.g. m-tolyl, 2,4-(or 3,4- or or 3,5-)xylyl, etc.];
[mono- or di(C$_1$–C$_4$)alkyl](halo)phenyl [e.g. 4-fluoro-2- (or 3-methylphenyl, 4-fluoro-3,5-dimethylphenyl, etc.];
phenoxyphenyl (e.g. 4-phenoxyphenyl, etc.);
naphthyl (e.g. 2-naphtyl, etc.);
trihalo(C$_1$–C$_4$)alkylphenyl (e.g. 3-trifluoromethylphenyl, etc.);
[di{C$_1$–C$_4$)alkylamino]phenyl (e.g. 4-dimethylaminophenyl, etc.);
[mono- or di(C$_1$–C$_4$)alkyl](hydroxy)phenyl (e.g. 3,5-di-t-butyl-4-hydroxyphenyl, etc.);
[(C$_1$–C$_4$)alkoxy](halo)phenyl (e.g. 2-methoxy-4-fluorophenyl, etc.).

Suitable heterocyclic group moiety of "heterocyclic group, which may be substituted by suitable substituent(s)", may include unsaturated monocyclic or polycyclic heterocyclic group containing at least one hetero-atom such as oxygen, sulfur or nitrogen atom.

Preferable unsaturated heterocyclic group may be unsaturated 3 to 8-membered, more preferably 5 or 6-membered heterocyclic group containing a sulfur atom, for example, thienyl, etc.; and the like, wherein said heterocyclic group may be substituted by one or more, preferably one to three suitable substituents(s) such as those mentioned in the explanation of "aryl, which may be substituted by suitable substituent(s)".

Preferable example of "heterocyclic group, which may be substituted by suitable substituent(s)" thus defined may be thienyl, which may be substituted by one or two suitable substituent(s) selected from a group consisting of C$_1$–C$_4$ alkyl and halogen, wherein more preferable example may be thienyl, C$_1$–C$_4$ alkylthienyl and halothienyl, and the most preferable one may be 5-methyl-2-thienyl and 5-chloro-2-thienyl.

Suitable "protected carboxy" may include esterified carboxy and amidated carboxy, wherein "esterified carboxy" and "amidated carboxy" can be referred to the ones as mentioned below.

Suitable "protected carboxy" may include esterified carboxy and amidated carboxy, wherein "esterified carboxy" and "amidated carboxy" can be referred to the ones as mentioned below.

Suitable examples of the ester moiety of an esterified carboxy may be the ones such as lower alkyl ester (e.g. methyl ester, ethyl ester, propyl ester, isopropyl ester, butyl ester, isobutyl ester, t-butyl ester, pentyl ester, hexyl ester, etc.) which may have at least one suitable substituent(s), for example, lower alkanoyloxy(lower)alkyl ester [e.g. acetoxymethyl ester, propionyloxymethyl ester, butyryloxymethyl ester, valeryloxymethyl ester, pivaloyloxymethyl ester, hexanoyloxymethyl ester, 1-(or 2-)acetoxyethyl ester, 1-(or 2- or 3-)acetoxypropyl ester, 1-(or 2- or 3- or 4-)acetoxybutyl ester, 1-(or 2-)propionyloxyethyl ester, 1-(or 2- or 3-)propionyloxypropyl ester, 1-(or 2-)butyryloxyethyl ester, 1-(or 2-)isobutyryloxyethyl ester, 1-(or 2-)pyvaloyloxyethyl ester, 1-(or 2-)hexanoyloxyethyl ester, isobutyryloxymethyl ester, 2-ethylbutyryloxymethyl ester, 3,3-dimethylbutyryloxymethyl ester, 1-(or 2-)pentanoyloxyethyl ester, etc.], lower alkanesulfonyl(lower)alkyl ester (e.g. 2-mesylethyl ester, etc.), mono(or di or tri)halo(lower)alkyl ester (e.g. 2-iodoethyl ester, 2,2,2-trichloroethyl ester, etc.); lower alkoxycarbonyloxy(lower)alkyl ester [e.g. methoxycarbonyloxymethyl ester, ethoxycarbonyloxymethyl ester, propoxycarbonyloxymethyl ester, t-butoxycarbonyloxymethyl ester, 1-(or 2-)methoxycarbonyloxyethyl ester, 1-(or 2-)ethoxycarbonyloxyethyl ester, 1-(or 2-) isopropoxycarbonyloxyethyl ester, etc.], phthalidylidene(lower)alkyl ester, or (5-lower alkyl-2-oxy-1,3-dioxol-4-yl)(lower)alkyl ester [e.g. (5-methyl-2-oxo-1,3-dioxol-4-yl)methyl ester, (5-ethyl-2-oxo-1,3-dioxol-4-yl)methyl ester, (5-propyl-2-oxo-1,3-dioxol-4-yl)ethyl ester, etc.]; lower alkenyl ester (e.g. vinyl ester, allyl ester, etc.); lower alkynyl ester (e.g. ethynyl ester, propnyl ester, etc.); ar(lower)alkyl ester which may have at least one suitable substituent(s) (e.g. benzyl ester, 4-methoxybenzyl ester, 4-nitrobenzyl ester, phenethyl ester, trityl ester, benzhydryl ester, bis(methoxyphenyl)methyl ester, 3,4-dimethoxybenzyl ester, 4-hydroxy-3,5-di-t-butylbenzyl ester, etc.); aryl ester which may have at least one suitable substituent(s) (e.g. phenyl ester, 4-chlorophenyl ester, tolyl ester, t-butylphenyl ester, xylyl ester, mesityl ester, cumenyl ester, etc.); phthalidyl ester; and the like.

More preferable example of the esterified carboxy thus defined may be $C_1$-$C_4$ alkoxycarbonyl and the most preferable one may be methoxycarbonyl.

Suitable examples of the amidated carboxy may include N-[ar(lower)alkyl]carboxamido as mentioned below, in which more preferable example may be N-[phenyl($C_1$-$C_4$)alkyl]carboxamido and the most preferable one may be N-(1-phenylethyl)carboxamido.

Suitable "halogen" may include chlorine, bromine, iodine and fluorine, in which more preferable example may be chlorine and fluorine for $R^4$, and bromine for X.

Suitable "trihalo(lower)alkyl" may include straight or branched one such as trifluoromethyl, trifluorethyl, trichloromethyl, trichlorethyl, and the like, in which more preferable example may be trihalo($C_1$-$C_4$)alkyl and the most preferable one may be trifluoromethyl.

Suitable "lower alkoxy" may include straight or branched one such as methoxy, ethoxy, propoxy, isopropoxy, butoxy, t-butoxy, pentyloxy, hexyloxy and the like, in which more preferable example may be $C_1$-$C_4$ alkoxy and the most preferable one may be methoxy.

Suitable "mono- or di(lower)alkylamino" means straight or branched one such as methylamino, dimethylamino, ethylamino, diethylamino, N-methyl-N-ethylamino, propylamino, dipropylamino, isopropylamino, butylamino, pentylamino, hexylamino, and the like. More preferable example of mono- or di(lower)alkylamino thus defined may be di($C_1$-$C_4$)alkylamino and the most preferable one may be dimethylamino.

Suitable "hydroxy-protective group" may include trisubstituted silyl group such as a silyl group substituted by a group consisting of lower alkyl, aryl and ar(lower)alkyl (e.g. trimethylsilyl, triethylsilyl, isopropyldimethylsilyl, t-butyldimethylsilyl, diisopropylmethylsilyl, triphenylsilyl, tribenzylsilyl, t-butyldiphenylsilyl, etc.); acyl group such as carbamoyl, aliphatic acyl, aromatic acyl, heterocyclic acyl and aliphatic acyl substituted with aromatic or heterocyclic group(s) derived from carboxylic, carbonic, sulfonic and carbamic acids; and the like, in which more preferable example may be [($C_1$-$C_4$)alkyl]diphenylsilyl and the most preferable one may be t-buty diphenylsilyl.

Suitable "ar(lower)alkyl" moiety of "N-[ar(lower)alkyl]carboxamide" and "ar(lower)alkylamine" may be straight or branched lower alkyl substituted by aryl (e.g. phenyl, tolyl, xylyl, cumenyl, mesilyl, naphthyl, etc.) such as phenylmethyl, phenylethyl, phenylpropyl, 1-methyl-2-phenylethyl, phenylbutyl, phenylpentyl, phenylhexyl, and the like, in which more preferable example may be phenyl($C_1$-$C_4$)alkyl and the most preferable one may be 1-phenylethyl.

The processes for the preparation of the object compound {I} of the present invention are explained in detail in the following.

(1) Process 1:

The compound (I-a) or salts thereof can be prepared by reducing the compound (II) or salts thereof.

Suitable salts of the compounds (I-a) and (II) may be the same as those for the compound (I).

The reduction method applicable for this removal reaction may include, for example, reduction by using a combination of a metal (e.g. zinc, zinc amalgam, etc.) or a salt of chrome compound (e.g. chromous chloride, chromous acetate, etc.) and an organic or inorganic acid (e.g. acetic acid, propionic acid, hydrochloric acid, sulfuric acid, etc.); and conventional catalytic reduction in the presence of a conventional metallic catalyst such as palladium catalysts (e.g. spongy palladium, palladium black, palladium oxide, palladium on carbon, colloidal palladium, palladium on barium sulfate, palladium on barium carbonate, palladium hydroxide on carbon, etc.), nickel catalysts [e.g. reduced nickel, nickel oxide, Raney nickel, etc.), platinum catalysts (e.g. platinum plate, spongy platinum, platinum black, colloidal platinum, platinum oxide, platinum wire, etc.), sodium borohydride a combination of tri(lower)alkylborane and sodium borohydride, and the like, in which more preferable method is a combination of tri(lower)alkylborane and sodium borohydride.

This reaction is usually carried out in a conventional solvent which does not adversely influence the reaction such as water, alcohol (e.g. methanol, ethanol, propanol, etc.), dioxane, tetrahydrofuran, acetic acid, buffer solution (e.g. phosphate buffer, acetate buffer, etc.), and the like, or a mixture thereof.

The reaction temperature is not critical and the reaction is usually carried out under from cooling to warming.

(2) Process 2:

The compound (I-c) or salts thereof can be prepared by subjecting the compound (I-b) or salts thereof to removal reaction of the carboxy-protective group on $R_a^5$.

Suitable salts of the compound (I-c) may be the same as those for the compound (I).

Suitable salts of the compound (I-b) may be salts with acids such as those given for the compound (I).

The present reaction is usually carried out by a conventional method such as hydrolysis, reduction, and the like.

(i) Hydrolysis:

Hydrolysis is preferably carried out in the presence of a base or an acid. Suitable base may include an alkali metal hydroxide (e.g. sodium hydroxide, potassium hydroxide, etc.), an alkaline earth metal hydroxide (e.g. magnesium hydroxide, calcium hydroxide, etc.), alkali metal hydride (e.g. sodium hydride, potassium hydride, etc.), alkaline earth metal hydride (e.g. calcium hydride, etc.), alkali metal alkoxide (e.g. sodium methoxide, sodium ethoxide, potassium t-butoxide, etc.), an alkali metal carbonate (e.g. sodium carbonate, potassium carbonate, etc.), and alkaline earth metal carbonate (e.g. magnesium carbonate, calcium carbonate, etc.), an alkali metal bicarbonate (e.g. sodium bicarbonate, potassium bicarbonate, etc.), and the like.

Suitable acid may include an organic acid (e.g. formic acid, acetic acid, propionic acid, trifluoroacetic acid, benzenesulfonic acid, p-toluenesulfonic acid, etc.) and an inorganic acid (e.g. hydrochloric acid, hydrobromic acid, sulfuric acid, phosphoric acid, etc.). The acidic hydrolysis using trifluoroacetic acid is usually accelerated by addition of cation trapping agent (e.g. phenol, anisole, etc.).

In case that the hydroxy-protective group is tri(-lower)alkylsilyl, the hydrolysis can be carried out in the presence of tri(lower)alkylammonium halide (e.g. tributylammonium fluoride, etc.).

This reaction is usually carried out in a conventional solvent which does not adversely influence the reaction such as water, dichloromethane, alcohol [e.g. methanol, ethanol, etc.), tetrahydrofuran, dioxane, acetone, etc.), or a mixture thereof. A liquid base or acid can be also used as the solvent.

The reaction temperature is not critical and the reaction is usually carried out under from cooling to heating.

(ii) Reduction

The reduction method applicable for this removal reaction may include, for example, reduction by using a combination of a metal (e.g. zinc, zinc amalgam, etc.) or a salt of chrome compound (e.g. chromous chloride, chromous acetate, etc.) and an organic or inorganic acid (e.g. acetic acid, propionic acid, hydrochloric acid, sulfuric acid, etc.); and conventional catalytic reduction in the presence of a conventional metallic catalyst such as palladium catalysts (e.g. spongy palladium, palladium black, palladium oxide, palladium on carbon, colloidal palladium, palladium on barium sulfate, palladium on barium carbonate, palladium hydroxide on carbon, etc.), nickel catalysts (e.g. reduced nickel, nickel oxide, Raney nickel, etc.), platinum catalysts (e.g. platinum plate, spongy platinum, platinum black, colloidal platinum, platinum oxide, platinum wire, etc.), and the like.

This reaction is usually carried out in a conventional solvent which does not adversely influence the reaction such as water, alcohol (e.g. methanol, ethanol, propanol, etc.), dioxane, tetrahydrofuran, acetic acid, buffer solution (e.g. phosphate buffer, acetate buffer, etc.), and the like, or a mixture thereof.

The reaction temperature is not critical and the reaction is usually carried out under from cooling to warming.

In case that the carboxy-protective group is allyl group, it can be deprotected by hydrogenolysis using a palladium compound.

Suitable palladium compound used in this reaction may be palladium on carbon, palladium hydroxide on carbon, palladium chloride, a palladium-ligand complex such as tetrakis(triphenylphosphine)palladium(0), bis(-dibezylideneacetone)palladium(0), di[1,2-bis(diphenyl phosphino)ethane]palladium(0), tetrakis(triphenyl phosphite)palladium(0), tetrakis(triethyl phosphite)palladium(0), and the like.

The reaction can preferably be carried out in the presence of a scavenger of allyl group generated in situ, such as amine (e.g. morpholine, N-methylaniline, etc.), an activated methylene compound (e.g. dimedone, benzoylacetate, 2-methyl-3-oxovaleric acid, etc.), a cyanohydrin compound (e.g. α-tetrahydropyranyloxybenzyl cyanide, etc.), lower alkanoic acid or a salt thereof (e.g. formic acid, acetic acid, ammonium formate, sodium acetate, etc.), N-hydroxysuccinimide, and the like.

This reaction can be carried out in the presence of a base such as lower alkylamine (e.g. butylamine, triethyamine, etc.), pyridine, and the like.

When palladium-ligand complex is used in this reaction, the reaction can preferably be carried out in the presence of the corresponding ligand (e.g. triphenylphosphine, triphenyl phosphite, triethyl phosphite, etc.).

This reaction is usually carried out in a conventional solvent which does not adversely influence the reaction such as water, methanol, ethanol, propanol, dioxane, tetrahydrofuran, acetonitrile, chloroform, dichloromethane, dichloroethane, ethyl acetate, etc., or a mixture thereof.

The removal reaction can be selected according to the kind of carboxy-protective group to be eliminated.

(3) Process 3:

The compound (I-d) or salts thereof can be prepared by cyclizing the compound (I-c) or salts thereof.

Suitable salts of the compound (I-d) may be the same as those for the compound (I-b).

This reaction is usually carried out by a conventional method such as heating, or by a reaction in the presence of a condensing agent, and the like.

Preferable condensing agent may be a conventional one such as carbodiimide compound or a salt thereof [e.g. N,N'-diethylcarbodiimide, N,N'-diisopropylcarbodiimide, N,N'-dicyclohexylcarbodiimide, N-cyclohexyl-N'-morpholinoethylcarbodiimide, N-cyclohexyl-N'-(4-diethyl-aminocyclohexyl)carbodiimide, N-ethyl-N'-(3-dimethylaminopropyl)carbodiimide or its hydrochloride, etc.]; N,N'-carbonyldiimidazole, N,N'-carbonylbis(2-methylimidazole); keteneimine compound (e.g. pentamethyleneketene-N-cyclohexylimine, diphenylketene-N-cyclohexylimine, etc.); ethoxyacetylene; 1-alkoxy-1-chloroethylene; ethyl polyphosphate; isopropylpolyphosphate; phosphorus oxychloride; phosphorus trichloride; thionyl chloride; oxalyl chloride; a combination of triphenylphosphine with carbon tetrachloride or diazenedicarboxylate; 2-ethyl-7-hydroxybenzisoxazolium salt; 2-ethyl-5-(m-sulfophenyl)-isoxazolium hydroxide intramolecular salt; 1-(p-chlorobenzenesulfonyloxy)-6-chloro-1H-benzotriazole; 1-hydroxybenzotriazole; so-called Vilsmeier reagent prepared by the reaction of N,N-dimethylformamide with thionyl chloride, phosgene, phosphorus oxychloride, etc.; and the like.

This reaction is usually carried out in a conventional solvent which does not adversely influence the reaction such as dichloromethane, methanol, ethanol, propanol, acetonitrile, pyridine, N,N-dimethylformamide, 4-methyl-2-pentanone, tetrahydrofuran, benzene, toluene, xylene, etc., or a mixture thereof.

The reaction temperature of this reaction is not critical and the reaction is usually carried out under from cooling to heating.

(4) Process 4:

The compound (I-f) or salts thereof can be prepared by reducing the compound (I-e) or salts thereof.

Suitable salts of the compounds (I-e) and (I-f) may be the same as those for the compound (I).

The method of reduction and the reaction conditions (e.g. reaction temperature, solvent, etc.) are substantially the same as those illustrated for the removal reaction of the carboxy-protective group of the compound (I-b) in Process 2, and therefore are to be referred to said explanation.

(5) Process 5:

The compound (I-g) or salts thereof can be prepared by introducing a hydroxy-protective group into the compound (1-a) or salts thereof.

Suitable salts of the compound (I-g) may be the same as those for the compound (I).

Suitable introducing agent of the hydroxy-protective group used in this reaction may be a conventional sylilating agent which is capable of introducing a trisubstituted silyl group as mentioned in the above explanation of "hydroxy-protective group" such as trisubstituted silyl halide (e.g. trisubstituted silyl chloride, etc.) acylating agent which is capable of introducing an acyl group as mentioned in the above explanation of "hydroxy-protective group" such as carboxylic acid, carbonic acid, sulfonic acid and their reactive derivative, for example, an acid halide, an acid anhydride, an activated amide, an activated ester, etc.; and the like.

(6) Process 6:

The compound (I-i) or salts thereof can be prepared by oxidizing the compound (I-h) or salts thereof.

Suitable salts of the compounds (I-h) and (I-i) may be the same as those for the compound (I).

Suitable oxidizing agent of the formyl group used in this reaction may be a conventional one which is capable of converting a thio group to a sulfinyl or sulfonyl group such as potassium permanganate, chromic compound (e.g. chromium trioxide, chromic acid, sodium chromate, dichromic acid, sodium dichromate, pyridinium dichromate, etc.) haloperbenzoic acid (e.g. m-chloroperbenzoic acid, etc.), and the like.

The reaction is usually carried out in a conventional solvent which does not adversely influence the reaction such as water, acetone, dioxane, dimethylformamide, dichloromethane, pyridine, etc., or a mixture thereof.

The reaction temperature is not critical and the reaction is usually carried out under from cooling to warming.

(7) Process 7:

The compound (I-a) or salts thereof can be prepared by subjecting the compound (I-j) or salts thereof to removal reaction of the hydroxy-protective group of $R_a^6$.

Suitable salts of the compound (I-j) may be the same as those for the compound (I).

This reaction is usually carried out by a conventional method such as hydrolysis, reduction, and the like.

The method of hydrolysis and reduction, and the reaction conditions (e.g. reaction temperature, solvent, etc.) are substantially the same as those illustrated for removal reaction of the carboxy-protective group of the compound (I-b) in Process 2, and therefore are to be referred to said explanation.

In case that the hydroxy-protective group is trisubsituted silyl, the removal of this protective group can also be carried out in the presence of tetra(lower)alkylammonium fluoride (e.g. tetrabutylammonium fluoride, etc.).

(8) Process 8:

The compound (I-l) or salts thereof can be prepared by reacting the compound (I-k) or salts thereof with ar(lower)alkylamine or salts thereof.

Suitable salts of the compounds (I-k) and (I-l) may be the same as those for the compound (I-b).

Suitable salts of ar(lower)alkylamine may be the same as those for the compound (I-b).

This reaction is usually carried out by heating the compound (I-k) and ar(lower)alkylamine in or without a conventional solvent which does not adversely influence the reaction such as water, alcohol (e.g. methanol, ethanol, propanol, etc.), dioxane, tetrahydrofuran, benzene, toluene, xylene, and the like, or a mixture thereof.

The reaction temperature is not critical and the reaction is usually carried out under from warming to heating.

In case that the optically active phenyl(lower)alkylamine is used in this reaction, diastereomer of the object compound (I-b) can be separated by a conventional method such as extraction, precipitation, fractional crystallization, recrystallization, chromatography, high performance liquid chromatography, and the like, to afford optically active diastereomers.

(9) Process 9:

The compound (I-c) or salts thereof can be prepared by subjecting the compound (I-l) or salts thereof to hydrolysis of N-[ar(lower)alkyl]carboxamido of $R_b^5$.

The method of hydrolysis and the reaction conditions (e.g. reaction temperature, solvent, etc.) are substantially the same as those illustrated for removal reaction of the carboxy-protective group of the compound (I-b) in Process 2, and therefore are to be referred to said explanation.

The object compound (I) obtained according to the Processes 1 to 9, can be isolated and purified in a conventional manner, for example, extraction, precipitation, fractional crystallization, recrystallization, chromatographyl, and the like.

Methods A to D for preparing the new starting compound (II) or salts thereof are explained in detail in the following.

(A) Method A

The compound (V) can be prepared by reacting the compound (III) or salts thereof with the compound (IV).

Suitable salts of the compound (III) may the same as those for the compound (I).

Some of the starting compound (III) of this method are new and can be prepared according to the known methods [e.g. J. Org. Chem., 27, 4713 (1962), etc.].

This reaction can be carried out in the presence of a base such as those given for the explanation of Process 2.

This reaction is usually carried out in a conventional solvent which does not adversely influence the reaction such as dichloromethane, methanol, ethanol, propanol, pyridine, N,N-dimethylformamide, 4-methyl-2-pentanone, tetrahydrofuran, etc., or a mixture thereof.

The reaction temperature is not critical and the reaction is usually carried out under from warming to heating.

(B) Method B

The compound (VI) can be prepared by cyclizing the compound (V).

This reaction is usually carried out in the presence of a so-called Lewis acid such as zinc halide (e.g. zinc chloride, etc.), boron trihalide (e.g. boron trichloride, boron trifluoride, etc.), titanium tetrahalide (e.g., titanium tetrachloride, titanium tetrabromide, etc.), tin tetrahalide (e.g. tin tetrachloride, tin tetrabromide etc.), aluminum halide (e.g. aluminum chloride, aluminum bromide, etc.), trihaloacetic acid (e.g. trichloroacetic acid, trifloroacetic acid, etc.), and the like, in which zinc halide is preferable.

This reaction is usually carried out in a conventional solvent which does not adversely influence the reaction such as dichloromethane, methanol, ethanol, propanol, pyridine, N,N-dimethylformamide, 4-methyl-2-pentanone, tetrahydrofuran, etc., or a mixture thereof.

The reaction temperature is not critical and the reaction is usually carried out under from warming to heating.

(C) Method C

The compound (VIII) can be prepared by reacting the compound (VI) with the compound (VII) in the presence of phosphorus oxyhalide.

Preferable phosphorus oxyhalide used in this method may be phosphorus oxychloride, etc.

This reaction is usually carried out in a conventional solvent which does not adversely influence the reaction such as dichloromethane, methanol, ethanol, propanol, acetonitrile, pyridine, N,N-dimethylformamide, 4-methyl-2-pentanone, tetrahydrofuran, etc., or a mixture thereof.

The reaction temperature is not critical and the reaction is usually carried out under cooling to heating.

(D) Method D

The compound (II) or salts thereof can be prepared by reacting the compound (VIII) with the compound (IX) or salts thereof.

This reaction can be carried out in the presence of a base such as an alkalimetal hydroxide (e.g. sodium hydroxide, potassium hydroxide, etc.), an alkaline earth metal hydroxide (e.g. magnesium hydroxide, calcium hydroxide, etc.), alkali metal hydride (e.g. sodium hydride, potassium hydride, etc.), alkaline earth metal hydride (e.g. calcium hydride, etc.), alkali metal alkoxide (e.g. sodium methoxide, sodium ethoxide, potassium t-butoxide, etc.), an alkali metal carbonate (e.g. sodium carbonate, potassium carbonate, etc.), and alkaline earth metal carbonate (e.g. magnesium carbonate, calcium carbonate, etc.), an alkali metal bicarbonate (e.g. sodium bicarbonate, potassium bicarbonate, etc.), lower alkyllithium (e.g. n-butyllithium, etc.), and the like, in which a combination of alkali metal hydride and lower alkyllithium is preferable.

This reaction is usually carried out in a conventional solvent which does not adversely influence the reaction such as dichloromethane, methanol, ethanol, propanol, pyridine, N,N-dimethylformamide, 4-methyl-2-pentanone, tetrahydrofuran, hexane, etc., or a mixture thereof.

The reaction temperature is not critical and the reaction is usually carried out under from cooling to warming.

The object compound (I) and pharmaceutically acceptable salts thereof of the present invention are potent inhibitors of the enzyme HMG-CoA and are capable of lowering blood serum cholesterol levels and blood lipid levels, therefore are particularly useful as cholesterol biosynthesis inhibiting agent.

In the present invention, the object compound (I) possessing more potent activity can be represented by the following formula:

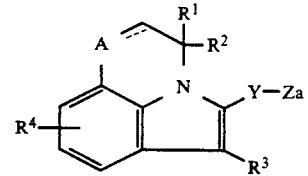

in which
$R^1$, $R^2$, $R^3$, $R^4$, A, Y and the line of ⎓ are each as defined above, and
$Z_a$ is a formula:

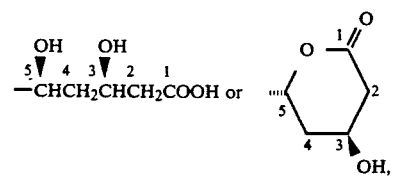

or pharmaceutically acceptable salts thereof, and it is expected that (3R,5S)-compound thereof may have the most potent activity on the analogy of X-ray Crystallography of J. Med. Chem. 29, 170 (1986).

Now in order to show the utility of the object compounds (I), the test data on HMG-CoA inhibiting activity and cholesterol biosynthesis inhibiting activity of the representative compound of the compound (I) of this invention is shown in the following.

Test Compound:
(A) Compound A: The compound of Example 2-25).
(B) Compound B: The compound of Example 13-2).

(1) Test 1 [Assay for rat liver 3-Hydroxy-3-methylglutary-Coenzyme A Reductase Activity (in vitro)]

Test Method 1:

Five µl or an enzyme solution, solubilized from rat liver microsomes and purified through the second ammonium sulfate precipitation step, is added to 35 µl of a reaction mixture containing 1.11 kBg(=0.03 µCi) or 3-hydroxy-3-metyhl [3—$^{14}$C] glutary coenzyme A, 100 mM potassium phosphate buffer, pH 7.4, 10 mM ethylenediaminetetraacetic acid (EDTA), 10 mM dithiothreitol with or without the graded concentrations of the test compound. The reaction is started by addition of 10 µl of 25 mM β-nicotinamide adenine dinucleotide phosphate, reduced form (NADPH). The mixture is incubated at 37° C. for 20 minutes. The reaction is terminated by addition of 10 µl of 2N hydrochloric acid. After an additional incubation for 15 minutes at 37° C., a 20 µl aliquot of the mixture is applied to a Silica Gel 60 F-254 plate (made by Merck & Co., Inc.). The chromatograms are developed in benzene/acetone (1:1). Sections of the thin layer plates where the mevalonolactone is located are scraped and the radioactivity are counted.

| Test Result 1: | |
| --- | --- |
| Test Compound | IC$_{50}$ (µg/ml) |
| Compound A | 0.025 |
| Compound B | 0.012 |

(2) Test 2 [Assay for Sterol Synthesis in Rats (in vivo)]

Test Method 2:

Male SD rats are administered the test compound by oral intubation. One hour after compound administration, the rats are injected intraperitoneally with sodium [1—$^{14}$C] acetate at 3.7 MBq/kg (=100 μCi/kg). After 50 minutes, 2.5 ml of blood samples are taken by cardiac puncture under short-term ether anesthesia. The plasma, obtained by centrifugation, is hydrolyzed and nonsaponifiable lipids are extracted with the petroleum ether. Sterols are isolated from these extracts as digitonide, dissolved in 1ml of methanol and the radioactivity is counted.

| Test Compound | Test Result 2: dose (mg/kg) | Inhibition (%) |
|---|---|---|
| Compound A | 10.0 | 95.7 |

For therapeutic administration, the object compound (I) and the pharmaceutically acceptable salts thereof of the present invention are used in the form of conventional pharmaceutical preparation which contains said compound, as an active ingredient, in admixture with pharmaceutically acceptable carriers such as an organic or inorganic solid or liquid excipient which is suitable for oral, parenteral and external administration.

The pharmaceutical preparations may be in solid form such as tablet, granule, powder, capsule, or liquid form such as solution, suspension, syrup, emulsion, lemonade, and the like.

If needed, there may be included in the above preparations auxiliary substances, stabilizing agents, wetting agents and other commonly used additives such as lactose, stearic acid, magnesium stearate, terra alba, sucrose, corn starch, talc, gelatin, agar, pectin, peanut oil, olive oil, cacao butter, ethylene glycol, tartaric acid, citric acid, fumaric acid, and the like.

While the dosage of the compound (I) may vary from and also depend upon the age, conditions of the patient, a kind of diseases, a kind of the compound (I) to be applied, etc. In general, amount between about 0.1 mg and about 1000 mg or even more, preferably between about 1 mg and about 200 mg per day may be administered to a patient. An average single dose of about 0.1 mg, 1 mg, 10 mg, 20 mg, 30 mg, 50 mg, 100 mg, 200 mg, 250 mg of the object compound (I) of the present invention may be used in treating hypercholesterolaemic and hyperlipoproteinaemic states and associated conditions.

The following Preparations and Examples are given for the purpose of illustrating this invention in more detail.

Preparation 1-1)

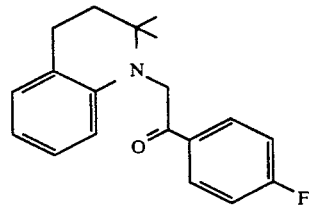

A stirred mixture of 2,2-dimethyl-1,2,3,4-tetrahydroquinoline (4.69 g) and 2-bromo-4'-fluoroacetophenone (3.17 g) in dry N,N-dimethylformamide (6 ml) was heated at 70°-80° C. for 5 hours under nitrogen. The reaction mixture was poured was triturated with diethyl ether to give pale yellow crystals. The crystals were collected and washed with methanol to give N-(4-fluorobenzoylmethyl)-2,2-dimethyl-1,2,3,4-tetrahydroquinoline (3.7 g).

MS (m/e): 297 (M+).

NMR (CDCl$_3$, δ): 1.25 (6H, s), 1.92 (2H, t, J=6Hz), 2.83 (2H, t, J=6Hz), 4.68 (2H, s), 6.06 (1H, d, J=8Hz), 6.57 (1H, t, J=8Hz), 6.9-7.01 (2H, m), 7.12-7.25 (2H, m), 7.99-8.13 (2H, m).

The compounds of Table A were obtained in substantially the same manner as that of Preparation 1-1).

TABLE A

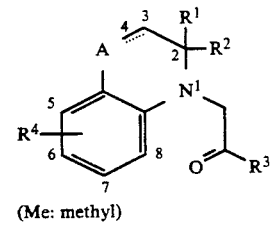

(Me: methyl)

| Preparation No. | R$^1$, R$^2$ | R$^3$ | R$^4$ | —A— |
|---|---|---|---|---|
| 1-2) | Me, Me | ⌬-Me | H | —CH$_2$— |
| 1-3) | H, Me | ⌬-F | " | " |

TABLE A-continued
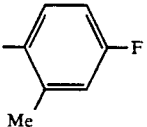
(Me: methyl)
| Preparation No. | R¹, R² | R³ | R⁴ | —A— |
|---|---|---|---|---|
| 1-4) | Me, Me | 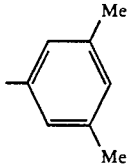 | " | " |
| 1-5) | " | 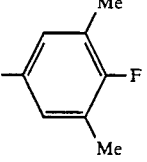 | " | " |
| 1-6) | " | 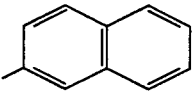 | " | " |
| 1-7) | " | 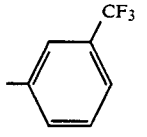 | " | " |
| 1-8) | " | 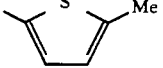 | " | " |
| 1-9) | " | 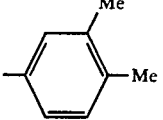 | " | " |
| 1-10) | Me, Me | 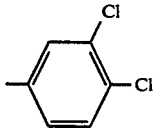 | H | —CH₂— |
| 1-11) | " | 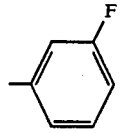 | " | " |
| 1-12) | " |  | " | " |

TABLE A-continued
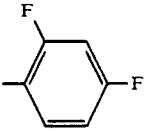
(Me: methyl)
| Preparation No. | R¹, R² | R³ | R⁴ | —A— |
|---|---|---|---|---|
| 1-13) | " | 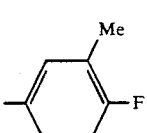 | " | " |
| 1-14) | " |  | " | " |
| 1-15) | " |  | " | " |
| 1-16) | " | 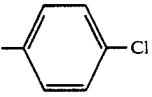 | " | " |
| 1-17) | " |  | " | " |
| 1-18) | " | 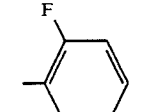 | " | " |
| 1-19) | " | 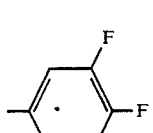 | " | " |
| 1-20) | H, H | 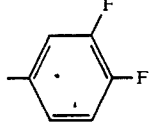 | " | " |
| 1-21) | " | 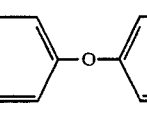 | " | " |
| 1-22) | H, H | 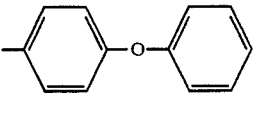 | H | —CH₂— |

TABLE A-continued
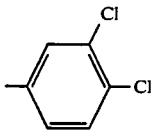
(Me: methyl)
| Preparation No. | R¹, R² | R³ | R⁴ | —A— |
|---|---|---|---|---|
| 1-23) | " | 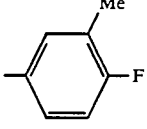 3,4-diCl-phenyl | " | " |
| 1-24) | " | 2-F-5-Me-phenyl | " | " |
| 1-25) | Me, Me | 5-F-2-MeO-phenyl | " | " |
| 1-26) | " | 2,4,6-triF-phenyl | " | " |
| 1-27) | " | 4-F-phenyl | 6-Me | " |
| 1-28) | " | " | 6-Cl | " |
| 1-29*) | " | " | 6-F | " |
| 1-30) | " | phenyl | H | " |
| 1-31) | " | 4-NMe₂-phenyl | " | " |
| 1-32) | H, H | 4-F-phenyl | " | —O— |
| 1-33) | " | " | " | —S— |
| 1-34) | Me, Me | 2-Cl-4-F-phenyl | " | —CH₂— |

TABLE A-continued

Structure: A-CH=CH-C(R¹)(R²)-N(N¹)-CH₂-C(=O)-R³ with aromatic ring bearing R⁴ at positions 5,6,7 and substituent at position 8. (Me: methyl)

| Preparation No. | R¹, R² | R³ | R⁴ | —A— |
|---|---|---|---|---|
| 1-35) | Me, Me | 4-F-phenyl | H | —CH= |
| 1-36) | H, H | 2-MeO-5-F-phenyl (methyl substituent) | " | —CH₂— |
| 1-37) | Me, Me | OH-substituted phenyl with X substituents | " | " |
| 1-38) | " | 2-MeO-phenyl (methyl) | " | " |
| 1-39) | " | 2-Cl-thiophene (methyl) | " | " |

*)This reaction was carried out in the presence of N,N-diisopropyl-N-ethylamine.

Physico-Chemical Data of Table A

| Preparation No. of Product | Data |
|---|---|
| 1-2) | IR (Film): 1710, 1600, 1495, 1325, 1070, 740 cm⁻¹<br>NMR (90MHz, CDCl₃, δ): 1.26(6H, s), 1.90 (2H, t, J=6Hz), 2.43(3H, s), 2.83(2H, t, J=6Hz), 4.68(2H, s), 6.07(1H, d, J=8Hz), 6.58(1H, m), 6.82–7.07(2H, m), 7.33–7.49(2H, m), 7.7–7.93(2H, m) |
| 1-3) | IR (Film): 2940, 1700, 1600, 1500 cm⁻¹<br>NMR (200MHz, CDCl₃, δ): 1.17(3H, d, J=6.4Hz), 1.7–2.2(2H, m), 2.7–3.0 2H, m), 3.5–3.6(1H, m), 4.55(1H, d, J=18.0Hz), 4.78(1H, d, J=18.0Hz), 6.2–8.1(8H, m) |
| 1-4) | IR (Film): 2940, 1700, 1600, 1580, 1490, 1460, 1360, 1310, 1235, 1210, 1160, 1110, 980, 860, 810, 740 cm⁻¹<br>NMR (200MHz, CDCl₃, δ): 1.24(6H, s), 1.91 (2H, t, J=6.7Hz), 2.51(3H, s), 2.82 (2H, t, J=6.7Hz), 4.54(2H, s), 6.11 (1H, d, J=8.0Hz), 6.5–6.7(1H, m), 6.9–7.1(4H, m), 7.7–7.9(1H, m) |
| 1-5) | IR (Film): 2940, 1695, 1605, 1490 cm⁻¹<br>NMR (200MHz, CDCl₃, δ): 1.25(6H, s), 1.69 (2H, t, J=6.7Hz), 2.40(6H, s), 2.83 (2H, t, J=6.7Hz), 4.69(2H, s), 6.0–7.7 (7H, m) |
| 1-6) | IR (Film): 2970, 2940, 1700, 1600, 1490 cm⁻¹<br>NMR (200MHz, CDCl₃, δ): 1.25(6H, s), 1.92 (2H, t, J=6.7Hz), 2.33(6H, s), 2.83 (2H, t), 4.66(2H, s), 6.06(1H, d, J=8.1Hz), 6.57(1H, t, J=8Hz), 6.8–7.0 (2H, m), 7.75(1H, d, J=6.9Hz) |
| 1-7) | mp: 110–120° C.<br>IR (Nujol): 1680, 1600 cm⁻¹<br>NMR (200MHz, CDCl₃, δ): 1.29(6H, s), 1.95 (2H, t, J=6.7Hz), 2.85(2H, t, J=6.7Hz), 4.86(2H, s), 6.14(1H, d, J=8.0Hz), 6.61(1H, t, J=8.0Hz), 6.8–7.0(2H, m), 7.5–7.7(2H, m), 7.8–8.2(4H, m), 8.61(1H, s) |
| 1-8) | IR (Neat): 2920, 1690, 1600, 735 cm⁻¹<br>NMR (CDCl₃, δ): 1.30(6H, s), 1.92(2H, t, J=7.5Hz), 2.85(2H, t, J=7.5Hz), 4.70 (2H, s), 6.08(1H, d, J=8Hz), 6.61(1H, t, J=8.7Hz), 6.8–7.1(2H, m), 7.5–8.5 (4H, m) |
| 1-9) | IR (Nujol): 1680, 1235, 740 cm⁻¹<br>NMR (200MHz, CDCl₃, δ): 1.26(6H, s), 1.92 (2H, t, J=6Hz), 2.53(3H, s), 2.83(2H, t, J=6Hz), 4.48(2H, s), 6.24(1H, d, J=8Hz), 6.60(1H, d, J=6Hz), 6.81(1H, d, J=4Hz), 6.92–7.01(2H, m), 7.75(1H, d, J=4Hz) |
| 1-10) | IR (Nujol): 1690, 1605, 1490, 1240, 1165, 740 cm⁻¹ |

Physico-Chemical Data of Table A -continued

| Preparation No. of Product | Data |
|---|---|
| 1-11) | NMR (200MHz, CDCl₃, δ): 1.25(6H, s), 1.92 (2H, t, J=6Hz), 2.35(6H, s), 2.83(2H, t, J=6Hz), 4.69(2H, s), 6.08(1H, d, J=8Hz), 6.56(1H, t, J=7Hz), 6.88–6.99 (2H, m), 7.26(1H, d, J=6Hz), 7.81(1H, d, J=6Hz), 7.83(1H, s) |
| 1-12) | IR (Nujol): 1710, 1600, 1460, 1200, 740 cm⁻¹<br>NMR (200MHz, CDCl₃, δ): 1.24(6H, s), 1.91 (2H, t, J=6Hz), 2.83(2H, t, J=6Hz), 4.65(2H, s), 6.03(1H, d, J=8Hz), 6.59 (1H, t, J=6Hz), 6.91–7.01(2H, m), 7.59 (1H, d, J=8Hz), 7.89(1H, dd, J=2Hz, 8Hz), 8.14(1H, d, J=2Hz) |
| 1-13) | IR (Nujol): 1700, 1490, 1250, 1160, 735 cm⁻¹<br>NMR (200MHz, CDCl₃, δ): 1.25(6H, s), 1.92 (2H, t, J=6Hz), 2.83(2H, t, J=6Hz), 4.69(2H, s), 6.06(1H, d, J=8Hz), 6.55 (1H, t, J=7Hz), 6.91–7.01(2H, m), 7.31–7.37(1H, m), 7.48–7.53(1H, m), 7.70–7.88(2H, m) |
| 1-14) | IR (Nujol): 1700, 1612, 1195, 1160, 732 cm⁻¹<br>NMR (CDCl₃, δ): 1.25(6H, s), 1.91(2H, t, J=6.5Hz), 2.82(2H, t, J=6.5Hz), 4.59 (2H, s), 6.05(1H, d, J=8.1Hz), 6.58 (1H, t, J=7.2Hz), 6.89–7.07(4H, m), 8.01(1H, m) |
| 1-15) | mp: 92–103° C.<br>IR (Nujol): 1693, 1494, 1155, 1128, 740 cm⁻¹<br>NMR (CDCl₃, δ): 1.25(6H, s), 1.92(2H, t, J=6.5Hz), 2.35(3H, s), 2.83(2H, t, J=6.5Hz), 4.67(2H, s), 6.06(1H, d, J=8.0Hz), 6.57(1H, t, J=6.8Hz), 6.89–7.16(3H, m), 7.86–7.94(2H, m) |
| 1-16) | mp: 88–93° C.<br>IR (Nujol): 1698, 1587, 1490, 739 cm⁻¹<br>NMR (CDCl₃, δ): 1.24(6H, s), 1.91(2H, t, J=6.5Hz), 2.83(2H, t, J=6.5Hz), 4.68 (2H, s), 6.05(1H, d, J=8.1Hz), 6.58 (1H, t, J=7.7Hz), 6.95(2H, m), 7.49 (2H, d, J=8.6Hz), 8.00(2H, d, J=8.6Hz) |
| 1-17) | IR (Neat): 1702, 1610, 1160, 739 cm⁻¹<br>NMR (CDCl₃, δ): 1.25(6H, s), 1.91(2H, t, J=6.5Hz), 2.83(2H, t, J=6.5Hz), 4.63 (2H, s), 6.08(1H, d, J=8.2Hz), 6.56(1H, m), 6.91–7.33(4H, m), 7.58(1H, m), 7.94(1H, m) |
| 1-18) | IR (Neat): 1705, 1605, 1155, 740 cm⁻¹<br>NMR (CDCl₃, δ): 1.24(6H, s), 1.92(2H, t, J=6.5Hz), 2.83(2H, t, J=6.5Hz), 4.66 (2H, s), 6.04(1H, d, J=8.1Hz), 6.59 (1H, t, J=7.7Hz), 6.90–7.36(3H, m), 7.82–7.95(2H, m) |
| 1-19) | IR (Nujol): 1700, 1600, 1580, 1220, 749 cm⁻¹<br>NMR (CDCl₃, δ): 1.25(6H, s), 1.91(2H, t, J=6.5Hz), 2.83(2H, t, J=6.5Hz), 4.68 (2H, s), 6.09(1H, d, J=8.2Hz), 6.57 (1H, t, J=8Hz), 6.90–7.45(9H, m), 8.05 (2H, d, J=10Hz) |
| 1-20) | IR (Film): 1695, 1605, 740 cm⁻¹<br>NMR (CDCl₃, δ): 1.25(6H, s), 1.91(2H, t, J=6.5Hz), 2.37(3H, s), 2.50(3H, s), 2.82(2H, t, J=6.5Hz), 4.56(2H, s), 6.11(1H, d, J=8Hz), 6.5–7.2(5H, m), 7.94(1H, d, J=8Hz) |
| 1-21) | MASS m/e: 2.69(M⁺), 146<br>NMR (CDCl₃, δ): 2.00(2H, m), 2.81(2H, m), 3.36(2H, m), 4.63(2H, s), 6.29(1H, d, J=8Hz), 6.58(1H, t, J=6.8Hz), 6.9–7.2 (4H, m), 7.98(2H, m) |
| 1-22) | mp: 114–115° C. |
| 1-23) | mp: 104–107° C.<br>IR (Nujol): 1690, 1608, 1510, 745 cm⁻¹<br>NMR (CDCl₃, δ): 2.02(2H, m), 2.33(6H, s), 2.82(2H, t, J=6.3Hz), 3.39(2H, t, J=5.7Hz), 4.66(2H, s), 6.29(1H, d, J=8.0Hz), 6.57(1H, t, J=7.3Hz), 6.94 (2H, m), 7.23(1H, d, J=6.0Hz), 7.74 (1H, d, J=9.3Hz), 7.76(1H, s) |
| 1-24) | mp: 105–107° C.<br>IR (Nujol): 1702, 1600, 1580, 745 cm⁻¹<br>NMR (CDCl₃, δ): 2.02(2H, m), 2.82(2H, t, J=6.4Hz), 3.37(2H, t, J=5.7Hz), 4.62 (2H, s), 6.27(1H, d, J=7.9Hz), 6.61 (1H, t, J=7.3Hz), 6.96(2H, m), 7.44 (1H, d, J=8.3Hz), 7.81(1H, d, J=8.5Hz), 8.06(1H, s) |
| 1-25) | mp: 77.0–78.5° C.<br>IR (Nujol): 1690, 1600, 1160, 1114, 738 cm⁻¹<br>NMR (CDCl₃, δ): 2.02(2H, m), 2.33(3H, s), 2.83(2H, t, J=6.3Hz), 3.38(2H, t, J=5.7Hz), 4.65(2H, s), 6.28(1H, d, J=7.9Hz), 6.59(1H, t, J=7.0Hz), 6.91–7.13(3H, m), 7.86(2H, m) |
| 1-26) | IR (Film): 1690, 1605, 1595, 1280, 835, 740 cm⁻¹<br>NMR (200MHz, CDCl₃, δ): 1.24(6H, s), 1.90 (2H, t, J=6Hz), 2.81(2H, t, J=6Hz), 3.96(3H, m), 4.62(2H, s), 6.08–7.9 (6H, m) |
| 1-27) | IR (Film): 1710, 1640, 1600, 740 cm⁻¹<br>NMR (200MHz, CDCl₃, δ): 1.24(6H, s), 1.89 (2H, t, J=6Hz), 2.81(2H, t, J=6Hz), 4.47(2H, s), 6.2–7.1(5H, m) |
| 1-28) | NMR (CDCl₃, δ): 1.23(6H, s), 1.89(2H, t, J=6Hz), 2.21(3H, s), 2.80(2H, t, J=6Hz), 4.65(2H, s), 5.98(1H, d, J=10Hz), 6.8–7.2(4H, m), 8.10(2H, m) |
| 1-29) | NMR (CDCl₃, δ): 1.25(6H, s), 1.87(2H, t, J=6.3Hz), 2.78(2H, t, J=6.3Hz), 4.65 (2H, s), 5.95(1H, d, J=9.0Hz), 6.7–7.3(4H, m), 7.9–8.3(2H, m) |
| 1-30) | NMR (CDCl₃, δ): 1.23(6H, s), 1.90(2H, t, J=6Hz), 2.80(2H, t, J=6Hz), 4.65(2H, s), 5.95(1H, m), 6.3–6.7(2H, m), 7.1–7.2(2H, m), 8.0–8.1(2H, m) |
| 1-31) | mp: 121–124° C.<br>IR (Nujol): 1703, 1602, 1500, 738 cm⁻¹<br>NMR (CDCl₃, δ): 1.25(6H, s), 1.92(2H, t, J=6.5Hz), 2.83(2H, t, J=6.5Hz), 4.72 (2H, s), 6.09(1H, d, J=8.2Hz), 6.57 (1H, t, J=7.3Hz), 6.90–7.00(2H, m), 7.47–7.66(3H, m), 8.04–8.08(2H, m) |
| 1-32) | mp: 172–177° C.<br>IR (Nujol): 1676, 1600, 1188, 743 cm⁻¹<br>NMR (CDCl₃, δ): 1.16(6H, s), 1.83(2H, t, J=6.6Hz), 2.73(2H, t, J=6.1Hz), 2.97(6H, s), 4.53(2H, s), 6.04(1H, d, J=7.8Hz), 6.30–7.00(5H, m), 7.92(2H, d, J=8.4Hz) |
| 1-33) | IR (Nujol): 1690, 1600, 1505 cm⁻¹<br>NMR (CDCl₃, δ): 3.43(2H, t, J=5Hz), 4.28 (2H, t, J=5Hz), 6.3–6.9(4H, m), 7.13 (2H, t, J=8Hz), 8.00(2H, dd, J=6 and 8Hz) |
| 1-34) | IR (Nujol): 1695, 1600 cm⁻¹<br>NMR (CDCl₃, δ): 3.10(2H, t, J=5.2Hz), 3.72(2H, t, J=5.2Hz), 4.72(2H, s), 6.32(1H, d, J=8.2Hz), 6.63(1H, t, J=8.2Hz), 6.90(1H, t, J=8.2Hz), 7.06–7.26(3H, m), 8.00–8.07(2H, m) |
| 1-35) | IR (Neat): 1710, 1600, 1220, 740 cm⁻¹<br>NMR (CDCl₃, δ): 1.23(6H, s), 1.87(2H, t, J=6.5Hz), 2.80(2H, t, J=6.5Hz), 4.58 (2H, s), 6.20(1H, d, J=8.3Hz), 6.62(1H, t, J=6.8Hz), 7.01–7.55(5H, m) |
| | mp: 95–98° C.<br>IR (Nujol): 1690, 1598, 1227, 1154, 737 cm⁻¹<br>NMR (CDCl₃, δ): 1.37(6H, s), 4.69(2H, s), 5.41(1H, d, J=9.8Hz), 5.99(1H, d, J=8.1Hz), 6.28(1H, d, J=9.8Hz), 6.54 (1H, t, J=7.3Hz), 6.85–6.95(2H, m), 7.18(2H, t, J=8.7Hz), 8.05–8.14(2H, m) |

-continued

Physico-Chemical Data of Table A

| Preparation No. of Product | Data |
|---|---|
| 1-36) | mp: 78-83° C.<br>IR (Nujol): 1679, 1603, 1280, 1155, 750 cm$^{-1}$<br>NMR (CDCl$_3$, δ): 2.00(2H, quintet, J=5.8Hz), 2.81(2H, t, J=6.3Hz), 3.39 (2H, t, J=5.7Hz), 3.95(3H, s), 4.60 (2H, s), 6.26(1H, d, J=7.8Hz), 6.52-7.06(5H, m), 7.85(1H, m) |
| 1-37) | IR (Neat): 3620, 2940, 1690, 1600, 1490 cm$^{-1}$<br>NMR (CDCl$_3$, δ): 1.26(6H, s), 1.49(18H, s), 1.91(2H, t, J=6.7Hz), 2.83(2H, t, J=6.7Hz), 4.68(2H, s), 5.77(1H, s), 6.12(1H, d, J=7.8Hz), 6.5-7.0(3H, m), 7.95(2H, s) |
| 1-38) | mp: 74-84° C.<br>IR (Nujol): 1700, 1600 cm$^{-1}$<br>NMR (CDCl$_3$, δ): 1.25(6H, s), 1.75(2H, t, J=6.8Hz), 2.83(2H, t, J=6.8Hz), 3.87 (3H, s), 4.71(2H, s), 6.09(1H, d, J=8.0Hz), 6.57(1H, t, J=7.3Hz), 6.9-7.0 (2H, m), 7.16(1H, m), 7.42(1H, t, J=8.0Hz), 7.57(1H, t, J=1.5Hz), 7.66 (1H, d, J=7.3Hz) |
| 1-39) | IR (Film): 1675, 1410, 1220, 1010, 745 cm$^{-1}$<br>NMR (200MHz, CDCl$_3$, δ): 1.26(6H, s), 1.95 (2H, t, J=6Hz), 2.85(2H, t, J=6Hz), 4.38(2H, s), 6.26(1H, d, J=8Hz), 6.65 (1H, t, J=7Hz), 6.94-7.04(3H, m), 7.74 (1H, d, J=4Hz) |

Preparation 2-1)

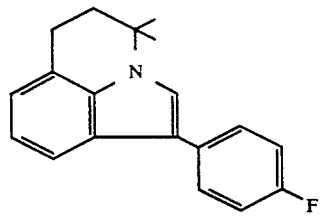

A mixture of N-(4-fluorobenzolymethyl)-2,3-dimethyl-1,2,3,4-tetrahydroquinoline (3.96 g) and zinc chloride (12.7 g) in dry ethyl alcohol (20 ml) was refluxed for 1.5 hours. The reaction mixture was poured into cold 2N hydrochloric acid (50 ml) and extracted with ethyl acetate. The extract was washed with saturated aqueous sodium hydrogen carbonate and filtered. The filtrate was evaporated under reduced pressure. The residue was subjected to a column chromatography on silica gel (40 g) and eluted with a mixture of n-hexane and ethyl acetate (20:1, V/V). The fractions containing the object compound were collected and concentrated under reduced pressure to give colorless syrup of 5,6l-dihydro-4,4-dimethyl-1-(4-fluorphenyl)-4H-pyrrolo-[3,2,1-ij]quinoline (3.72 g).

IR (Neat): 1540, 1450, 1220, 1185, 745 cm$^{-1}$

NMR (CDCl$_3$, δ): 1.56 (6H, s), 2.08 (2H, t, J=6Hz), 3.05 (2H, t, J=6Hz), 6.97-7.24 (4H, m), 7.39 (1H, s), 7.59-7.71 (3H, m).

MS (m/e): 279 (M$^+$).

The compounds of Table B were obtained in substantially the same manner as that of Preparation 2-1).

TABLE B

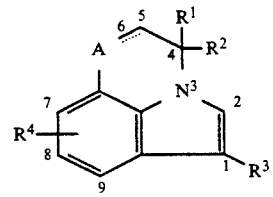

| Preparation No. | R$^1$, R$^2$ | R$^3$ | R$^4$ | —A— |
|---|---|---|---|---|
| 2-2) | Me, Me | 3-Me-phenyl | H | —CH$_2$— |
| 2-3) | H, Me | 4-F-phenyl | " | " |
| 2-4) | Me, Me | 4-F-3-Me-phenyl | " | " |
| 2-5) | " | 3,5-diMe-phenyl | " | " |

TABLE B-continued

[Structure: indole-type scaffold with positions labeled 2, 3, 4, 5, 6, 7, 8, 9; R¹ and R² on C4; A-CH=CH- group at position 7; R³ at position 3; R⁴ at positions 5/6; N³ in ring]

| Preparation No. | R¹, R² | R³ | R⁴ | —A— |
|---|---|---|---|---|
| 2-6) | " | 2,5-(Me)₂-3-F-phenyl (Me, F, Me substituted phenyl) | " | " |
| 2-7) | " | 2-naphthyl | " | " |
| 2-8) | " | 3-CF₃-phenyl | " | " |
| 2-9) | " | 5-Me-thiophen-2-yl | " | " |
| 2-10) | Me, Me | 2,5-(Me)₂-phenyl | H | —CH₂— |
| 2-11) | " | 3,4-Cl₂-phenyl | " | " |
| 2-12) | " | 3-F-phenyl | " | " |
| 2-13) | " | 2,4-F₂-phenyl | " | " |
| 2-14) | " | 2-F-5-Me-phenyl | " | " |
| 2-15) | " | 4-Cl-phenyl | " | " |

TABLE B-continued
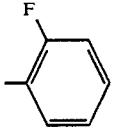
| Preparation No. | R¹, R² | R³ | R⁴ | —A— |
|---|---|---|---|---|
| 2-16) | " | 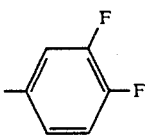 | " | " |
| 2-17) | " | 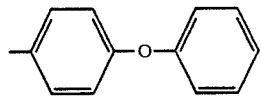 | " | " |
| 2-18) | " | 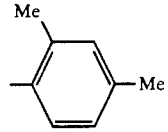 | " | " |
| 2-19) | " | 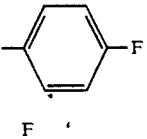 | " | " |
| 2-20) | H, H | 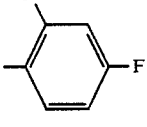 | " | " |
| 2-21) | " | 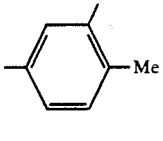 | " | " |
| 2-22) | " | 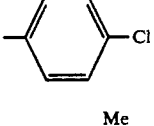 | " | " |
| 2-23) | H, H | 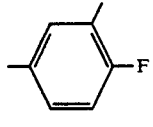 | H | —CH₂— |
| 2-24) | " | 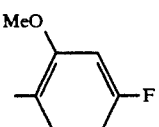 | " | " |
| 2-25) | Me, Me | MeO<br>(phenyl with F) | " | " |

TABLE B-continued

Structure: indole with positions labeled — N3, 2, 1-R³, 9, 8-R⁴, 7, A at position (via 6=5 vinyl to C4 bearing R¹, R²)

| Preparation No. | R¹, R² | R³ | R⁴ | —A— |
|---|---|---|---|---|
| 2-26) | " | 2,4,5-triF-phenyl | " | " |
| 2-27) | " | 4-F-phenyl | 8-Me | " |
| 2-28) | " | " | 8-Cl | " |
| 2-29) | " | " | 8-F | " |
| 2-30) | " | phenyl | H | " |
| 2-31) | " | 4-(NMe₂)-phenyl | " | " |
| 2-32) | H, H | 4-F-phenyl | " | —O— |
| 2-33) | " | " | " | —S— |
| 2-34) | Me, Me | 2-Cl-4-F-phenyl | " | —CH₂— |
| 2-35) | " | 4-F-phenyl | " | —CH= |
| 2-36) | H, H | 2-MeO-4-F-phenyl | H | —CH₂— |
| 2-37) | Me, Me | 2,6-diX-4-(...)-hydroxyphenyl (OH, X substituents) | " | " |

TABLE B-continued

| Preparation No. | $R^1$, $R^2$ | $R^3$ | $R^4$ | —A— |
|---|---|---|---|---|
| 2-38) | " | MeO-phenyl (ortho) | " | " |
| 2-39) | " | 2-chloro-thiophene | " | " |

| Physico-Chemical Data of Table B | |
|---|---|
| Preparation No. of Product | Data |
| 2-2) | IR (Film): 1610, 1450, 1180, 745 cm$^{-1}$<br>NMR (200MHz, CDCl$_3$, δ): 1.57(6H, s), 2.08 (2H, t, J=6Hz), 2.42(3H, s), 3.06(2H, t, J=6Hz), 6.97-7.78(8H, m) |
| 2-3) | IR (Film): 3050, 2980, 2940, 1615, 1540, 1500 cm$^{-1}$<br>NMR (200MHz, CDCl$_3$, δ): 1.58(3H, d, J=6.5Hz), 1.9-2.4(2H, m), 3.04(2H, t, J=6.1Hz), 4.2-4.5(1H, m), 6.97(1H, d, J=7.0Hz), 7.0-7.2(3H, m), 7.32(1H, s), 7.5-7.7(3H, m) |
| 2-4) | IR (Film): 3050, 2980, 2940, 1615, 1585, 1540 cm$^{-1}$<br>NMR (200MHz, CDCl$_3$, δ): 1.56(6H, s), 2.0-2.2(2H, m), 2.33(3H, s), 3.07(2H, t, J=6.5Hz), 6.8-7.4(7H, m) |
| 2-5) | IR (Nujol): 1600, 1530 cm$^{-1}$<br>NMR (200MHz, CDCl$_3$, δ): 1.56(6H, s), 2.07 (2H, t, J=6.5Hz), 2.38(6H, s), 3.05 (2H, t, J=6.5Hz), 6.89(1H, s), 6.98 (1H, d, J=7.0Hz), 7.10(1H, t, J=7.0Hz), 7.32(2H, s), 7.43(1H, s), 7.77(1H, d, J=7.0Hz) |
| 2-6) | IR (Film): 3050, 2980, 2940, 1615, 1535 cm$^{-1}$<br>NMR (200MHz, CDCl$_3$, δ): 1.55(6H, s), 2.07(2H, t, J=6.2Hz), 2.32(6H, d, J=2.1Hz), 3.05(2H, t, J=6.2Hz), 6.98 (1H, d, J=7.0Hz), 7.10(1H, t, J=7.0Hz), 7.30(2H, d, J=6.9Hz), 7.36(1H, s), 7.70(1H, d, J=7.0Hz) |
| 2-7) | IR (Film): 3050, 2980, 2940, 1630, 1600, 1530 cm$^{-1}$<br>NMR (200MHz, CDCl$_3$, δ): 1.59(6H, s), 2.10 (2H, t, J=4.9Hz), 3.07(2H, t, J=4.9Hz), 7.02(1H, d, J=7.0Hz), 7.1-7.5(4H, m), 7.57(1H, s), 7.8-8.0(4H, m), 8.15(1H, s) |
| 2-8) | IR (Neat): 2970, 1613, 1535, 745 cm$^{-1}$<br>NMR (CDCl$_3$, δ): 1.58(6H, s), 2.09(2H, t, J=6Hz), 3.06(2H, t, J=6Hz), 7.0-7.2 (2H, m), 7.4-7.6(3H, m), 7.7-7.9(3H, m) |
| 2-9) | IR (Film): 1670, 1445, 1180, 785, 740 cm$^{-1}$<br>NMR (200MHz, CDCl$_3$, δ): 1.54(6H, s), 2.06 (2H, t, J=6Hz), 2.51(3H, s), 3.03(2H, t, J=6Hz), 6.72(1H, m), 6.96-7.14(3H, m), 7.40(1H, s), 7.73(1H, d, J=8Hz) |
| 2-10) | IR (Film): 1615, 1540, 1185, 740 cm$^{-1}$<br>NMR (200MHz, CDCl$_3$, δ): 1.55(6H, s), 2.07 (2H, t, J=6Hz), 2.30(3H, s), 2.33(3H, s), 3.05(2H, t, J=6Hz), 6.96-7.22(3H, m), 7.37(1H, s), 7.41-7.47(2H, m), 7.75(1H, d, J=8Hz) |
| 2-11) | IR (Film): 1590, 1530, 1450, 1350, 1180, 740 cm$^1$<br>NMR (200MHz, CDCl$_3$, δ): 1.56(6H, s), 2.08 (2H, t, J=6Hz), 3.05(2H, t, J=6Hz), 6.99-7.77(7H, m) |
| 2-12) | IR (Film): 1610, 1450, 1180, 745 cm$^{-1}$<br>NMR (200MHz, CDCl$_3$, δ): 1.57(6H, s), 2.08 (2H, t, J=6Hz), 3.06(2H, t, J=6Hz), 6.91-7.49(7H, m), 7.73-7.77(1H, m) |
| 2-13) | mp: 73.5-74.5° C.<br>IR (Nujol): 1590, 1535, 1188, 1140, 750 cm$^{-1}$<br>NMR (CDCl$_3$, δ): 1.57(6H, s), 2.09(2H, t, J=6.4Hz), 3.06(2H, t, J=6.4Hz), 6.89-7.24(4H, m), 7.52-7.77(3H, m) |
| 2-14) | IR (Neat): 1612, 1534, 1180, 1113, 736 cm$^{-1}$<br>NMR (CDCl$_3$, δ): 1.56(6H, s), 2.08(2H, t, J=6.4Hz), 2.34(3H, s), 3.05(2H, t, J=6.4Hz), 6.97-7.72(7H, m) |
| 2-15 | mp: 68-71° C.<br>IR (Neat): 1615, 1598, 1535, 743 cm$^{-1}$<br>NMR (CDCl$_3$, δ): 1.56(6H, s), 2.08(2H, t, J=6.4Hz), 3.05(2H, t, J=6.4Hz), 6.98-7.72(8H, m) |
| 2-16) | IR (Neat): 1615, 1536, 1185, 745 cm$^{-1}$<br>NMR (CDCl$_3$, δ): 1.57(6H, s), 2.09(2H, t, J=6.4Hz), 3.06(2H, t, J=6.4Hz), 6.99-7.83(8H, m) |
| 2-17) | IR (Neat): 1600, 1540, 1500, 770, 743 cm$^{-1}$<br>NMR (CDCl$_3$, δ): 1.56(6H, s), 2.08(2H, t, J=6.4Hz), 3.05(2H, t, J=6.4Hz), 6.99-7.70(7H, m) |
| 2-18) | IR (Neat): 1538, 1448, 1230, 745 cm$^{-1}$<br>NMR (CDCl$_3$, δ): 1.56(6H, s), 2.08(2H, t, J=6.4Hz), 3.05(2H, t, J=6.4Hz), 7.01-7.75(13H, m) |
| 2-19) | mp: 98-99° C.<br>IR (Nujol): 1610, 1535, 1182, 750 cm$^{-1}$<br>NMR (CDCl$_3$, δ): 1.55(6H, s), 2.10(2H, t, J=6.4Hz), 2.33(3H, s), 2.37(3H, s), 3.06(2H, t, J=6.4Hz), 6.95-7.39(7H, m) |
| 2-20) | IR (Neat): 2930, 1540, 746 cm$^{-1}$<br>NMR (CDCl$_3$, δ): 2.20(2H, m), 2.96(2H, m), 4.09(2H, m), 6.9-7.2(4H, m), 7.5-7.7 (3H, m)<br>MASS (m/e): 251(M$^+$) |
| 2-21) | mp: 91-92° C.<br>IR (Nujol): 1613, 1595, 1545, 1166, 750 cm$^{-1}$<br>NMR (CDCl$_3$, δ): 2.27(2H, m), 3.02(2H, t, J=6.1Hz), 4.20(2H, t, J=5.7Hz), 6.87-7.77(2H, m) |

Physico-Chemical Data of Table B

| Preparation No. of Product | Data |
|---|---|
| 2-22) | mp: 74–77° C.<br>IR (Nujol): 1614, 1538, 742 cm$^{-1}$<br>NMR (CDCl$_3$, δ): 2.26(2H, m), 2.29(3H, s), 2.33(3H, s), 3.01(2H, t, J=6.1Hz), 4.17(2H, t, J=5.7Hz), 6.92–7.77(7H, m) |
| 2-23) | mp: 103–104.5° C.<br>IR (Nujol): 1590, 1530, 743 cm$^{-1}$<br>NMR (CDCl$_3$, δ): 2.26(2H, m), 3.02(2H, t, J=6.1Hz), 4.19(2H, t, J=5.7Hz), 6.96–7.75(7H, m) |
| 2-24) | mp: 96–98.5° C.<br>IR (Nujol): 1610, 1540, 1170, 1114, 744 cm$^{-1}$<br>NMR (CDCl$_3$, δ): 2.26(2H, m), 2.33(3H, s), 3.02(2H, t, J=6.1Hz), 4.19(2H, t, J=5.7Hz), 6.94–7.71(7H, m) |
| 2-25) | IR (Film): 1600, 1450, 1280, 1185, 1035, 745 cm$^{-1}$<br>NMR (200MHz, CDCl$_3$, δ): 1.57(6H, s), 2.08 (2H, t, J=6Hz), 3.05(2H, t, J=6Hz), 3.85(3H, s), 6.7–7.6(6H, m) |
| 2-26) | IR (Film): 1595, 1445, 1115, 1025, 740 cm$^{-1}$<br>NMR (200MHz, CDCl$_3$, δ): 1.57(6H, s), 2.10 (2H, t, J=6Hz), 3.07(2H, t, J=6Hz), 6.7–7.6(5H, m) |
| 2-27) | NMR (CDCl$_3$, δ): 1.54(6H, s), 2.06(2H, t, J=6Hz), 2.46(3H, s), 3.01(2H, t, J=6Hz), 6.84(1H, s), 7.10(2H, m), 7.34 (1H, s), 7.47(1H, s), 7.62(2H, m) |
| 2-28) | NMR (CDCl$_3$, δ): 1.55(6H, s), 2.06(2H, t, J=8Hz), 3.01(2H, t, J=8Hz), 6.9–7.2 (3H, m), 7.39(1H, s), 7.5–7.7(3H, m) |
| 2-29) | NMR (CDCl$_3$, δ): 1.55(6H, s), 2.07(2H, t, J=6Hz), 3.02(2H, t, J=6Hz), 6.78(1H, d, J=10Hz), 7.0–7.4(3H, m), 7.41(1H, s), 7.59(2H, m) |
| 2-30) | IR (Neat): 1603, 1538, 1450, 1183, 743 cm$^{-1}$<br>NMR (CDCl$_3$, δ): 1.56(6H, s), 2.08(2H, t, J=6.4Hz), 3.05(2H, t, J=6.4Hz), 6.97–7.78(9H, m) |
| 2-31) | IR (Neat): 2900, 1610, 1223, 740 cm$^{-1}$<br>NMR (CDCl$_3$, δ): 1.55(6H, s), 2.07(2H, t, J=6.4Hz), 3.01(6H, br s), 3.04(2H, t, J=6.4Hz), 6.83–7.75(8H, m) |
| 2-32) | IR (Nujol): 1630, 1580, 1540, 1500 cm$^{-1}$<br>NMR (CDCl$_3$, δ): 4.29(2H, dd, J=4.4 and 5.8Hz), 4.53(2H, dd, J=4.4 and 5.8Hz), 6.71(1H, d, J=7.6Hz), 7.01–7.18(3H, m), 7.20(1H, s), 7.43(1H, d, J=8.1Hz), 7.56–7.65(2H, m) |
| 2-33) | mp: 98–99° C.<br>IR (Nujol): 1600, 1540, 1500 cm$^{-1}$<br>NMR (CDCl$_3$, δ): 3.29(2H, t, J=5.0Hz), 4.46 (2H, t, J=5.0Hz), 7.0–7.2(5H, m), 7.5–7.7(3H, m) |
| 2-34) | IR (Neat): 1603, 1535, 1230, 744 cm$^{-1}$<br>NMR (CDCl$_3$, δ): 1.57(6H, s), 2.11(2H, t, J=6.4Hz), 3.07(2H, t, J=6.4Hz), 6.98–7.28(4H, m), 7.42–7.60(3H, m) |
| 2-35) | IR (Film): 1539, 1220, 1183, 742 cm$^{-1}$<br>NMR (CDCl$_3$, δ): 1.65(6H, s), 5.71(1H, d, J=9.9Hz), 6.58(1H, d, J=9.9Hz), 7.00–7.35(5H, m), 7.57–7.66(3H, m) |
| 2-36) | mp: 128–129° C.<br>IR (Nujol): 1601, 1494, 1277, 1152, 746 cm$^{-1}$<br>NMR (CDCl$_3$, δ): 2.26(2H, quint, J=5.9Hz), 3.01(2H, t, J=6.1Hz), 3.85(3H, s), 4.20(2H, t, J=5.7Hz), 6.71–6.79(2H, m), 6.93(1H, d, J=7.0Hz), 7.05(1H, t, J=7.5Hz), 7.38(1H, s), 7.53–7.62(2H, m) |
| 2-37) | IR (Neat): 3640, 2960, 1610, 1530 cm$^{-1}$<br>NMR (CDCl$_3$, δ): 1.51(18H, s), 1.56(6H, s), 2.08(2H, t, J=6.2Hz), 3.05(2H, t, J=6.2Hz), 5.13(1H, s), 6.9–7.3(2H, m), 7.33(1H, s), 7.49(2H, s), 7.68(1H, d, J=7.9Hz) |
| 2-38) | IR (Neat): 2970, 2940, 1605, 1575, 1535 cm$^{-1}$<br>NMR (CDCl$_3$, δ): 1.56(6H, s), 2.08(2H, t, J=6.2Hz), 3.05(2H, t, J=6.2Hz), 3.87 (3H, s), 6.80(1H, m), 6.99(1H, d, J=7.1Hz), 7.0–7.4(4H, m), 7.44(1H, s), 7.76(1H, d, J=7.9Hz) |
| 2-39) | IR (Nujol): 2980, 2940, 1560 cm$^{-1}$<br>NMR (200MHz, CDCl$_3$, δ): 1.54(6H, s), 2.06 (2H, t, J=6.5Hz), 3.04(2H, t, J=6.5Hz), 6.87(1H, d, J=3.8Hz), 6.98(1H, d, J=3.8Hz), 7.01(1H, d, J=7.9Hz), 7.12 (1H, t, J=7.9Hz), 7.40(1H, s), 7.68 (1H, d, J=7.9Hz) |

Preparation 3-1)

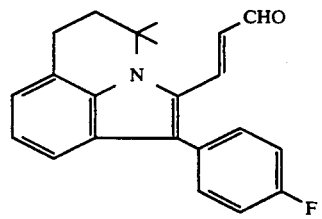

A solution of 3-dimethylaminoacrylaldehyde (3.68 g) in dry acetonitrile (10 ml) was slowly added over a 30-minute period to a solution of phosphorus oxychloride (6.07 g) in dry acetonitrile (10 ml) with stirring at 0°–10° C. under nitrogen. A solution of 5,6-dihydro-4,4-dimethyl-1-(4-fluorophenyl)-4H-pyrrolo[3,2,1-ij]quinoline (3.70 g) in dry acetonitrile (9 ml) was slowly added to the reaction mixture at the same temperature. The reaction mixture was refluxed for 7.1 hours under nitrogen, cooled to room temperature and slowly poured into a cold solution of sodium hydroxide (6.34 g) in water (130 ml) with stirring. The reaction mixture was extracted twice with toluene. The extracts were combined, washed with saturated aqueous sodium chloride, dried over anhydrous magnesium sulfate and evaporated under reduced pressure. The residue was chromatographed on a silica gel column eluting with a mixture of n-hexane and ethyl acetate (5:1, V/V). The fractions containing the object compound were collected and evaporated under reduced pressure. The residual oil was triturated with n-hexane to give yellow crystals of (E)-3-[5,6-dihydro-4,4-dimethyl-1-(4-fluorophenyl)-4H-pyrrolo[3,2,1-ij]quinolin-2-yl]acrylaldehyde (3.11 g).

mp: 157.5°–160.5° C.

IR (Nujol): 1665, 1660, 1540, 1220, 1120 cm$^{-1}$

NMR (CDCl$_3$, δ): 1.74 (6H, s), 2.15 (2H, t, J=6Hz), 3.03 (2H, t, J=6Hz), 6.14 (1H, dd, J=8 and 16Hz), 6.98–7.38 (7H, m), 7.81 (1H, d, J=16Hz), 9.55 (1H, d, J=8Hz).

The compounds of Table C were obtained in substantially the same manner as that of Preparation 3-1).

TABLE C

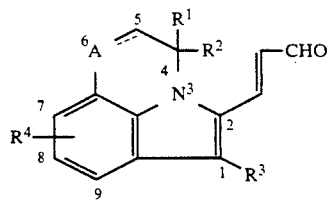

| Preparation No | R¹, R² | R³ | R⁴ | —A— |
|---|---|---|---|---|
| 3-2) | Me, Me | 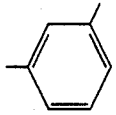 (3-Me-phenyl) | H | —CH₂— |
| 3-3) | H, Me | 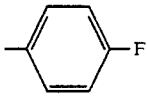 (4-F-phenyl) | " | " |
| 3-4) | Me, Me | 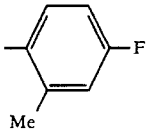 (4-F-2-Me-phenyl) | " | " |
| 3-5) | " | 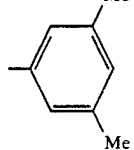 (3,5-di-Me-phenyl) | " | " |
| 3-6) | " | 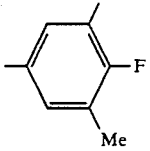 (2,6-di-Me-4-F-phenyl) | " | " |
| 3-7) | Me, Me | 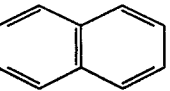 (naphthyl) | H | —CH₂— |
| 3-8) | " | 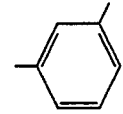 (3-Cl-phenyl) | " | " |
| 3-9) | " | 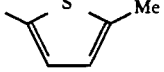 (2,5-di-Me-thienyl) | " | " |
| 3-10) | " | 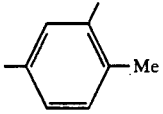 (2,5-di-Me-phenyl) | " | " |

TABLE C-continued

| Preparation No | R¹, R² | R³ | R⁴ | —A— |
|---|---|---|---|---|
| 3-11) | " | 3,4-di-Cl-phenyl | " | " |
| 3-12) | " | 3-F-phenyl | " | " |
| 3-13) | " | 2,4-di-F-phenyl | " | " |
| 3-14) | " | 2-F-5-Me-phenyl | " | " |
| 3-15) | " | 4-Cl-phenyl | " | " |
| 3-16) | " | 2-F-phenyl | " | " |
| 3-17) | " | 2,3-di-F-phenyl | " | " |
| 3-18) | " | 4-phenoxy-phenyl | " | " |
| 3-19) | " | 2,4-di-Me-phenyl | " | " |
| 3-20) | H, H | 4-F-phenyl | H | —CH₂— |

TABLE C-continued

[Structure: indole with substituents R¹, R², R³, R⁴ at positions as shown, with 6A group, CHO group, and numbered positions 1-9]

| Preparation No | R¹, R² | R³ | R⁴ | —A— |
|---|---|---|---|---|
| 3-21) | " | 2,4-difluorophenyl | " | " |
| 3-22) | " | 2,4-dimethylphenyl | " | " |
| 3-23) | " | 3,4-dichlorophenyl | " | " |
| 3-24) | " | 3-methyl-4-fluorophenyl | " | " |
| 3-25) | Me, Me | 3-methyl-4-fluorophenyl | " | " |
| 3-26) | " | 2,4,5-trifluorophenyl | " | " |
| 3-27) | " | 4-fluorophenyl | 8-Me | " |
| 3-28) | " | " | 8-Cl | " |
| 3-29) | " | " | 8-F | " |
| 3-30) | " | phenyl | H | " |
| 3-31) | " | 4-(N,N-dimethylamino)phenyl | " | " |
| 3-32) | H, H | 4-fluorophenyl | " | —O— |
| 3-33) | H, H | 4-fluorophenyl | H | —S— |
| 3-34) | Me, Me | 3-chloro-4-fluorophenyl | " | —CH₂— |
| 3-35) | " | 4-fluorophenyl | " | —CH= |
| 3-36) | H, H | 2-methoxy-4-fluorophenyl | " | —CH₂— |
| 3-37) | Me, Me | 2,6-X₂-4-hydroxyphenyl | " | " |
| 3-38) | " | 2-methoxyphenyl | " | " |
| 3-39) | " | 5-chloro-2-thienyl | " | " |

Physico-Chemical Data of Table C

| Preparation No. of Product | Data |
|---|---|
| 3-2) | IR (Film): 1675, 1605, 1120, 740 cm⁻¹<br>NMR (90MHz, CDCl₃, δ): 1.72(6H, s), 2.14 (2H, t, J=6Hz), 2.37(3H, s), 3.03(2H, t, J=6Hz), 6.16(1H, dd, J=6.9 and 15.6Hz), 6.90–7.30(7H, m), 7.76(1H, d, J=15.6Hz), 9.50(1H, d, J=6.9Hz) |
| 3-3) | mp: 121–123° C.<br>IR (Nujol): 1670, 1610, 1520 cm⁻¹<br>NMR (90MHz, CDCl₃, δ): 1.47(3H, d, J=6Hz), |

Physico-Chemical Data of Table C

| Preparation No. of Product | Data |
|---|---|
| | 2.1–2.4(2H, m), 2.9–3.3(2H, m), 4.7–5.1(1H, m), 6.58(1H, dd, J=16 and 7.0Hz), 7.0–7.7(8H, m), 9.58(1H, d, J=7Hz) |
| 3-4) | IR (Film): 2940, 1670, 1600, 1530 cm$^{-1}$<br>NMR (200MHz, CDCl$_3$, δ): 1.77(6H, s), 2.06 (3H, s), 2.17(2H, t, J=6.4Hz), 3.04(2H, t, J=6.4Hz), 5.87(1H, dd, J=7.6 and 15.8Hz), 6.9–7.4(6H, m), 7.81 (1H, d, J=15.8Hz), 9.50(1H, d, J=7.6Hz) |
| 3-5) | IR (Film): 2980, 2940, 1770, 1605, 1520 cm$^{-1}$<br>NMR (200MHz, CDCl$_3$, δ): 1.74(6H, s), 2.14 (2H, t, J=6.6Hz), 2.33(6H, s), 3.01 (2H, t, J=6.6Hz), 6.22(1H, dd, J=7.6 and 15.8Hz), 6.9–7.5(6H, m), 7.81(1H, d, J=15.8Hz), 9.54(1H, d, J=7.7Hz) |
| 3-6) | IR (Film): 2940, 1675, 1615, 1520 cm$^{-1}$<br>NMR (200MHz, CDCl$_3$, δ): 1.74(6H, s), 2.14 (2H, t, J=6.6Hz), 2.28(6H, s), 3.02 (2H, t, J=6.6Hz), 6.19(1H, dd, J=7.6 and 15.8Hz), 6.9–7.3(5H, m), 7.80(1H, d, J=15.8Hz), 9.55(1H, d, J=7.6Hz) |
| 3-7) | IR (Film): 1670, 1600 cm$^{-1}$<br>NMR (200MHz, CDCl$_3$, δ): 1.76(6H, s), 2.16 (2H, t, J=6.6Hz), 3.04(2H, t, J=6.6Hz), 6.18(1H, dd, J=7.5 and 15.8Hz), 7.0–8.0 (10H, m), 9.54(1H, d, J=7.5Hz) |
| 3-8) | IR (CH$_2$Cl$_2$): 1676, 1320, 1120, 733 cm$^{-1}$<br>NMR (CDCl$_3$, δ): 1.71(6H, s), 2.15(2H, t, J=6.6Hz), 3.02(2H, t, J=6.6Hz), 6.05 (1H, dd, J=16.5 and 6.6Hz), 6.9–7.8 (7H, m), 7.80(1H, d, J=16.5Hz), 9.57 (1H, d, J=6.6Hz) |
| 3-9) | IR (Film): 1670, 1605, 1110, 730 cm$^{-1}$<br>NMR (200MHz, CDCl$_3$, δ): 1.59(6H, s), 2.11 (2H, t, J=6Hz), 2.51(3H, s), 3.08(2H, t, J=6Hz), 6.49(1H, dd, J=8Hz, 16Hz), 7.02–7.60(6H, m), 9.50(1H, d, J=8Hz) |
| 3-10) | IR (Film): 1670, 1610, 1530, 1150, 1125, 730 cm$^{-1}$<br>NMR (200MHz, CDCl$_3$, δ): 1.74(6H, s), 2.14 (2H, t, J=6Hz), 2.25(3H, s), 2.28(3, s), 3.02(2H, t, J=6Hz), 6.24(1H, dd, J=8Hz, 16Hz), 6.99–7.30(6H, m), 7.82 (1H, d, J=16Hz), 9.54(1H, d, J=8Hz) |
| 3-11) | IR (Film): 1680, 1110, 735 cm$^{-1}$<br>NMR (200MHz, CDCl$_3$, δ): 1.73(6H, s), 2.15 (2H, t, J=6Hz), 3.03(2H, t, J=6Hz), 6.17(1H, dd, J=7Hz, 16Hz), 7.04–7.52 (7H, m), 7.81(1H, d, J=16Hz), 9.60(1H, d, J=7Hz) |
| 3-12) | IR (Nujol): 1665, 1610, 1125, 790, 745 cm$^{-1}$<br>NMR (200MHz, CDCl$_3$, δ): 1.74(6H, s), 2.15 (2H, t, J=6Hz), 3.03(2H, t, J=6Hz), 6.16(1H, dd, J=8Hz, 16Hz), 6.99–7.49 (8H, m), 7.82(1H, d, J=16Hz), 9.58(1H, d, J=8Hz) |
| 3-13) | IR (Neat): 1670, 1603, 1180, 1117, 728 cm$^{-1}$<br>NMR (CDCl$_3$, δ): 1.74(6H, s), 2.15(2H, t, J=6.4Hz), 3.03(2H, t, J=6.4Hz), 6.08 (1H, dd, J=7.6 and 15.8Hz), 6.88–7.30 (6H, m), 7.83(1H, d, J=15.8Hz), 9.59 (1H, d, J=7.6Hz) |
| 3-14) | IR (Film): 1675, 1610, 1174, 1118, 745 cm$^{-1}$<br>NMR (CDCl$_3$, δ): 1.74(6H, s), 2.15(2H, t, J=6.3Hz), 2.31(3H, s), 3.02(2H, t, J=6.3Hz), 6.17(1H, dd, J=7.6 and 15.9Hz), 6.97–7.26(6H, m), 7.81(1H, d, J=15.9Hz), 9.55(1H, d, J=7.6Hz) |
| 3-15) | IR (Film): 1675, 1603, 1521, 742 cm$^{-1}$<br>NMR (CDCl$_3$, δ): 1.74(6H, s), 2.15(2H, t, J=6.3Hz), 3.03(2H, t, J=6.3Hz), 6.17 (1H, dd, J=7.5 and 15.9Hz), 6.9–7.4(7H, m), 7.81(1H, d, J=15.9Hz), 9.57(1H, d, J=7.5Hz) |
| 3-16) | IR (Film): 1673, 1608, 1120, 746 cm$^{-1}$<br>NMR (CDCl$_3$, δ): 1.74(6H, s), 2.15(2H, t, J=6.3Hz), 3.03(2H, t, J=6.3Hz), 6.10 (1H, dd, J=7.6 and 15.9Hz), 7.02–7.43 (7H, m), 7.84(1H, d, J=15.9Hz), 9.58 (1H, d, J=7.6Hz) |
| 3-17) | IR (Film): 1675, 1603, 1537, 1120, 748 cm$^{-1}$<br>NMR (CDCl$_3$, δ): 1.74(6H, s), 2.15(2H, t, J=6.3Hz), 3.03(2H, t, J=6.3Hz), 6.13 (1H, dd, J=7.5 and 15.9Hz), 6.75–7.30 (6H, m), 7.81(1H, d, J=15.9Hz), 9.68 (1H, d, J=7.5Hz) |
| 3-18) | IR (Film): 1675, 1615, 1235, 748 cm$^{-1}$<br>NMR (CDCl$_3$, δ): 1.74(6H, s), 2.15(2H, t, J=6.3Hz), 3.02(2H, t, J=6.3Hz), 6.24 (1H, dd, J=7.6 and 15.9Hz), 6.98–7.43 (12H, m), 7.82(1H, d, J=15.9Hz), 9.56 (1H, d, J=7.6Hz) |
| 3-19) | IR (Film): 1670, 1602, 750 cm$^{-1}$<br>NMR (CDCl$_3$, δ): 1.77(6H, s), 2.04(3H, s), 2.17(2H, t, J=6.3Hz), 2.38(3H, s), 3.03(2H, t, J=6.3Hz), 5.93(1H, dd, J=7.6 and 15.7Hz), 6.93–7.19(6H, m), 7.81(1H, d, J=15.7Hz), 9.49(1H, d, J=7.6Hz) |
| 3-20) | IR (Nujol): 1685, 1670, 1610, 740 cm$^{-1}$<br>NMR (CDCl$_3$, δ): 2.29(2H, m), 3.02(2H, m), 4.36(2H, m), 6.58(1H, dd, J=7.5 and 16.2Hz), 7.0–7.6(7H, m), 9.54(1H, d, J=7.5Hz) |
| 3-21) | IR (Nujol): 1658, 1610, 1522, 1153, 1115, 741 cm$^{-1}$<br>NMR (CDCl$_3$, δ): 2.31(2H, m), 3.03(2H, t, J=6.1Hz), 4.37(2H, t, J=5.6Hz), 6.53 (1H, dd, J=7.6 and 16.3Hz), 6.97–7.48 (7H, m), 9.55(1H, d, J=7.6Hz) |
| 3-22) | IR (Nujol): 1670, 1610, 1500, 744 cm$^{-1}$<br>NMR (CDCl$_3$, δ): 3.02(2H, t, J=6.1Hz), 2.31 (2H, m), 2.35(6H, s), 4.37(2H, t, J=5.8Hz), 6.60(1H, dd, J=7.7 and 16.3Hz) 7.00–7.66(7H, m), 9.54(1H, d, J=7.7Hz) |
| 3-23) | IR (Nujol): 1673, 1612, 745 cm$^{-1}$<br>NMR (CDCl$_3$, δ): 2.31(2H, m), 3.04(2H, t, J=6.1Hz), 4.38(2H, t, J=5.8Hz), 6.61 (1H, dd, J=7.6 and 16.3Hz), 7.08–7.59 (7H, m), 9.58(1H, d, J=7.6Hz) |
| 3-24) | mp: 140–141° C.<br>IR (Nujol): 1683, 1670, 1613, 1143, 1111, 740 cm$^{-1}$<br>NMR (CDCl$_3$, δ): 2.26(2H, m), 2.35(3H, s), 3.03(2H, t, J=6.1Hz), 4.37(2H, t, J=5.8Hz), 6.59(1H, dd, J=7.6 and 16.3Hz), 7.01–7.60(7H, m), 9.55(1H, d, J=7.6Hz) |
| 3-25) | IR (Film): 1670, 1600, 1530, 1280, 1150, 1120, 735 cm$^{-1}$<br>NMR (200MHz, CDCl$_3$, δ): 1.72(3H, s), 1.77 (3H, s), 2.15(2H, t, J=6Hz), 3.02(2H, t, J=6Hz), 3.70(3H, s), 6.07(1H, quartet, J=8Hz), 6.7–7.25(6H, m), 7.80 (1H, d, J=16Hz), 9.54(1H, d, J=8Hz) |
| 3-26) | IR (Film): 1670, 1600, 1120, 730 cm$^{-1}$<br>NMR (200MHz, CDCl$_3$, δ): 1.59(3H, s), 1.74 (3H, s), 2.16(2H, t, J=6Hz), 3.04(2H, t, J=6Hz), 6.08(1H, quartet, J=8Hz), 6.7–7.6(6H, m), 7.83(1H, d, J=16Hz), 9.62(1H, d, J=8Hz) |
| 3-27) | NMR (CDCl$_3$, δ): 1.70(6H, s), 2.10(2H, t, J=6Hz), 2.35(3H, s), 2.95(2H, t, J=6Hz), 6.08(1H, dd, J=16.8 and 9.0Hz), 6.8–7.5(6H, m), 7.80(1H, d, J=16.8Hz), 9.50(1H, d, J=9.0Hz) |
| 3-28) | NMR (CDCl$_3$, δ): 1.72(6H, s), 2.13(2H, t, J=8Hz), 3.00(2H, t, J=8Hz), 6.13(1H, dd, J=6 and 17Hz), 7.0–7.3(6H, m), 7.76 (1H, d, J=17Hz), 9.56(1H, d, J=6Hz) |
| 3-29) | NMR (CDCl$_3$, δ): 1.73(6H, s), 2.14(2H, t, J=6Hz), 3.00(2H, t, J=6Hz), 6.12(1H, dd, J=15 and 8Hz), 6.7–7.5(6H, m), 7.78 (1H, d, J=15Hz), 9.56(1H, d, J=8Hz) |
| 3-30) | IR (Nujol): 1664, 1620, 1130, 745 cm$^{-1}$ |

Physico-Chemical Data of Table C -continued

| Preparation No. of Product | Data |
|---|---|
| | NMR (CDCl₃, δ): 1.74(6H, s), 2.15(2H, t, J=6.3Hz), 3.03(2H, t, J=6.3Hz), 6.17 (1H, dd, J=7.6 and 15.9Hz), 7.01-7.47 (8H, m), 7.82(1H, d, J=15.8Hz), 9.54 (1H, d, J=7.6Hz) |
| 3-31) | IR (Nujol): 1679, 1610, 1121, 745 cm⁻¹ NMR (CDCl₃, δ): 1.74(6H, s), 2.13(2H, t, J=6.3Hz), 3.01(8H, m), 6.35(1H, dd, J=7.7 and 15.8Hz), 6.72-7.35(7H, m), 7.82(1H, d, J=15.8Hz), 9.54(1H, d, J=7.7Hz) |
| 3-32) | mp: 165-170° C. IR (Nujol): 1670, 1610, 1500 cm⁻¹ NMR (CDCl₃, δ): 4.4-4.7(4H, m), 6.56(1H, dd, J=7.6 and 17.2Hz), 6.18(1H, d, J=7.5Hz), 6.9-7.6(7H, m), 9.56(1H, d, J=7.6Hz) |
| 3-33) | mp: 177-179° C. IR (Nujol): 1675, 1610, 1520 cm⁻¹ NMR (CDCl₃, δ): 3.28(2H, t, J=5Hz), 4.62 (2H, t, J=5Hz), 6.47(1H, dd, J=7 and 16Hz), 6.95-7.65(8H, m), 9.56(1H, d, J=7Hz) |
| 3-34) | IR (Neat): 1670, 1600, 1244, 743 cm⁻¹ NMR (CDCl₃, δ): 1.73(3H, s), 1.76(3H, s), 2.17(2H, t, J=7.1Hz), 3.04(2H, t, J=6.3Hz), 5.91(1H, dd, J=7.6 and 15.8Hz), 7.03-7.57(6H, m), 7.80(1H, d, J=15.8Hz), 9.56(1H, d, J=7.6Hz) |
| 3-35) | IR (Film): 1675, 1535, 1120, 745 cm⁻¹ NMR (CDCl₃, δ): 1.84(6H, s), 5.66(1H, d, J=9.9Hz), 6.17(1H, dd, J=7.5 and 15.8Hz), 6.55(1H, d, J=9.9Hz), 6.83-7.41(7H, m), 7.84(1H, d, J=15.8Hz), 9.54(1H, d, J=7.5Hz) |
| 3-36) | mp: 170-173.5° C. IR (Nujol): 1680, 1620, 1276, 740 cm⁻¹ NMR (CDCl₃, δ): 2.31(2H, quint, J=6.0Hz), 3.02(2H, t, J=6.1Hz), 3.76(3H, s), 4.37(2H, t, J=5.8Hz), 6.49(1H, dd, J=7.6 and 16.3Hz), 6.74-6.83(2H, m), 6.97-7.05(2H, m), 7.16-7.29(2H, m), 7.43(1H, d, J=16.3Hz), 9.51(1H, d, J=7.6Hz) |
| 3-37) | IR (Neat): 3650, 2960, 1670, 1600 cm⁻¹ NMR (CDCl₃, δ): 1.45(18H, s), 1.75(6H, s), 2.14(2H, t, J=6.0Hz), 3.02(2H, t, J=6.0Hz), 5.24(1H, s), 6.32(1H, dd, J=7.7 and 15.9Hz), 7.0-7.5(5H, m), 7.82 (1H, d, J=15.9Hz), 9.57(1H, d, J=7.7Hz) MASS m/z: 443 |
| 3-38) | IR (Neat): 2980, 1670, 1600 cm⁻¹ NMR (CDCl₃, δ): 1.59(6H, s), 2.13(2H, t, J=6.2Hz), 3.06(2H, t, J=6.2Hz), 3.81(3H, s), 6.22(1H, dd, J=7.6 and 15.8Hz), 6.9-8.0(8H, m), 9.55 (1H, d, J=7.6Hz) |
| 3-39) | IR (Nujol): 2980, 2940, 1670, 1610, 1535 cm⁻¹ NMR (CDCl₃, δ): 1.59(6H, s), 2.12(2H, t, J=6.2Hz), 3.08(2H, t, J=6.2Hz), 6.46 (1H, dd, J=7.8 and 15.8Hz), 7.0-7.7(6H, m), 9.51(1H, d, J=7.8Hz) |

Preparation 4-1)

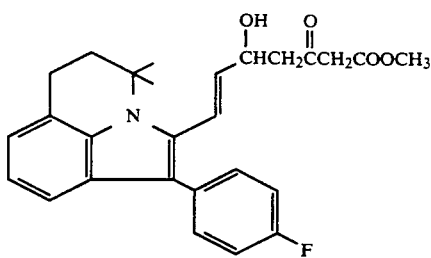

60% Sodium hydride/mineral oil (0.63 g) was washed twice with n-hexane (3 ml×2) and the remaining powdered sodium hydride was suspended in dry tetrahydrofuran (24 ml). The suspension was cooled to −20° C. under nitrogen. A tetrahydrofuran (8 ml) was dropwise added with stirring at −20° to −15° C. under nitrogen to the suspension. The reaction mixture was stirred at −20° to −15° C. for 30 minutes and 1.6 M n-butyllithium/hexane (8.6 ml) was dropwise added thereto with stirring at −20° to −15° C. for 30 minutes. A solution of (E)-3-[5,6-dihydro-4,4-dimethyl-1-(4-fluorophenyl)-4H-pyrrolo[3,2,1-ij]quinolin-2-yl]acrylaldehyde (3.07 g) in dry tetrahydrofuran was dropwise added to the mixture over a 30-minute period at −20° to −15° C. under nitrogen. The reaction mixture was stirred at −20° to −15° C. for 1 hour and quenched at −0° to 0° C. with saturated aqueous ammonium chloride. The tetrahydrofuran was evaporated under reduced pressure and the residue was extracted with ethyl acetate. The extract was washed with saturated aqueous sodium chloride solution, dried over anhydrous magnesium sulfate, filtered and evaporated under reduced pressure. The residue was chromatographed on "florisil" (trademark, made by floridin Company) (120 g) eluting with a mixture of n-hexane and ethyl acetate (5:2, V/V). The fractions containing the object compound were combined and concentrated under reduced pressure to give yellow syrup of methyl (E)-7-[5,6-dihydro-4,4-dimethyl-1-(4-fluorophenyl)-4H-pyrrolo[3,2,1-ij]quinolin-2-yl]-5-hydroxy-3-oxohept-6-enoate (2.60 g).

IR (Neat) : 3500, 2900, 1740, 1720, 1535, 1440, 1230, 1155, 830, 745 cm⁻¹.

NMR (CDCl₃, δ): 1.63 (6H, s), 2.10 (2H, t, J=6Hz) 2.59 (2H, d, J=6Hz), 2.84 (1H, d, J=4Hz), 3.00 (2H, t, J=6Hz), 3.44 (2H, s), 3.75 (3H, s), 4.60-4.68 (1H, m), 5.52 (1H, dd, J=5 and 16Hz), 6.87 (1H, dd, J=1.5 and 16Hz), 6.9-7.4 (7H, m).

The compounds of Table D were obtained in substantially the same manner as that of Preparation 4-1).

TABLE D
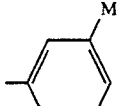
| Preparation | R¹, R² | R³ | R⁴ | R⁵ | —A— |
|---|---|---|---|---|---|
| 4-2) | Me, Me |  Me | H | COOMe | —CH₂— |
| 4-3) | H, Me |  F | " | " | " |
| 4-4) | Me, Me | 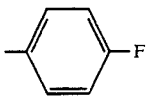 F, Me | " | " | " |
| 4-5) | " | 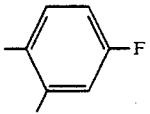 Me, Me | " | " | " |
| 4-6) | " | 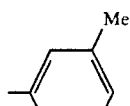 Me, F, Me | " | " | " |
| 4-7) | Me, Me | 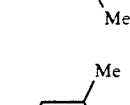 | " | " | " |
| 4-8) | " | 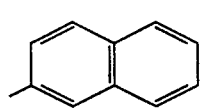 Cl | " | " | " |
| 4-9) | " | 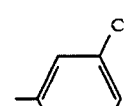 S, Me | " | " | " |
| 4-10) | " | 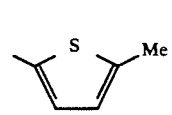 Me, Me | " | " | " |

TABLE D-continued
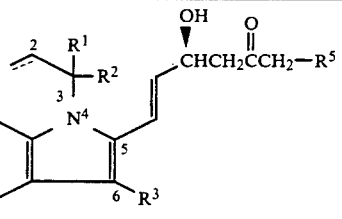
| Preparation | R¹, R² | R³ | R⁴ | R⁵ | —A— |
|---|---|---|---|---|---|
| 4-11) | " | 3,4-diCl-phenyl | " | " | " |
| 4-12) | " | 3-F-phenyl | " | " | " |
| 4-13) | " | 2,4-diF-phenyl | " | " | " |
| 4-14) | Me, Me | 3-Me-4-F-phenyl | H | COOMe | —CH$_2$— |
| 4-15) | " | 4-Cl-phenyl | " | " | " |
| 4-16) | " | 2-F-phenyl | " | " | " |
| 4-17) | " | 3,4-diF-phenyl | " | " | " |
| 4-18) | " | 4-phenoxyphenyl | " | " | " |
| 4-19) | " | 2,5-diMe-phenyl | " | " | " |
| 4-20) | H, H | 4-F-phenyl | " | " | " |

TABLE D-continued
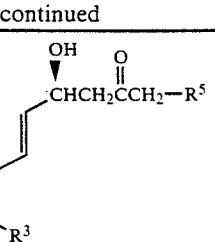
| Preparation | R¹, R² | R³ | R⁴ | R⁵ | —A— |
|---|---|---|---|---|---|
| 4-21) | " | 2,4-diF-phenyl | " | " | " |
| 4-22) | " | 2,4-diMe-phenyl | " | " | " |
| 4-23) | " | 3,4-diCl-phenyl | " | " | " |
| 4-24) | " | 3-Me-4-F-phenyl | " | " | " |
| 4-25) | Me, Me | 3-MeO-4-F-phenyl | " | " | " |
| 4-26) | " | 2,4,6-triF-phenyl | " | " | " |
| 4-27) | Me, Me | 4-F-phenyl | 8-Me | COOMe | —CH₂— |
| 4-28) | " | " | 8-Cl | " | " |
| 4-29) | " | " | 8-F | " | " |
| 4-30) | " | phenyl | H | " | " |
| 4-31) | " | 4-NMe₂-phenyl | " | " | " |

TABLE D-continued

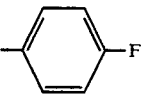

| Preparation | R¹, R² | R³ | R⁴ | R⁵ | —A— |
|---|---|---|---|---|---|
| 4-32) | H, H | 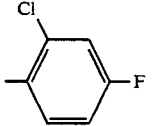 (4-F-phenyl) | " | " | —O— |
| 4-33) | " | " | " | " | —S— |
| 4-34) | Me, Me | 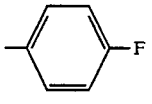 (3-Cl, 4-F-phenyl) | " | " | —CH₂— |
| 4-35) | " | 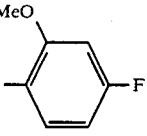 (4-F-phenyl) | " | " | —CH= |
| 4-36) | H, H | 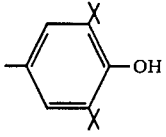 (2-MeO, 4-F-phenyl) | " | " | —CH₂— |
| 4-37) | Me, Me | 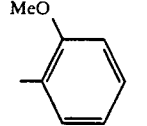 (OH, with X groups) | " | " | " |
| 4-38) | " | 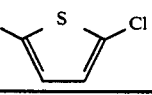 (2-MeO-phenyl) | " | " | " |
| 4-39) | " | (5-Cl-thiophen-2-yl) | " | " | " |

| | Physico-Chemical Data of Table D |
|---|---|
| Preparation No. of Product | Data |
| 4-2) | IR (Film): 3490, 1738, 1720, 1605, 1042, 746 cm⁻¹<br>NMR (200MHz, CDCl₃, δ): 1.63(6H, s), 2.10 (2H, t, J=6.4Hz), 2.38(3H, s), 2.57 (2H, d, J=6.1Hz), 2.74(1H, d, J=4.0Hz), 3.00(2H, t, J=6.3Hz), 3.42(2H, s), 3.75(3H, s), 4.95(1H, m), 5.54(1H, dd, J=5.5 and 15.8Hz), 6.88(1H, d, J=15.8Hz), 6.95–7.39(7H, m) |
| 4-3) | IR (Film): 3450, 2950, 1745, 1710, 1640, 1530, 1500 cm⁻¹<br>NMR (200MHz, CDCl₃, δ): 1.38(3H, d, J=6.6Hz), 2.1–2.3(2H, m), 2.76(2H, d, J=6.0Hz), 2.84(1H, br s), 2.9–3.2(2H, m), 3.49(2H, s), 3.74(3H, s), 4.6–4.9 (2H, m), 5.96(1H, dd, J=5.7 and 16.2Hz), 6.74(1H, d, J=16.2Hz), 6.9–7.5 (7H, m) |
| 4-4) | IR (Film): 3460, 2940, 1745, 1710, 1610, 1535 cm⁻¹<br>NMR (200MHz, CDCl₃, δ): 1.64(6H, s), 2.0–2.2(5H, m), 3.02(2H, t, J=6.2Hz), 3.41(2H, s), 3.75(3H, s), 4.5–4.6 (1H, m), 5.30(1H, dd, J=5.4 and 15.7Hz), 6.84(1H, d, J=15.7Hz), 6.9–7.3 (6H, m) |
| 4-5) | IR (Film): 3500, 2940, 1740, 1710, 1600 cm⁻¹<br>NMR (200MHz, CDCl₃, δ): 1.62(6H, s), 2.09 |

Physico-Chemical Data of Table D

| Preparation No. of Product | Data |
|---|---|
| | (2H, t, J=6.1Hz), 2.34(6H, s), 2.57 (2H, d, J=5.6Hz), 2.74(1H, d, J=3.9Hz), 3.00(2H, t, J=6.1Hz), 3.43(2H, s), 3.74(3H, s), 4.66(1H, m), 5.56(1H, dd, J=5.5 and 15.8Hz), 6.8–7.4(7H, m) |
| 4-6) | IR (Film): 3450, 2940, 1740, 1710 cm$^{-1}$ NMR (200MHz, CDCl$_3$, δ): 1.62(6H, s), 2.09 (2H, t, J=6.1Hz), 2.29(6H, s), 2.58 (2H, d, J=6.0Hz), 2.78(1H, d, J=3.9Hz), 3.00(2H, t, J=6.1Hz), 3.44(2H, s), 3.74(3H, s), 4.66(1H, m), 5.55 (1H, dd, J=5.4 and 15.8Hz), 6.86(1H, dd, J=1.5 and 15.8Hz), 6.9–7.1(4H, m), 7.32(1H, d, J=6.4Hz) |
| 4-7) | IR (Film): 3500, 2980, 2940, 1745, 1715, 1630, 1600, 1530 cm$^{-1}$ NMR (200MHz, CDCl$_3$, δ): 1.66(6H, s), 2.12 (2H, t, J=6.4Hz), 2.44(2H, d, J=5.4Hz), 2.76(1H, d, J=4.1Hz), 3.02(2H, t, J=6.4Hz), 3.25(2H, s), 3.68(3H, s), 4.59(1H, m), 5.52(1H, dd, J=5.3 and 15.8Hz), 6.9–8.0(11H, m) |
| 4-8) | IR (CH$_2$Cl$_2$): 1745, 1712, 1320, 730 cm$^{-1}$ NMR (CDCl$_3$, δ): 1.63(6H, s), 2.11(2H, m), 2.55(2H, d, J=6Hz), 2.86(1H, d, J=4Hz), 3.01(2H, m), 3.46(2H, s), 3.73 (3H, s), 4.66(1H, m), 5.51(1H, dd, J=15 and 6Hz), 6.8–7.6(8H, m) |
| 4-9) | IR (Film): 3500, 1745, 1715, 1440, 1180, 730 cm$^{-1}$ NMR (200MHz, CDCl$_3$, δ): 1.57(6H, s), 2.09 (2H, t, J=6Hz), 2.27(1H, s), 2.48(3H, s), 2.54–2.83(2H, m), 3.05(2H, t, J=6Hz), 3.48(2H, s), 3.71(3H, s), 4.66 (1H, m), 5.98(1H, dd, J=7Hz, 16Hz), 6.68(1H, d, J=16Hz), 6.93–7.53(5H, m) |
| 4-10) | IR (Film): 3505, 1745, 1715, 1440, 730 cm$^{-1}$ NMR (200MHz, CDCl$_3$, δ): 1.62(6H, s), 2.09 (2H, t, J=6Hz), 2.27(1H, s), 2.29(3H, s), 2.30(3H, s), 2.58–2.72(2H, m), 3.00(2H, t, J=6Hz), 3.42(2H, s), 3.74 (3H, s), 4.65(1H, m), 5.57(1H, dd, J=6Hz, 16Hz), 6.86(1H, dd, J=1Hz, 16Hz), 6.90–7.39(6H, m) |
| 4-11) | IR (Film): 3500, 1740, 1715, 1440, 735 cm$^{-1}$ NMR (200MHz, CDCl$_3$, δ): 1.62(6H, s), 2.10 (2H, t, J=6Hz), 2.63–2.96(2H, m), 3.00 (2H, t, J=6Hz), 3.47(2H, s), 3.73(1H, s), 3.76(3H, s), 4.69(1H, m), 5.56 (1H, dd, J=5Hz, 16Hz), 6.89(1H, dd, J=2Hz and J=16Hz), 6.9–7.08(2H, m), 7.29–7.53(4H, m) |
| 4-12) | IR (Film): 3500, 1740, 1710, 1610, 1580, 1440, 1150, 730 cm$^{-1}$ NMR (200MHz, CDCl$_3$, δ): 1.63(6H, s), 2.10 (2H, t, J=6Hz), 2.27(1H, s), 2.61(2H, d, J=6Hz), 2.85(1H, d, J=4Hz), 3.01 (2H, t, J=6Hz), 3.45(2H, s), 3.75(3H, s), 4.67(1H, m), 5.55(1H, dd, J=5Hz and J=16Hz), 6.84–7.40(8H, m) |
| 4-13) | IR (Film): 3450, 1740, 1710, 1155, 1135, 744 cm$^{-1}$ NMR (CDCl$_3$, δ): 1.63(6H, s), 2.11(2H, t, J=6.3Hz), 2.59(2H, d, J=6.0Hz), 2.8 (1H, d, J=4.0Hz), 3.01(2H, t, J=6.3Hz), 3.46(2H, s), 3.75(3H, s), 4.65(1H, m), 5.50(1H, dd, J=5.5Hz and 15.8Hz), 6.84–7.45(7H, m) |
| 4-14) | IR (Film): 3450, 1743, 1712, 1174, 1116, 745 cm$^{-1}$ NMR (CDCl$_3$, δ): 1.62(6H, s), 2.10(2H, m), 2.30(3H, s), 2.59(2H, d, J=6.0Hz), 2.81(1H, d, J=4.0Hz), 3.00(2H, m), 3.44(2H, s), 3.75(3H, s), 4.65(1H, m), 5.53(1H, dd, J=5.3Hz and 15.8Hz), 6.82–7.34(7H, m) |
| 4-15) | IR (Film): 3450, 1744, 1712, 1525, 743 cm$^{-1}$ NMR (CDCl$_3$, δ): 1.62(6H, s), 2.10(2H, t, J=6.3Hz), 2.61(2H, d, J=6.0Hz), 2.85 (1H, d, J=4.2Hz), 3.00(2H, t, J=6.3Hz), 3.44(2H, s), 3.75(3H, s), 4.65(1H, m), 5.53(1H, dd, J=5.1 and 15.8Hz), 6.84–7.43(8H, m) |
| 4-16) | IR (Film): 3450, 1743, 1715, 1670, 1154, 745 cm$^{-1}$ NMR (CDCl$_3$, δ): 1.64(6H, s), 2.12(2H, m), 2.55(2H, d, J=6.0Hz), 2.70(1H, d, J=3.9Hz), 3.01(2H, t, J=5.8Hz), 3.43 (2H, s), 3.74(3H, s), 4.64(1H, m), 5.50(1H, dd, J=5.6Hz and 15.8Hz), 6.86–7.43(8H, m) |
| 4-17) | IR (Film): 3450, 1745, 1712, 1185, 745 cm$^{-1}$ NMR (CDCl$_3$, δ): 1.62(6H, s), 2.07–2.27 (4H, m), 2.63(1H, m), 3.01(2H, m), 3.46(2H, s), 3.75(3H, s), 4.68(1H, m), 5.55(1H, dd, J=5.1 and 15.8Hz), 6.92–7.35(7H, m) |
| 4-18) | IR (Film): 3500, 1746, 1714, 1235, 748 cm$^{-1}$ NMR (CDCl$_3$, δ): 1.63(6H, s), 2.10(2H, t, J=6.3Hz), 2.61(2H, d, J=6.0Hz), 2.78 (1H, d, J=4.0Hz), 3.00(2H, t, J=6.0Hz), 3.44(2H, s), 3.73(3H, s), 4.67(1H, m), 5.58(1H, dd, J=5.4Hz and 15.8Hz), 6.84–7.41(13H, m) |
| 4-19) | IR (Film): 3500, 1745, 1713, 748 cm$^{-1}$ NMR (CDCl$_3$, δ): 1.64(6H, s), 2.03–2.15 (5H, m), 2.37(3H, s), 2.45(2H, m), 2.63(1H, m), 3.01(2H, t, J=6.2Hz), 3.38(2H, s), 3.74(3H, s), 4.56(1H, m), 5.34(1H, dd, J=5.6Hz and 15.7Hz), 6.80–7.25(7H, m) |
| 4-20) | IR (Neat): 3500(br), 1700–1760(br), 745 cm$^{-1}$ NMR (CDCl$_3$, δ): 2.24(2H, m), 2.81(1H, d, J=5.8Hz), 2.88(1H, d, J=4Hz), 2.96(2H, t, J=6Hz), 3.50(2H, s), 3.73(3H, s), 4.24(2H, t, J=6Hz), 4.72(1H, m), 5.99 (1H, dd, J=6Hz and 16Hz), 6.72(1H, d, J=16Hz), 6.9–7.2(4H, m), 7.3–7.5(3H, m) |
| 4-21) | IR (Neat): 3495, 1745, 1712, 1610, 1138, 743, 730 cm$^{-1}$ NMR (CDCl$_3$, δ): 2.27(2H, m), 2.80(3H, m), 3.00(2H, t, J=6.0Hz), 3.49(2H, s), 3.74(3H, s), 4.24(2H, t, J=5.8Hz), 4.71(1H, m), 5.93(1H, dd, J=6.0Hz and 16.3Hz), 6.67(1H, d, J=16.3Hz), 6.89–7.43(6H, m) |
| 4-22) | IR (Neat): 3470, 1743, 1713, 1610, 729 cm$^{-1}$ NMR (CDCl$_3$, δ): 2.24(2H, m), 2.32(6H, s), 2.76–2.84(3H, m), 2.99(2H, t, J=6Hz), 3.50(2H, s), 3.73(3H, s), 4.26(2H, t, J=5.8Hz), 4.72(1H, m), 6.03(1H, dd, J=6.2Hz and 16.4Hz), 6.77(1H, d, J=16.4Hz), 6.92–7.47(6H, m) |
| 4-23) | IR (Neat): 3490, 1742, 1711, 743, 728 cm$^{-1}$ NMR (CDCl$_3$, δ): 2.25(2H, m), 2.83(2H, d, J=6Hz), 2.92(1H, d, J=4Hz), 3.0(2H, t, J=6Hz), 3.52(2H, s), 3.74(3H, s), 4.23 (2H, t, J=5.8Hz), 6.02(1H, dd, J=5.7Hz and 16.3Hz), 6.72(1H, d, J=16.13Hz), 6.95–7.60(6H, m) |
| 4-24) | IR (Neat): 3450, 1740, 1710, 1650, 1165, 1115, 742 cm$^{-1}$ NMR (DMSO-d$_6$, δ): 2.25(2H, m), 2.33(3H, s), 2.81(2H, d, J=6Hz), 3.00(2H, t, J=6Hz), 3.50(2H, s), 3.74(3H, s), 4.25 (2H, t, J=5.8Hz), 4.73(1H, m), 6.00 (1H, dd, J=6.0Hz and 16.4Hz), 6.73(1H, d, J=16.4Hz), 6.93–7.41(6H, m) |
| 4-25) | IR (Film): 3450, 1745, 1720, 740 cm$^{-1}$ NMR (200MHz, CDCl$_3$, δ): 1.63(6H, broad s), 2.10(2H, broad t, J=ca. 6Hz), 2.51–2.68 (2H, m), 3.00(2H, t, J=6Hz), 3.42(2H, s), 3.75(3H, s), 4.60(1H, m), 5.45 (1H, dd, J=6Hz, 16Hz), 6.7–7.2(7H, m) |
| 4-26) | IR (Film): 3450, 1740, 1720, 1440, 735 cm$^{-1}$ NMR (200MHz, CDCl$_3$, δ): 1.63(6H, s), 2.11 |

| Preparation No. of Product | Physico-Chemical Data of Table D - Data |
|---|---|
| | (2H, t, J=6Hz), 2.59(2H, d, J=6Hz), 3.00(2H, t, J=6Hz), 3.45(2H, s), 3.75 (3H, s), 4.66(1H, m), 5.54(1H, dd, J=5Hz and 16Hz), 6.8-7.4(6H, m) |
| 4-27) | IR (Film): 3450, 1740, 1710, 837, 750 cm$^{-1}$ NMR (CDCl$_3$, δ): 1.73(6H, s), 2.08(2H, t, J=6.3Hz), 2.39(3H, s), 2.59(2H, d, J=6.0Hz), 2.78(1H, m), 2.96(2H, t, J=6.2Hz), 3.44(2H, s), 3.75(3H, s), 4.64(1H, m), 5.50(1H, dd, J=5.3 and 15.8Hz), 6.80-7.40(7H, m) |
| 4-28) | NMR (CDCl$_3$, δ): 1.57(3H, s), 1.63(3H, s), 2.11(2H, t, J=6Hz), 2.58(2H, d, J=6Hz), 2.80(1H, d, J=3.6Hz), 2.96(2H, t, J=6Hz), 3.40(2H, s), 3.72(3H, s), 4.60(1H, m), 5.50(1H, dd, J=16Hz and 5.7Hz), 6.6-7.5(7H, m) |
| 4-29) | NMR (CDCl$_3$, δ): 1.61(6H, s), 2.09(2H, t, J=6Hz), 2.58(2H, d, J=6Hz), 2.86(1H, d, J=4Hz), 2.97(2H, t, J=6Hz), 3.44 (2H, s), 3.74(3H, s), 4.64(1H, m), 5.51(1H, dd, J=16Hz and 6Hz), 6.6-7.4 (7H, m) |
| 4-30) | IR (Film): 3500, 1740, 1710, 1602, 745 cm$^{-1}$ NMR (CDCl$_3$, δ): 1.63(6H, s), 2.10(2H, t, J=6.3Hz), 2.56(2H, d, J=5.9Hz), 2.76 (1H, d, J=4.0Hz), 3.00(2H, t, J=6.3Hz), 3.42(2H, s), 3.74(3H, s), 4.63(1H, m), 5.52(1H, dd, J=5.4 and 15.8Hz), 6.87(1H, d, J=15.9Hz), 6.96-7.44(8H, m) |
| 4-31) | mp: 128-130° C. IR (Nujol): 3500, 1747, 1716, 1150, 742 cm$^{-1}$ NMR (CDCl$_3$, δ): 1.62(6H, s), 2.09(2H, t, J=6.4Hz), 2.63(2H, d, J=6.0Hz), 2.67 (1H, d, J=4.1Hz), 2.98(8H, m), 3.43 (2H, s), 3.73(3H, s), 4.65(1H, br), 5.61(1H, dd, J=5.5Hz and 15.8Hz), 6.77-7.02(4H, m), 7.25-7.39(3H, m) |
| 4-32) | IR (Neat): 3500, 2950, 1745, 1715, 1630 cm$^{-1}$ NMR (CDCl$_3$, δ): 2.8-2.9(3H, m), 3.47(2H, s), 3.74(3H, s), 4.3-4.6(4H, m), 4.7-4.8(1H, m), 6.03(1H, dd, J=5.9 and 16.4Hz), 6.73(1H, d, J=16.4Hz), 6.70 (1H, d, J=7.6Hz), 7.03(1H, t, J=7.6Hz), 7.1-7.5(5H, m) |
| 4-33) | IR (Neat): 3450, 2950, 1740, 1710, 1640, 1530 cm$^{-1}$ NMR (CDCl$_3$, δ): 2.80(2H, d, J=6.0Hz), 2.94 (1H, d, J=4.0Hz), 3.26(2H, t, J=5.2Hz), 3.49(2H, s), 3.74(3H, s), 4.51(2H, t, J=5.2Hz), 5.91(1H, dd, J=5.6 and 16.3Hz), 6.71(1H, dd, J=1.5 and 16.3Hz), 7.0-7.5(7H, m) |
| 4-34) | IR (Film): 3450, 1745, 1711, 1604, 1153, 745 cm$^{-1}$ NMR (CDCl$_3$, δ): 1.62(6H, s), 2.12(2H, br), 2.52(2H, d, J=6.0Hz), 2.72(1H, m), 3.01(2H, m), 3.43(2H, s), 3.75(3H, s), 4.60(1H, br), 5.38(1H, dd, J=5.4Hz and 15.7Hz), 6.80-7.46(7H, m) |
| 4-35) | IR (Neat): 3475, 1742, 1712, 1643, 1219, 742 cm$^{-1}$ NMR (CDCl$_3$, δ): 1.74(6H, s), 2.59(2H, d, J=6.0Hz), 2.83(1H, d, J=4.1Hz), 3.44 (2H, s), 3.75(3H, s), 4.63(1H, m), 5.56(1H, dd, J=5.3Hz and 15.9Hz), 5.58 (1H, d, J=9.8Hz), 6.50(1H, d, J=9.8Hz), 6.76-7.43(8H, m) |
| 4-36) | IR (Nujol): 3500, 1742, 1710, 1602, 1150, 745 cm$^{-1}$ NMR (CDCl$_3$, δ): 2.27(3H, m), 2.75(2H, d, J=5.9Hz), 2.99(2H, t, J=5.9Hz), 3.48 (2H, s), 3.73(3H, s), 3.76(3H, s), 4.24(2H, t, J=5.7Hz), 4.67(1H, br), 5.89(1H, dd, J=6.1Hz and 16.3Hz), 6.64 (1H, d, J=16.4Hz), 6.72-7.28(6H, m) |
| 4-37) | IR (Neat): 3650, 3500, 2950, 1745, 1710, 1640, 1530 cm$^{-1}$ |
| | NMR (CDCl$_3$, δ): 1.46(18H, s), 1.63(6H, s), 2.10(2H, t, J=6.6Hz), 2.5-2.8(2H, m), 3.00(2H, t, J=6.6Hz), 3.42(2H, s), 3.72(3H, s), 4.65(1H, m), 5.12(1H, s), 5.62(1H, dd, J=5.4 and 15.8Hz), 6.9-7.1(2H, m), 7.22(2H, s), 7.35(1H, d, J=7.6Hz) |
| 4-38) | IR (Neat): 3400, 2950, 1740, 1710, 1600 cm$^{-1}$ |
| 4-39) | IR (Neat): 3450, 2940, 1740, 1710, 1640, 1545 cm$^{-1}$ NMR (CDCl$_3$, δ): 1.57(6H, s), 2.09(2H, t, J=7.5Hz), 2.63(1H, d, J=3.9Hz), 2.7-3.0 (2H, m), 3.05(2H, t, J=7.5Hz), 3.47 (2H, s), 3.72(3H, s), 4.66(1H, m), 5.98(1H, dd, J=6.5Hz and 16.0Hz), 6.65 (1H, d, J=16.0Hz), 6.9-7.6(5H, m) |

EXAMPLE 1-1

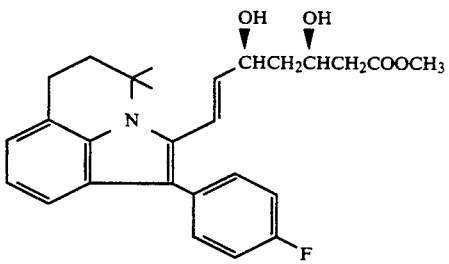

A mixture of 1M triethylborane/n-hexane (12.0 ml) and pivalic acid (0.06 g) was stirred at room temperature for 2 hours under nitrogen. A solution of methyl (E)-7-[5,6-dihydro-4,4-dimethyl-1-(4-fluorophenyl)-4H-pyrrolo[3,2,1-ij]quinolin 2-yl]-5-hydroxy-3-oxohept-6-enoate (2.57 g) in dry tetrahydrofuran (25 ml) was added to the mixture. After 2 hours, the reaction mixture was cooled to −78° C. and methanol (12 ml) was added dropwise thereto. Sodium borohydride (0.54 g) was carefully added by portions at -75 to −70° C. under nitrogen to the reaction mixture. After being stirred at the same temperature for 1 hour, the reaction mixture was quenched at −10° C. to 0° C. with 0.5 M aqueous citric acid, warmed to room temperature and extracted with diethyl ether. The extract was washed with saturated aqueous sodium chloride, dried over anhydrous magnesium sulfate and evaporated under reduced pressure. The residue was dissolved in methanol (30 ml) warmed to 40 to 45° C. and evaporated under reduced pressure. After this procedure was repeated two more times, the residue was chromatographed on a silica gel column eluting with a mixture of n-hexane and ethyl acetate (2:1, V/V). The fractions containing the object compound were collected and concentrated under reduced pressure to give white crystals of methyl (±)-erythro-(E)-7-[5,6-dihydro-4,4-dimethyl-1-(4-fluorophenyl)-4H-pyrrolo[3,2,1-ij]quinolin-2-yl]-3,5-dihydroxyhept-6-enoate (1.84 g).

mp: 108.5°-109.5° C.

IR (Nujol): 3500, 3450, 1740, 1440, 1210 cm$^{-1}$.

NMR (CDCl$_3$, δ): 1.38-1.6 (2H, m), 1.64 (6H, s), 2.10 (2H, t, J=6Hz), 2.45 (2H, d, J=6Hz), 3.00 (2H, t, J=6Hz), 3.36 (1H, br s), 3.66 (1H, d, J=4Hz), 3.73 (3H, s), 4.1-4.2 (1H, m), 4.4-4.5 (1H, m), 5.56 (1H, dd, J=6 and 16Hz), 6.85 (1H, dd, J=1.5Hz and 16Hz), 6.9-7.4 (7H, m).

The compounds of Table 1 were obtained in substantially the same manner as that of Example 1-1).

TABLE 1

[Structure: indole with positions labeled 1-9, substituents R¹, R² at position 4, R³ at position 1/2, R⁴ at position 7/8, A at position 6, and a side chain CH=CH-CHCH₂CHCH₂-R⁵ with two OH groups]

| Example No. | R¹, R² | R³ | R⁴ | R⁵ | —A— |
|---|---|---|---|---|---|
| 1-2) | Me, Me | 3-Me-phenyl | H | COOMe | —CH₂— |
| 1-3) | H, Me | 4-F-phenyl | " | " | " |
| 1-4) | Me, Me | 4-F-3-Me-phenyl | " | " | " |
| 1-5) | " | 3,5-diMe-phenyl | " | " | " |
| 1-6) | " | 3-F-2,6-diMe-phenyl | " | " | " |
| 1-7) | " | naphthyl | " | " | " |
| 1-8) | " | 3-CF₃-phenyl | " | " | " |
| 1-9) | " | 5-Me-thiophen-2-yl | " | " | " |
| 1-10) | " | 2,3-diMe-phenyl | " | " | " |

TABLE 1-continued
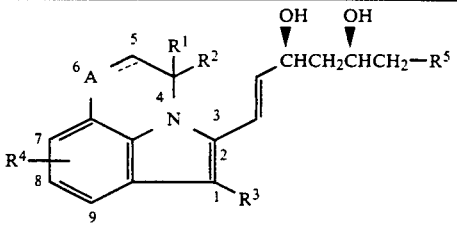
| Example No. | $R^1, R^2$ | $R^3$ | $R^4$ | $R^5$ | —A— |
|---|---|---|---|---|---|
| 1-11) | " | 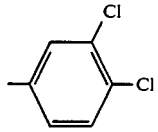 3,4-diCl-phenyl | " | " | " |
| 1-12) | " | 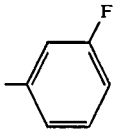 3-F-phenyl | " | " | " |
| 1-13) | " | 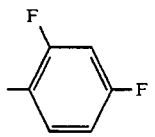 2,4-diF-phenyl | " | " | " |
| 1-14) | Me, Me | 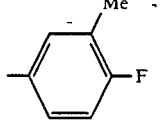 2-F-4-Me-phenyl | H | COOMe | —CH$_2$— |
| 1-15) | " | 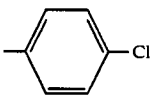 4-Cl-phenyl | " | " | " |
| 1-16) | " | 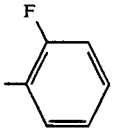 2-F-phenyl | " | " | " |
| 1-17) | " | 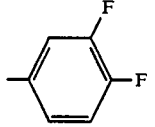 2,3-diF-phenyl | " | " | " |
| 1-18) | " | 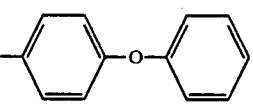 4-phenoxyphenyl | " | " | " |
| 1-19) | " | 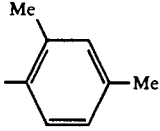 2,5-diMe-phenyl | " | " | " |
| 1-20) | H, H | 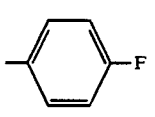 4-F-phenyl | " | " | " |

TABLE 1-continued
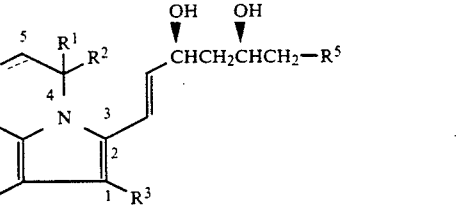
| Example No. | R¹, R² | R³ | R⁴ | R⁵ | —A— |
|---|---|---|---|---|---|
| 1-21) | " | 2,4-F,F-C₆H₃ | " | " | " |
| 1-22) | " | 2,4-Me,Me-C₆H₃ | " | " | " |
| 1-23) | " | 3,4-Cl,Cl-C₆H₃ | " | " | " |
| 1-24) | " | 3-Me,4-F-C₆H₃ | " | " | " |
| 1-25) | Me, Me | 2-MeO,5-F-C₆H₃ | " | " | " |
| 1-26) | Me, Me | 2,4,6-F,F,F-C₆H₂ | H | COOMe | —CH₂— |
| 1-27) | " | 4-F-C₆H₄ | 8-Me | " | " |
| 1-28) | " | " | 8-Cl | " | " |
| 1-29) | " | " | 80-F | " | " |
| 1-30) | " | C₆H₅ | H | " | " |
| 1-31) | " | 4-NMe₂-C₆H₄ | " | " | " |

TABLE 1-continued

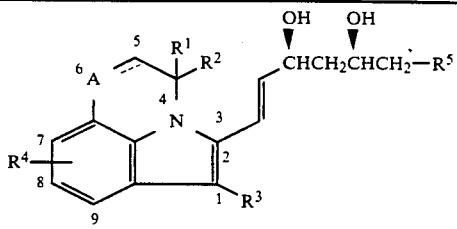

| Example No. | $R^1, R^2$ | $R^3$ | $R^4$ | $R^5$ | —A— |
|---|---|---|---|---|---|
| 1-32) | H, H | 4-F-phenyl | " | " | —O— |
| 1-33) | " | " | " | " | —S— |
| 1-34) | Me, Me | 2-Cl-4-F-phenyl | " | " | —CH$_2$— |
| 1-35) | " | 4-F-phenyl | " | " | —CH= |
| 1-36) | H, H | 2-MeO-4-F-phenyl | " | " | —CH$_2$— |
| 1-37) | Me, Me | 4-OH-phenyl | " | " | " |
| 1-38) | " | 2-MeO-phenyl | " | " | " |
| 1-39) | Me, Me | 2-Me-5-Cl-thienyl | H | COOMe | —CH$_2$— |

| Example No. of Product | Physico-Chemical Data of Table 1 Data |
|---|---|
| 1-3) | NMR (200MHz, CDCl$_3$, δ): 1.3–1.7(2H, m), 1.64(6H, s), 2.10(2H, t, J=6.3Hz), 2.36(3H, s), 2.44(2H, d, J=5.3Hz), 3.00(2H, t, J=6.3Hz), 3.21(1H, br s), 3.64(1H, br s), 3.72(3H, s), 4.14(1H, m), 4.45(1H, m), 5.59(1H, dd, J=5.5Hz and 15.8Hz), 6.84(1H, d, J=15.8Hz), 6.91–7.39(7H, m) IR (Film): 3400, 2940, 1725, 1610, 1530, 1500 cm$^{-1}$ NMR (200MHz, CDCl$_3$, δ): 1.38(3H, d, J=6.6Hz), 1.5–1.8(2H, m), 2.0–2.3(2H, m), 2.49(2H, d, J=6.7Hz), 2.8–3.2(4H, m), 3.72(3H, s), 4.2–5.0(3H, m), 5.98 (1H, dd, J=5.9Hz and 16.2Hz), 6.72(1H, d, J=16.2Hz), 6.9–7.5(7H, m) MASS m/z: 437(M$^+$), 419(M$^+$—H$_2$O), 343, 317, 278 |
| 1-4) | IR (Film): 3450, 2950, 1730, 1610, 1585, 1535 cm$^{-1}$ MASS m/z: 465(M$^+$), 447(M$^+$—H$_2$O), 429, 371, 345 |
| 1-5) | IR (Film): 3430, 2440, 1730, 1600 cm$^{-1}$ NMR (200MHz, CDCl$_3$, δ): 1.63(6H, s), 2.09 (2H, t, J=6.1Hz), 2.32(6H, s), 1.3–1.6 (2H, m), 2.44(2H, d, J=7Hz), 3.00(2H, |

| Example No. of Product | Data |
|---|---|
| | t, J=6.1Hz), 3.26(1H, s), 3.68(1H, s), 3.72(3H, s), 4.16 and 4.46(2H, each m), 5.60(1H, dd, J=5.5 and 15.8Hz), 6.73(1H, d, J=15.7Hz), 6.90-7.40(6H, m)<br>MASS m/z: 461(M+), 341 |
| 1-6) | IR (Film): 3400, 2940, 1725, 1610, 1530 cm−1<br>NMR (200MHz, CDCl3, δ): 1.3-1.6(2H, m), 1.63(6H, s), 2.09(2H, t, J=6.2Hz), 2.26(6H, s), 2.46(2H, d, J=5.3Hz), 2.99(2H, t, J=6.2Hz), 3.36(1H, s), 3.71(1H, s), 3.72(3H, s), 4.17(1H, m), 4.46(1H,m), 5.59(1H, dd, J=5.4Hz and 15.8Hz), 6.83(1H, dd, J=1.4 and 15.8Hz), 6.9-7.4(5H, m)<br>MASS m/z: 479(M+), 461(M+−H2O), 359 |
| 1-7) | IR (Film): 3420, 2940, 1725, 1630, 1600 cm−1<br>NMR (200MHz, CDCl3, δ): 1.2-1.5(2H, m), 1.66(6H, s), 2.12(2H, t, J=6.3Hz), 2.2-2.4(2H, m), 3.02(2H, t, J=6.3Hz), 3.28 and 3.58(2H, each s), 3.68(3H, s), 4.03(1H, m), 4.40(1H, m), 5.57 (1H, dd, J=5.3 and 15.8Hz), 6.8-8.0 (11H, m)<br>MASS m/z: 483(M+), 363, 336 |
| 1-8) | IR (CH2Cl2): 3450, 1730, 1320, 735 cm−1<br>NMR (CDCl3, δ): 1.3-1.6(2H, m), 1.65(6H, s), 2.10(2H, t, J=6Hz), 2.43(2H, d, J=6Hz), 3.01(2H, t, J=6Hz), 3.57(1H, s), 3.72(3H, s), 4.13(1H, m), 4.45 (1H, m), 5.55(1H, dd, J=16 and 6Hz), 6.8-7.7(8H, m) |
| 1-9) | IR (Film): 3400, 1730, 1440, 1180, 730 cm−1<br>NMR (200MHz, CDCl3, δ): 1.5-1.87(2H, m), 1.56(6H, s), 2.10(2H, t, J=6Hz), 2.48 (3H, s), 2.49(2H, d, J=6Hz), 2.8(1H, broad s), 3.05(2H, t, J=6Hz), 3.7(1H, broad s), 3.70(3H, s), 4.25(1H, m), 4.44(1H, m), 6.00(1H, dd, J=7Hz, 16Hz), 6.64(1H, d, J=16Hz), 6.95-7.11 (3H, m), 7.27(1H, d, J=6Hz), 7.51(1H, d, J=4Hz) |
| 1-10) | IR (Film): 3450, 1730, 1440, 730 cm−1<br>NMR (200MHz, CDCl3, δ): 1.40-1.6(2H, m), 1.63(6H, s), 2.09(2H, t, J=6Hz), 2.27 (3H, s), 2.28(3H, s), 2.43-2.47(2H, m), 3.00(2H, t, J=6Hz), 3.14(1H, broad s), 3.63(1H, broad s), 3.72(3H, s), 4.16(1H, m), 4.46(1H, m), 5.62(1H, dd, J=6Hz, 16Hz), 6.84(1H, dd, J=1Hz and 16Hz), 6.91-7.39(6H, m) |
| 1-11) | IR (Film): 3450, 1730, 1440, 735 cm−1<br>NMR (200MHz, CDCl3, δ): 1.4-1.6(2H, m), 1.62(3H, s), 1.63(3H, s), 2.10(2H, t, J=6Hz), 2.50(2H, d, J=6Hz), 3.00(2H, t, J=6Hz), 3.63(1H, d, J=1Hz), 3.73 (4Hz, s), 4.23(1H, m), 4.50(1H, m), 5.61(1H, dd, J=5Hz, 16Hz), 6.86(1H, dd, J=2Hz, 16Hz), 6.94-7.08(2H, m), 7.31-7.53(4H, m) |
| 1-12) | IR (Film): 3450, 1725, 1610, 1440, 740 cm−1<br>NMR (200MHz, CDCl3, δ): 1.40-1.6(2H, m), 1.64(6H, s), 2.10(2H, t, J=6Hz), 2.46 (2H, d, J=6Hz), 3.01(2H, t, J=6Hz), 3.41(1H, broad s), 3.68(1H, broad s), 3.73(3H, s), 4.17(1H, m), 4.48(1H, m), 5.59(1H, dd, J=5Hz, 16Hz), 6.81-7.40(8H, m) |
| 1-13) | IR (Film): 3400, 1725, 1155, 1135, 741 cm−1<br>NMR (CDCl3, δ): 1.32-1.64(2H, m), 1.64 (6H, s), 2.11(2H, t, J=6.3Hz), 2.46 (2H, d, J=5.5Hz), 3.01(2H, t, J=6.3Hz), 3.29(1H, m), 3.66(1H, m), 3.73(3H, s), 4.13(1H, m), 4.45(1H, m), 5.53 (1H, dd, J=5.6 and 15.8Hz), 6.82-7.44 (7H, m) |
| 1-14) | IR (Film): 3400, 1730, 1532, 1172, 1116, 744 cm−1<br>NMR (DMSO-d6, δ): 1.26-1.57(2H, m), 1.59 (6H, s), 2.05(2H, m), 2.30(3H, s), 2.50(2H, m), 2.94(2H, m), 3.58(3H, s), 3.81(1H, m), 4.21(1H, m), 4.78 (1H, d, J=5.4Hz), 4.96(1H, d, J=4.9Hz), 5.58(1H, dd, J=5.4 and 15.9Hz), 6.74-7.29(7H, m) |
| 1-15) | IR (Nujol): 3400, 1725, 1525, 745 cm−1<br>NMR (DMSO-d6, δ): 1.30-1.50(2H, m), 1.59 (6H, s), 2.05(2H, m), 2.50(2H, m), 2.94(2H, m), 3.58(3H, s), 3.81(1H, m), 4.20(1H, m), 4.78(1H, d, J=5.5Hz), 4.97(1H, d, J=4.9Hz), 5.59(1H, dd, J=5.5 and 15.9Hz), 6.79(1H, d, J=15.9Hz), 6.9-7.4(7H, m) |
| 1-16) | IR (Neat): 3450, 1738, 1720, 1153, 745 cm−1<br>NMR (DMSO-d6, δ): 1.20-1.50(2H, m), 1.61 (6H, s), 2.07(2H, m), 2.1-2.5(2H, m), 2.95(2H, m), 3.58(3H, s), 3.75(1H, m), 4.16(1H, m), 4.75(1H, d, J=5.4Hz), 4.93(1H, d, J=4.8Hz), 5.48(1H, dd, J=5.5 and 15.8Hz), 6.79(1H, d, J=15.8Hz), 6.89-7.41(7H, m) |
| 1-17) | IR (Nujol): 3440, 1728, 1602, 1182, 750 cm−1<br>NMR (DMSO-d6, δ): 1.30-1.57(2H, m), 1.58 (6H, s), 2.05(2H, m), 2.20-2.38(2H, m), 2.94(2H, m), 3.58(3H, s), 3.78 (1H, m), 4.22(1H, d, J=4Hz), 4.78(1H, d, J=4Hz), 4.99(1H, m), 5.62(1H, dd, J=5.3 and 15.9Hz), 6.79(1H, d, J=15.9Hz), 6.93-7.49(6H, m) |
| 1-18) | IR (Film): 3450, 1730, 1590, 1232, 748 cm−1<br>NMR (DMSO-d6, δ): 1.30-1.52(2H, m), 1.59 (6H, s), 2.05(2H, m), 2.2-2.5(2H, m), 2.94(2H, m), 3.55(3H, s), 3.90(1H, m), 4.21(1H, m), 4.78(1H, d, J=6Hz), 4.94(1H, d, J=4Hz), 5.59(1H, dd, J=5.6 and 15.8Hz), 6.74-7.44(13H, m) |
| 1-19) | IR (Film): 3450, 1740, 1725, 745 cm−1<br>NMR (DMSO-d6, δ): 1.10-1.40(2H, m), 1.57 (6H, s), 1.93-2.10(5H, m), 2.25(3H, s), 2.47(2H, m), 2.90(2H, m), 3.53 (3H, m), 4.07(2H, m), 4.60(1H, d, J=3.0Hz), 4.76(1H, d, J=3.0Hz), 5.13-5.45(1H, m), 6.60-7.11(7H, m) |
| 1-20) | NMR (CDCl3, δ): 1.6-1.8(2H, m), 2.25(2H, m), 2.52(2H, d, J=6Hz), 3.0(2H, t, J=6Hz), 3.40(1H, m), 3.70(1H, s), 3.72 (3H, s), 4.26(3H, m), 4.53(1H, m), 6.01(1H, dd, J=8 and 17Hz), 6.71(1H, d, J=17Hz), 6.9-7.2(4H, m), 7.3-7.5 (3H, m) |
| 1-21) | IR (Film): 3400, 1730, 1611, 1588, 1135, 742 cm−1<br>NMR (DMSO-d6, δ): 1.56(2H, m), 2.18(2H, m), 2.50(2H, m), 2.93(2H, m), 3.58 (3H, s), 4.01(1H, m), 4.25(3H, m), 4.80(1H, d, J=5.5Hz), 4.98(1H, d, J=4.5Hz), 6.00(1H, dd, J=5.9 and 16.3Hz), 6.57(1H, d, J=16.3Hz), 6.88-7.47(6H, m) |
| 1-22) | IR (Film): 3400, 1730, 1612, 745 cm−1<br>NMR (DMSO-d6, δ): 1.66(2H, m), 2.16(2H, m), 2.26(6H, s), 2.43(2H, m), 2.94 (2H, m), 3.31(2H, m), 3.58(3H, s), 4.01(1H, m), 4.26(3H, m), 4.81(1H, d, J=5.6Hz), 4.98(1H, d, J=4Hz), 6.10 (1H, dd, J=6.1 and 16.4Hz), 6.64(1H, d, J=16.4Hz), 6.87-7.33(6H, m) |
| 1-23) | IR (Film): 3420, 1730, 743 cm−1<br>NMR (DMSO-d6, δ): 1.61(2H, m), 2.16(2H, m), 2.3-2.5(2H, m), 2.95(2H, m), 3.58 (3H, s), 4.01(1H, m), 4.24(3H, m), 4.80(1H, m), 5.04(1H, m), 6.15(1H, dd, J=5.8 and 16.4Hz), 6.65(1H, d, J=16.4Hz), 6.91-7.71(6H, m) |
| 1-24) | IR (Neat): 3430, 1730, 1610, 1160, 744 cm−1 |

-continued

Physico-Chemical Data of Table 1

| Example No. of Product | Data |
|---|---|
| | NMR (DMSO-d$_6$, δ): 1.60(2H, m), 2.16(2H, m), 2.30(3H, s), 2.49(2H, m), 2.95 (2H, m), 3.58(3H, s), 4.01(1H, m), 4.25(3H, m), 4.80(1H, m), 4.95(1H, m), 6.04–6.17(1H, m), 6.63(1H, d, J=16.4Hz), 6.87–7.36(6H, m) |
| 1-25) | IR (Film): 3450, 1730, 1440, 735 cm$^{-1}$ NMR 200MHz, CDCl$_3$, δ): 1.19–1.5(2H, m), 1.62(3H, s), 1.65(3H, s), 2.10(2H, broad t, J=ca.6Hz), 2.42–2.45(2H, m), 3.00(2H, t, J=6Hz), 3.06(1H, broad s), 3.64(1H, broad s), 3.73(6H, s), 4.10 (1H, m), 4.41(1H, m), 5.49(1H, dd, J=6Hz, 16Hz), 6.6–7.2(7H, m) |
| 1-26) | IR (Film): 3400, 1725, 1590, 1435, 750 cm$^{-1}$ NMR 200MHz, CDCl$_3$, δ): 1.2–1.6(2H, m), 1.64(6H, s), 2.09(2H, t, J=6Hz), 2.4–2.5(2H, m), 3.01(2H, t, J=6Hz), 3.30(1H, broad s), 3.70(1H, broad s), 3.37(3H, s), 4.17(1H, m), 4.46(1H, m), 5.56(1H, dd, J=6 and J=16Hz), 6.7–7.4(6H, m) |
| 1-27) | IR (Nujol): 3450, 1732, 1530, 1213, 838 cm$^{-1}$ NMR (DMSO-d$_6$, δ): 1.36(2H, t, J=5.8Hz), 1.57(6H, s), 2.03(2H, t, J=8.0Hz), 2.31–2.50(5H, m), 2.89(1H, m), 3.58 (3H, s), 3.82(1H, m), 4.04(1H, m), 4.77(1H, d, J=5.5Hz), 4.93(1H, d, J=4.8Hz), 5.55(1H, dd, J=5.5 and 15.9Hz), 6.72–7.46(7H, m) |
| 1-28) | IR (Film): 3400, 1725, 1440, 730 cm$^{-1}$ NMR (CDCl$_3$, δ): 1.2–1.7(2H, m), 1.63(6H, s), 2.10(2H, t, J=6Hz), 2.3–2.5(2H, m), 2.97(2H, t, J=6Hz), 3.71(3H, s), 4.1(1H, m), 4.4(1H, m), 5.4–5.8(1H, m), 6.6–7.6(7H, m) |
| 1-29) | IR (Film): 3400, 1730, 1440, 730 cm$^{-1}$ NMR (CDCl$_3$, δ): 1.3–1.5(2H, m), 1.62(6H, s), 2.09(2H, t, J=6Hz), 2.45(2H, d, J=6Hz), 2.97(2H, t, J=6Hz), 3.41(1H, s), 3.64(1H, m), 3.73(3H, s), 4.10 (1H, m), 4.45(1H, m), 5.55(1H, dd, J=15 and 6Hz), 6.6–7.4(7H, m) |
| 1-30) | IR (Film): 3430, 1723, 1603, 743 cm$^{-1}$ NMR (DMSO-d$_6$, δ): 1.25–1.53(2H, m), 1.60 (6H, s), 2.06(2H, t, J=5.9Hz), 2.28–2.50(2H, m), 2.94(2H, m), 3.58 (3H, s), 3.84(1H, m), 4.19(1H, m), 4.77(1H, d, J=5.4Hz), 4.95(1H, d, J=4.9Hz), 5.56(1H, dd, J=5.5 and 15.9Hz), 6.79(1H, d, J=15.9Hz), 6.87–6.97(2H, m), 7.19–7.40(6H, m) |
| 1-31) | IR (Film): 3410, 1730, 1611, 1160, 743 cm$^{-1}$ NMR (DMSO-d$_6$, δ): 1.00–1.47(2H, m), 1.53 (6H, s), 2.00(2H, t, J=6.3Hz), 2.28 (2H, m), 2.85(8H, m), 3.52(3H, s), 3.70–4.22(2H, m), 4.66(1H, d, J=4.2Hz), 4.81(1H, d, J=4.8Hz), 5.57 (1H, dd, J=6.0 and 15.3Hz), 6.62–7.20 (8H, m) |
| 1-32) | IR (Neat): 3450, 2950, 1730, 1630, 1585 cm$^{-1}$ NMR (CDCl$_3$, δ): 1.6–1.9(2H, m), 2.51(2H, d, J=6.2Hz), 3.58(1H, s), 3.72(3H, s), 3.75(1H, s), 4.3–4.6(6H, m), 6.02(1H, dd, J=6.1 and 16.4Hz), 6.70(1H, d, J=16.4Hz), 6.70(1H, d, J=7.5Hz), 6.98 (1H, t, J=7.5Hz), 7.09–7.19(3H, m), 7.42–7.49(2H, m) MASS m/z: 425, 407, 304 |
| 1-33) | mp: 148–150° C. IR (Nujol): 3490, 1735, 1540, 1500 cm$^{-1}$ NMR (CDCl$_3$, δ): 1.5–1.8(2H, m), 2.51(2H, d, J=6.2Hz), 3.2–3.3(2H, m), 3.4–3.8 (2H, m), 3.37(3H, s), 4.2–4.5(1H, m), 4.5–4.6(3H, m), 5.93(1H, dd, J=5.8Hz and 16.3Hz), 6.69(1H, dd, J=1.4 and 16.3Hz), 6.9–7.5(7H, m) |
| 1-34) | NMR (CDCl$_3$, δ): 1.37–1.53(2H, m), 1.60 (3H, s), 1.63(3H, s), 2.08(2H, t, J=6.6Hz), 2.40(2H, d, J=6.0Hz), 2.98 (2H, t, J=6.6Hz), 3.68(3H, s), 4.00–4.47(2H, m), 5.35(1H, dd, J=6.0Hz and 15.0Hz), 6.64–7.37(7H, m) MASS m/z: 449, 485 |
| 1-35) | IR (Film): 3400, 1724, 1218, 740 cm$^{-1}$ NMR (DMSO-d$_6$, δ): 1.29–1.61(2H, m), 1.71 (6H, s), 2.21–2.40(2H, m), 3.58(3H, s), 3.80(1H, m), 4.20(1H, m), 4.78 (1H, s), 4.98(1H, d, J=4.9Hz), 5.62(1H, dd, J=5.5 and 15.8Hz), 5.78 (1H, d, J=9.9Hz), 6.56(1H, d, J=9.9Hz), 6.82–6.94(3H, m), 7.17–7.27(3H, m), 7.40–7.47(2H, m) |
| 1-36) | IR (Film): 3400, 1726, 1600, 1150, 744 cm$^{-1}$ NMR (DMSO-d$_6$, δ): 1.43–1.71(2H, m), 2.18 (2H, br), 2.29–2.5(2H, m), 2.94(2H, br), 3.58(3H, s), 3.71(3H, s), 3.96 (1H, m), 4.24(3H, br), 4.78(1H, d, J=5.5Hz), 4.91(1H, d, J=4.4Hz), 5.92 (1H, dd, J=6.1 and 16.3Hz), 6.50(1H, d, J=16.3Hz), 6.78–7.25(6H, m) |
| 1-37) | IR (Nujol): 3650, 3400, 2950, 1720 cm$^{-1}$ NMR CDCl$_3$, δ): 1.45(18H, s), 1.45–1.63 (2H, m), 1.64(6H, s), 2.09(2H, t, J=6.2Hz), 2.40–2.60(2H, m), 3.00(2H, t, J=6.2Hz), 3.24(1H, s), 3.71(4H, s), 4.23(1H, m), 4.47(1H, m), 5.10(1H, s), 5.66(1H, dd, J=5.5 and 15.8Hz), 6.86(1H, dd, J=1.5 and 15.8Hz), 6.93–7.03(2H, m), 7.22(2H, s), 7.35 (1H, d, J=7.5Hz) MASS m/z: 561, 525, 441 |
| 1-38) | IR (Film): 3400, 2940, 1730, 1605 cm$^{-1}$ MASS m/z: 463 |
| 1-39) | IR (Neat): 3420, 2950, 1730, 1615, 1550 cm$^{-1}$ NMR (CDCl$_3$, δ): 1.57(6H, s), 1.4–1.8(2H, m), 2.09(2H, t, J=6.4Hz), 2.4–2.7(2H, m), 3.06(2H, t, J=6.4Hz), 3.68(3H, s), 4.1–4.6(2H, m), 5.98(1H, dd, J=6.8Hz and 15.9Hz), 66.1(1H, d, J=15.9Hz), 7.0–7.6(5H, m) MASS m/z: 473(M$^+$), 455, 437(base) |

EXAMPLE 2-1

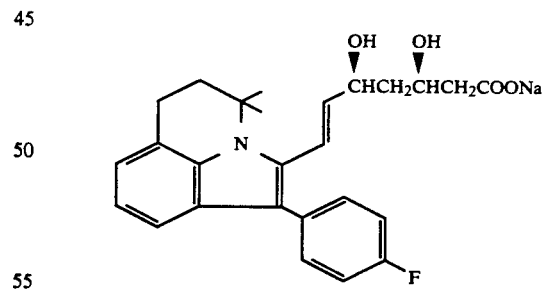

1N Aqueous sodium hydroxide (3.54 ml) was added dropwise to a solution of methyl (±)-erythro-(E)-7-[5,6-dihydro-4,4-dimethyl-1-(4-fluorophenyl)-4H-pyrrolo[3,2,1-ij]quinolin-2-yl]-3,5-dihydroxyhept-6-enoate (1.6 g) in methanol (15 ml) under ice-cooling. The reaction mixture was allowed to warm to room temperature and stirred at the same temperature for 3 hours. The solvent was evaporated under reduced pressure, and the residue was dissolved in distilled water (10 ml), filtered and freeze-dried to give yellowish powder of sodium (±)-erythro-(E)-7-[5,6-dihydro-4,4-dimethyl-1-(4- fluorophenyl)-4H-pyrrolo[3,2,1-ij]quinolin-2-yl]-3,5-dihydroxyhept-6-enoate (1.53 g).
IR (Nujol): 3300, 1565, 1220 cm$^{-1}$
NMR (DMSO-d$_6$, δ): 1.16–1.52 (2H, m), 1.58 (6H, s), 1.79–2.10 (4H, m), 2.903 (2H, m), 3.63 (1H, m), 4.22 (1H, m), 5.16 (1H, br s), 5.56 (1H, dd, J=6Hz and 16Hz), 6.75 (1H, d, J=16Hz), 6.86–6.97 (2H, m), 7.07 (1H, br s), 7.15–7.24 (3H, m), 7.37–7.44 (2H, m).
The compounds of Table 2 were obtained in substantially the same manner as that of Example 2-1).
TABLE 2
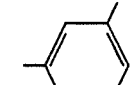
| Example No. | R$^1$, R$^2$ | R$^3$ | R$^4$ | R$^5$ | —A— |
|---|---|---|---|---|---|
| 2-2) | Me, Me | 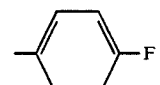 | H | COONa | —CH$_2$— |
| 2-3) | H, Me | 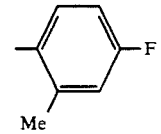 | " | " | " |
| 2-4) | Me, Me | 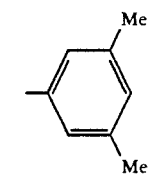 | " | " | " |
| 2-5) | " | 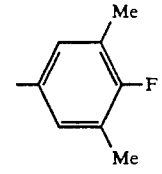 | " | " | " |
| 2-6) | " | 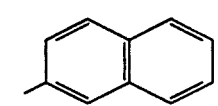 | " | " | " |
| 2-7) | " | 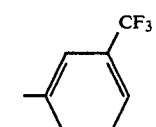 | " | " | " |
| 2-8) | " | 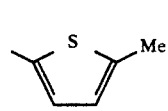 | " | " | " |
| 2-9) | " |  | " | " | " |

TABLE 2-continued
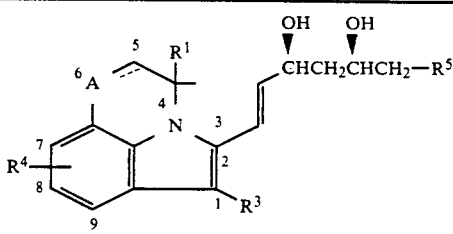
| Example No. | $R^1, R^2$ | $R^3$ | $R^4$ | $R^5$ | —A— |
|---|---|---|---|---|---|
| 2-10) | Me, Me | 2,4-di-Me-phenyl | H | COONa | —CH$_2$— |
| 2-11) | " | 3,4-di-Cl-phenyl | " | " | " |
| 2-12) | " | 3-F-phenyl | " | " | " |
| 2-13) | " | 2,4-di-F-phenyl | " | " | " |
| 2-14) | " | 4-F-3-Me-phenyl | " | " | " |
| 2-15) | " | 4-Cl-phenyl | " | " | " |
| 2-16) | " | 2-F-phenyl | " | " | " |
| 2-17) | " | 3,4-di-F-phenyl | " | " | " |
| 2-18) | " | 4-phenoxyphenyl | " | " | " |

TABLE 2-continued
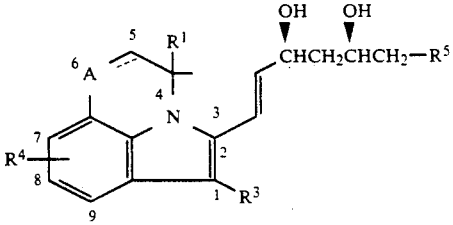
| Example No. | R¹, R² | R³ | R⁴ | R⁵ | —A— |
|---|---|---|---|---|---|
| 2-19) | " | 2,4-diMe-phenyl (Me, Me) | " | " | " |
| 2-20) | H, H | 4-F-phenyl | " | " | " |
| 2-21) | " | 2,4-diF-phenyl | " | " | " |
| 2-22) | H, H | 2,4-diMe-phenyl | H | COONa | —CH₂— |
| 2-23) | " | 3,4-diCl-phenyl | " | " | " |
| 2-24) | " | 3-Me-4-F-phenyl | " | " | " |
| 2-25) | Me, Me | 3-OMe-4-F-phenyl | " | " | " |
| 2-26) | " | 2,4,5-triF-phenyl | " | " | " |
| 2-27) | " | 4-F-phenyl | 8-Me | " | " |
| 2-28) | " | " | 8-Cl | " | " |
| 2-29) | " | " | 8-F | " | " |

TABLE 2-continued
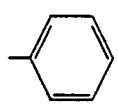
| Example No. | R¹, R² | R³ | R⁴ | R⁵ | —A— |
|---|---|---|---|---|---|
| 2-30) | " | 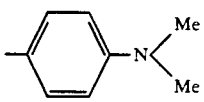 | H | " | " |
| 2-31) | Me, Me | 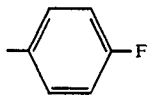 | " | " | " |
| 2-32) | H, H |  | " | " | —O— |
| 2-33) | " | " | " | " | —S— |
| 2-34) | H, H | 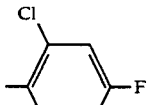 | H | COONa | —SO— |
| 2-35) | " | " | " | " | —SO₂— |
| 2-36) | Me, Me | 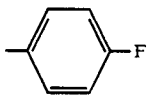 | " | " | —CH₂— |
| 2-37) | " | 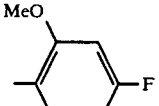 | " | " | —CH= |
| 2-38) | H, H | 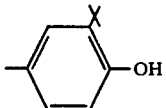 | " | " | —CH₂— |
| 2-39) | Me, Me | 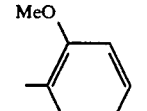 | " | " | " |
| 2-40) | " | MeO | " | " | " |

TABLE 2-continued

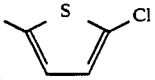

| Example No. | $R^1, R^2$ | $R^3$ | $R^4$ | $R^5$ | —A— |
|---|---|---|---|---|---|
| 2-41) | " | (thiophene with Cl) | " | " | " |

| Example No. of Product | Physico-Chemical Data of Table 2 Data |
|---|---|
| 2-2) | IR (Nujol): 3350, 1565, 742 cm$^{-1}$<br>NMR (200 MHz, DMSO-d$_6$, δ): 1.16–1.48(2H, m), 1.59(6H, s), 1.75–1.87(4H, m), 2.32(3H, s), 2.93(2H, br s), 3.56(1H, m), 4.20(1H, m), 5.12(1H, br s), 5.57 (1H, dd, J=5.1 and 15.9Hz), 6.75(1H, d, J=15.9Hz), 6.85–7.30(7H, m) |
| 2-3) | IR (Nujol): 3330, 1570, 1220, 835, 740 cm$^{-1}$<br>NMR (200MHz, CD$_3$OD, δ): 1.35 and 1.36(3H, each d, J=6.5Hz), 1.5–1.8(2H, m), 2.1–2.3(2H, m), 2.3–2.5(2H, m), 2.8–3.1(2H, m), 3.9–4.2(1H, m), 4.3–4.5(7H, m), 5.9–6.1(1H, m), 6.73 (1H, d, J=16.3Hz), 6.8–7.5(7H, m)<br>Anal. Calcd. for C$_{25}$H$_2$FNO$_4$N$_a$ ·1.5H$_2$O: C 63.55, H 5.97, N 2.96<br>Found: C 63.49, H 5.79, N 2.79 |
| 2-4) | IR (Nujol): 3350, 1565 cm$^{-1}$<br>NMR (200MHz, DMSO-d$_6$, δ): 1.2–1.5(2H, m), 1.60(6H, s), 1.65–2.10(7H, m),* 2.8–3.0(2H, m), 3.47(1H, m), 4.13(1H, br s), 5.06(1H, br s), 5.33(1H, dd, J=4.1 and 15.7Hz), 6.73(1H, d, J=15.7Hz), 6.8–7.3(6H, m) |
| 2-5) | IR (Nujol): 3300, 1570, 740 cm$^{-1}$<br>NMR (200MHz, CD$_3$OD, δ): 1.3–1.6(2H, m), 1.64(6H, s), 2.08(2H, t, J=6.1Hz), 2.1–2.3(2H, m), 2.32(6H, s), 2.97(2H, t, J=6.1Hz), 3.82(1H, m), 4.36(1H, m), 5.60(1H, dd, J=5.9 and 15.8Hz), 6.7–7.3 (7H, m) |
| 2-6) | IR (Nujol): 3350, 1565, 1180, 740 cm$^{-1}$<br>NMR (90MHz, DMSO-d$_6$, δ): 1.0–1.5(2H, m), 1.56(6H, s), 1.7–2.1(4H, m), 2.21(6H, s), 2.7–3.0(2H, m), 3.4–3.8(1H, m), 4.0–4.4(1H, m), 4.4–5.3(2H, br s), 5.57(1H, dd, J=5 and 16Hz), 6.6–7.3 (6H, m) |
| 2-7) | IR (Nujol): 3300, 1565, 1150, 740 cm$^{-1}$<br>NMR (200MHz, DMSO-d$_6$, δ): 1.1–1.5(2H, m), 1.62(6H, s), 1.7–2.0(2H, m), 2.07(2H, br s), 2.50(2H, br s), 3.60(1H, m), 4.18(1H, m), 5.12(1H, br s), 5.59(1H, dd, J=5.2 and 15.9Hz), 6.85(1H, d, J=15.8Hz), 6.9–7.0(2H, m), 7.14(1H, br s), 7.33(1H, d, J=7.2Hz), 7.4–7.5(2H, m), 7.55(1H, d, J=8.5Hz), 7.8–8.0(4H, m) |
| 2-8) | IR (Nujol): 3350, 1570, 1120, 740 cm$^{-1}$<br>NMR (DMSO-d$_6$, δ): 1.2–1.4(2H, m), 1.59 (6H, s), 1.6–2.2(4H, m), 2.95(2H, m), 3.57(1H, m), 4.24(1H, m), 5.19(1H, br s), 5.58(1H, dd, J=16 and 4Hz), 6.81 (1H, d, J=16Hz), 6.9–7.75(7H, m) |
| 2-9) | IR (Film): 3350, 1570 cm$^{-1}$<br>NMR (200MHz, DMSO-d$_6$, δ): 1.2–1.6(2H, m), 1.53(6H, s), 1.79–2.03(4H, m), 2.43 (3H, s), 2.98(2H, m), 3.72(1H, m), 4.17(1H, m), 4.86(1H, broad s), 6.03 (1H, dd, J=6Hz, 16Hz), 6.50(1H, d, J=16Hz), 6.92–7.05(3H, m), 7.20(1H, broad s), 7.38(1H, d, J=8Hz), 7.56(1H, s) |
| 2-10) | IR (Nujol): 3350, 1570, 740 cm$^{-1}$<br>NMR (200MHz, DMSO-d$_6$, δ): 1.23–1.5(2H, m), 1.58(6H, s), 1.74–2.0(4H, m), 2.23 (6H, s), 2.93(2H, m), 3.56(1H, m), 4.20(1H, m), 5.08(1H, broad s), 5.59 (1H, dd, J=5 and 16Hz), 6.74(1H, d, J=16Hz), 6.87–7.30(7H, m) |
| 2-11) | IR (Nujol): 3350, 1570, 740 cm$^{-1}$<br>NMR (200MHz, CD$_3$OD, δ): 1.43–1.74(2H, m), 1.63(6H, s), 2.08(2H, t, J=6Hz), 2.19–2.43(2H, m), 2.98(2H, t, J=6Hz), 3.95(1H, m), 4.40(1H, quartet, J=6Hz), 5.63(1H, dd, J=6Hz, 16Hz), 6.83–7.00 (3H, m), 7.22–7.55(4H, m)<br>NMR (200MHz, DMSO-d$_6$, δ): 1.24–1.6(2H, m), 1.58(6H, s), 1.79–2.11(4H, m), 2.94 (2H, broad t), 3.62(1H, m), 4.24(1H, m), 5.21(1H, broad s), 5.61(1H, dd, J=5 and 16Hz), 6.79(1H, d, J=16Hz), 6.90–7.01(2H, m), 7.24–7.64(4H, m) |
| 2-12) | IR (Nujol): 3350, 1575 cm$^{-1}$<br>NMR (200MHz, CD$_3$OD, δ): 1.37–1.7(2H, m), 1.63(6H, s), 2.08(2H, t, J=6Hz), 2.1–2.38(2H, m), 2.97(2H, t, J=6Hz), 3.87(1H, m), 4.37(1H, dd, J=6Hz, 13Hz), 5.61(1H, dd, J=6 and 16Hz), 6.83–7.43(8H, m)<br>NMR (200MHz, DMSO-d$_6$, δ): 1.15–1.67(2H, m), 1.58(6H, s), 1.77–2.08(4H, m), 2.94(2H, m), 3.59(1H, m), 4.23(1H, m), 5.19(1H, broad s), 5.60(1H, dd, J=5 and 16Hz), 6.78(1H, d, J=16Hz), 6.88–7.47(8H, m) |
| 2-13) | NMR (DMSO-d$_6$, δ): 1.36–1.59(2H, m), 1.59 (6H, s), 1.74–2.06(4H, m), 2.95(2H, m), 3.54(1H, m), 4.19(1H, m), 5.13 (1H, br s), 5.48(1H, dd, J=5.20 and 15.8Hz), 6.74(1H, d, J=15.8Hz), 6.89–7.42(6H, m) |
| 2-14) | NMR (DMSO-d$_6$, δ): 1.10–1.58(2H, m), 1.58 (6H, s), 1.77–2.10(4H, m), 2.25(3H, s), 2.93(2H, m), 3.36(1H, s), 3.62 (1H, m), 4.22(1H, m), 5.14(1H, br s), 5.57(1H, dd, J=5.2 and 15.9Hz), 6.71–7.28(7H, m) |
| 2-15 | NMR (DMSO-d$_6$, δ): 1.10–1.58(2H, m), 1.58 (6H, s), 1.78–2.08(4H, m), 2.94(2H, m), 3.63(1H, m), 4.21(1H, m), 5.17 (1H br s), 5.57(1H, dd, J=5.1 and |

-continued

Physico-Chemical Data of Table 2

| Example No. of Product | Data |
|---|---|
| | 15.9Hz), 6.76(1H, d, J=15.8Hz), 6.88–7.41(7H, m) |
| 2-16) | (DMSO-$d_6$, $\delta$): 1.10–1.59(2H, m), 1.59 (6H, s), 1.70–2.10(4H, m), 2.95(2H, m), 3.48(1H, m), 4.15(1H, m), 5.08 (1H, br s), 5.48(1H, dd, J=5.0 and 15.8Hz), 6.75(1H, d, J=15.8Hz), 6.89–7.39(7H, m) |
| 2-17) | NMR (DMSO-$d_6$, $\delta$): 1.20–1.57(2H, m), 1.57 (6H, s), 1.76–2.07(4H, m), 2.94(2H, m), 3.34(3H, s), 3.61(1H, m), 4.22 (1H, m), 5.17(1H, br s), 5.60(1H, dd, J=5.0 and 15.9Hz), 6.76(1H, d, J=15.9Hz), 6.88–7.49(6H, m) |
| 2-18) | NMR (DMSO-$d_6$, $\delta$): 1.20–1.51(2H, m), 1.59 (6H, s), 1.78–2.08(4H, m), 2.94(2H, m), 3.35(1H, s), 3.67(1H, br s), 4.24 (1H, br s), 5.15(1H, br s), 5.55(1H, dd, J=5.0 and 15.9Hz), 6.71–7.46(13H, m) |
| 2-19) | NMR (DMSO-$d_6$, $\delta$): 0.80–1.32(2H, m), 1.60 (6H, s), 1.67–2.07(7H, m), 2.32(3H, s), 2.94(2H, m), 3.35(2H, m), 4.12 (1H, br s), 5.00(1H, br s), 5.36(1H, dd, J=5.0 and 15.8Hz), 6.68–7.23(7H, m) |
| 2-20) | NMR (CD$_3$OD, $\delta$): 1.6–1.8(2H, m), 2.21(2H, m), 2.36(2H, m), 2.96(2H, t, J=6Hz), 4.07(1H, m), 4.28(2H, t, J=6Hz), 4.42 (1H, m), 6.06(1H, dd, J=6 and 16Hz), 6.70(1H, d, J=16Hz), 6.8–7.5(7H, m) |
| 2-21) | NMR (CD$_3$OD, $\delta$): 1.57–1.79(2H, m), 2.23–2.40(4H, m), 2.96(2H, m), 4.03 (1H, m), 4.26(2H, m), 4.38(1H, m), 5.98(1H, dd, J=6.6 and 16.3Hz), 6.64 (1H, d, J=16.3Hz), 6.84–7.48(6H, m) |
| 2-22) | NMR (C$_3$OD, $\delta$): 1.73(2H, m), 2.1–2.5(4H, m), 2.30(6H, s), 2.93(2H, m), 3.90–4.63(4H, m), 6.03(1H, dd, J=6.8Hz and 16.2Hz), 6.62–7.33(7H, m) |
| 2-23) | NMR (CD$_3$OD, $\delta$): 1.72(2H, m), 2.20(2H, m), 2.36(2H, m), 2.97(2H, m), 2.97(2H, m), 4.03(1H, m), 4.26(2H, m), 4.43(1H, m), 6.10 (1H, m), 6.70(1H, d, J=16.3Hz), 6.91–7.61(6H, m) |
| 2-24) | NMR (CD$_3$OD, $\delta$): 1.77(2H, m), 2.20(2H, m), 2.30(3H, s), 2.34(2H, m), 2.93(2H, m), 4.10(1H, m), 4.26(2H, m), 4.43 (1H, m), 6.00–6.16(1H, m), 6.70(1H, d, J=16Hz), 6.8–7.4(6H, m) |
| 2-25) | IR (Nujol): 3350, 1565 cm$^{-1}$<br>NMR (200MHz, DMSO-$d_6$, $\delta$): 1.02–1.5(2H, m), 1.58(6H, s), 1.72–2.05(4H, m), 2.93 (2H, broad t, J=ca.6Hz), 3.51(1H, m), 3.69(3H, s), 4.16(1H, m), 5.02(1H, broad s), 5.43(1H, dd, J=5 and 16Hz), 6.63–7.17(8H, m)<br>NMR (200MHz, CD$_3$OD, $\delta$): 1.22–1.6(2H, m), 1.64(6H, broad s), 2.06–2.34(4H, m), 2.98(2H, t, J=6Hz), 3.72(3H, s), 3.7 (1H, m), 4.32(1H, m), 5.49(1H, dd, J=6 and 16Hz), 6.67–7.2(7H, m) |
| 2-26) | IR (Nujol): 3350, 1590 cm$^{-1}$<br>NMR (200MHz, CD$_3$OD, $\delta$): 1.28–1.6(2H, m), 1.65(6H, s), 2.11(2H, t, J=6Hz), 2.21–2.37(2H, m), 3.00(2H, t, J=6Hz), 3.86(1H, m), 4.36(1H, m), 5.55(1H, dd, J=6 and 16Hz), 6.67(1H, d, J=16Hz), 6.8–7.4(5H, m) |
| 2-27) | NMR (DMSO-$d_6$, $\delta$): 1.10–1.55(2H, m), 1.56 (6H, s), 1.76–2.08(4H, m), 2.31(3H, s), 2.89(2H, m), 3.35(1H, m), 3.61 (1H, m), 4.21(1H, m), 5.12(1H, m), 5.53(1H, dd, J=5.2 and 15.9Hz), 6.69–7.42(8H, m) |
| 2-28) | NMR (DMSO-$d_6$, $\delta$): 1.1–1.6(2H, m), 1.57 (6H, s) 1.7–2.2(4H, m), 2.93(2H, m), 4.22(1H, m), 5.59(1H, m), 6.73(1H, d, |
| | J=16Hz), 6.8–7.5(6H, m) |
| 2-29) | NMR (DMSO-$d_6$, $\delta$): 1.1–1.6(2H, m), 1.57 (6H, s), 1.78–2.07(4H, m), 2.94(2H, br s), 3.61(1H, m), 4.1(1H, m), 5.18 (1H, br s), 5.56(1H, dd, J=16 and 6Hz), 6.7–7.5(7H, m) |
| 2-30) | NMR (DMSO-$d_6$, $\delta$): 1.16–1.53(2H, m), 1.59 (6H, s), 1.76–2.08(4H, m), 2.94(2H, m), 3.40(1H, br), 3.59(1H, m), 4.20 (1H, m), 5.57(1H, dd, J=5.1 and 15.8Hz), 6.76(1H, d, J=14.8Hz), 6.86–6.96(2H, m), 7.19–7.39(6H, m) |
| 2-31) | NMR (DMSO-$d_6$, $\delta$): 1.20–1.52(2H, m), 1.58 (6H, s), 1.76–2.07(4H, m), 2.91(8H, br), 3.35(1H, br), 3.65(1H, m), 4.21 (1H, m), 5.08(1H, br), 5.61(1H, dd, J=5.2 and 15.9Hz), 6.68–6.92(4H, m), 7.16–7.23(4H, m) |
| 2-32) | IR (Nujol): 3320, 1570 cm$^{-1}$<br>NMR (CD$_3$OD, $\delta$): 1.6–1.9(2H, m), 2.2–2.5 (2H, m), 4.09(1H, m), 4.3–4.5(5H, m), 6.13(1H, dd, J=6.6 and 16.4Hz), 6.59 (1H, d, J=7.5 Hz), 6.70(1H, d, J=16.4Hz), 6.90(1H, t, J=7.5Hz), 7.09 (1H, d, J=7.5Hz), 7.17(2H, m), 7.51 (2H, m) |
| 2-33) | IR (Nujol): 3300, 1565 cm$^{-1}$<br>NMR (CD$_3$OD, $\delta$): 1.5–2.0(2H, m), 2.32(2H, d, J=6Hz), 3.1–3.3(2H, m), 3.8–4.2(1H, m), 4.2–4.6(3H, m), 5.95(1H, dd, J=6Hz and 16Hz), 6.63(1H, d, J=16Hz), 6.8–7.5 (7H, m) |
| 2-34) | IR (Nujol): 3350, 1570 cm$^{-1}$<br>NMR (CD$_3$OD, $\delta$): 1.6–1.8(2H, m), 2.3–2.5 (2H, m), 3.0–3.8(2H, m), 4.0–4.5(2H, m), 4.5–4.9(2H, m), 4.0–4.5(2H, m), 4.5–4.9(2H, m), 6.18(1H, dd, J=6.5 and 16.3Hz), 6.77(1H, d, J=16.3Hz), 7.1–7.8(7H, m) |
| 2-35) | IR (Neat): 3350, 1570 cm$^{-1}$<br>NMR (CD$_3$OD, $\delta$): 1.6–1.9(2H, m), 2.35(2H, d, J=5.5Hz), 4.06(1H, m), 4.45(1H, m), 4.7–5.0(4H, m), 6.13(1H, dd, J=6.3Hz and 16.3Hz), 6.71(1H, d, J=16.3Hz), 7.1–7.8(7H, m) |
| 2-36) | NMR (CD$_3$OD, $\delta$): 1.2–1.5(2H, m), 1.64(3H, s), 1.67(3H, s), 2.11(2H, t, J=6.3Hz), 2.22–2.27(2H, m), 3.00(2H, t, J=6.3Hz), 3.77(1H, m), 4.31(1H, m), 5.44(1H, dd, J=6.2 and 15.8Hz), 6.80–7.55(7H, m) |
| 2-37) | NMR (DMSO-$d_6$, $\delta$): 1.14–1.53(2H, m), 1.70 (6H, s), 1.80–2.08(2H, m), 3.59(1H, br), 4.20(1H, br), 5.17(1H, br), 5.61 (1H, dd, J=5.1 and 15.8Hz), 5.77(1H, d, J=9.8Hz), 6.55(1H, d, J=9.8Hz), 6.81–6.93(3H, m), 7.17–7.26(4H, m), 7.39–7.46(2H, m) |
| 2-38) | IR (Nujol): 3300, 1563, 1150, 740 cm$^{-1}$<br>NMR (DMSO-$d_6$, $\delta$): 1.32–1.63(2H, m), 1.81–2.17(4H, m), 2.93(2H, br), 3.70 (3H, s), 3.70(1H, m), 4.22(3H, m), 5.05(1H, br), 5.93(1H, dd, J=5.8 and 16.3Hz), 6.48(1H, d, J=16.4Hz), 6.79–7.24(7H, m) |
| 2-39) | IR (Nujol): 3350, 1570 cm$^{-1}$<br>NMR CD$_3$OD, $\delta$): 1.46(18H, s), 1.64(6H, s), 1.2–1.6(2H, m), 2.08(2H, t, J=6.3Hz), 2.2–2.4(2H, m), 2.97(2H, t, J=6.3Hz), 3.98(1H, m), 4.38(1H, m), 5.70(1H, dd, J=5.6 and 15.8Hz), 6.7–7.1(4H, m), 7.18(1H, d, J=7.3Hz), 7.19(2H, s) |
| 2-40) | IR (Nujol): 3350, 1570, 740 cm$^{-1}$<br>NMR (CDCl$_3$, $\delta$): 1.3–2.0(8H, m), 2.0–2.4(4H, m), 2.9–3.1(2H, m), 3.81 (3H, s), 4.0–4.5(2H, m), 5.63(1H, dd, J=5.9 and 15.9Hz), 6.7–7.7(8H, m) |

| Physico-Chemical Data of Table 2 | |
|---|---|
| Example No. of Product | Data |
| 2-41) | IR (Nujol): 3300, 1570 cm$^{-1}$<br>NMR (CD$_3$OD, δ): 1.56(6H, s), 1.6–1.9(2H, m), 2.07(2H, t, J=6.2Hz), 2.2–2.4(2H, m), 3.03(2H, t, J=6.2Hz), 3.9–4.1(1H, m), 4.2–4.4(1H, m), 6.07(1H, dd, J=6.9 and 15.8Hz), 6.64(1H, d, J=15.8Hz), 6.95(1H, d, J=6.9Hz), 7.04 (1H, t, J=6.9Hz), 7.22(1H, s), 7.42 (1H, d, J=6.9Hz), 7.48(1H, s) |

EXAMPLE 3-1

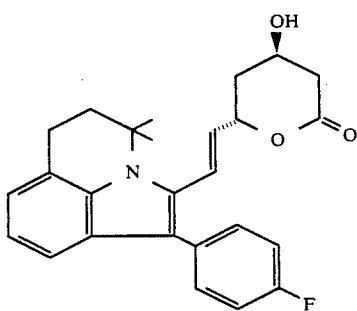

1N Hydrochloric acid (0.05 ml) was added to a solution of sodium (±)-erythro-(E)-7-[5,6-dihydro-4,4-dimethyl-1-(4-fluorophenyl)-4H-pyrrolo[3,2,1-ij]quinolin-2-yl]-3,5-dihydroxyhept-6-enoate (23 mg) in water (0.7 ml) under ice-cooling. The reaction mixture was extracted with diethyl ether. The extract was washed with saturated aqueous sodium chloride, dried over anhydrous magnesium sulfate and evaporated under reduced pressure. The residue was dissolved in dry dichloromethane (1ml). N-Ethyl-N'-(3-dimethylaminopropyl)carbodiimide hydrochloride (9.6 mg) was added to the solution at room temperature. The reaction mixture was stirred for 4 hours at room temperature and then extracted with dichloromethane. The extract was dried over anhydrous magnesium sulfate, filtered and evaporated under reduced pressure. The obtained oil was purified by chromatography on a silica gel column eluting with a mixture of n-hexane and ethyl acetate (1:1, V/V) to give (±)-(E)-6-[2-{5,6-dihydro-4,4-dimethyl-1-(4-fluorophenyl)-4H-pyrrolo[3,2,1-ij]quinolin-2-yl}ethenyl]-4-hydroxy-3,4,5,6-tetrahydro-2H-pyran-2one (trans isomers containing a trace amount of cis isomers) (10 mg).

IR (Nujol): 3450, 1730, 1540, 1500, 1450, 1370, 1230, 1160, 1040, 730 cm$^{-1}$.

EXAMPLE 3-2

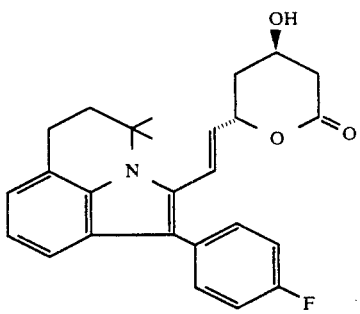

1N Hydrochloric acid (1.8 ml) was added dropwise to a solution of sodium (±)-erythro-(E)-7-[5,6-dihydro-4,4-dimethyl-1-(4-fluorophenyl)-4H-pyrrolo[3,2,1-ij]quinolin-2-yl]-3,5-dihydroxyhept-6-enoate (770 mg) in water (23 ml) under ice-cooling. The reaction mixture was extracted with ethyl acetate. The extract was washed with saturated aqueous sodium chloride, dried over anhydrous magnesium sulfate and evaporated under reduced pressure. The residue was dissolved in dry toluene (25 ml) and this solution was heated under reflux in a Dean-Stark apparatus. After 3.5 hours, the toluene was removed in vacuo. The residual syrup was subjected to a column chromatography on silica gel (27 g) and eluted with a mixture of n-hexane and ethyl acetate (1:1, V/V) to give two fractions. The former fraction gave (±)-(E)-6-[2-{5,6-dihydro-4,4-dimethyl-1-(4-fluorophenyl)-4H-pyrrolo[3,2,1-ij]quinolin-2-yl}ethenyl]-4-hydroxy-3,4,5,6-tetrahydro-2H-pyran-2-one (tarns isomer) (0.28 g)

mp: 165.5°–166.5° C. (recrystallized from dichloromethane-diisopropyl ether).

IR (Nujol): 3450, 1730, 1540, 1500, 1450, 1370, 1230, 1160, 1040, 730 cm$^{-1}$.

NMR (CDCl$_3$, δ): 1.54–1.91 (2H, m), 1.63 (6H, s), 2.10 (3H, m), 2.60 (1H, m, J=1, 4 and 17Hz), 2.73 (1H, dd, J=4 and 17Hz), 3.01 (2H, t, J=6Hz), 4.29 (1H, br s), 5.22 (1H, m), 5.55 (1H, dd, J=6 and 16Hz), 6.89 (1H, dd, J=1 and 16Hz), 6.95–7.14 (4H, m), 7.25–7.41 (3H, m).

The second fraction gave a mixture of trans racemate and cis racemate (0.35 g).

EXAMPLE 4

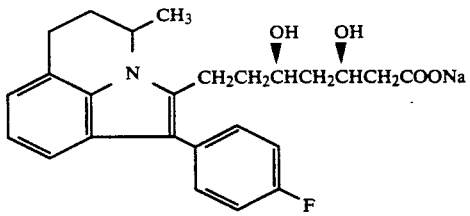

A mixture of sodium (±)-erythro-(E)-7-[5,6-dihydro-1-(4-fluorophenyl)-4-methyl-4H-pyrrolo[3,2,1-ij]quinolin-2-yl]-3,5-dihydroxyhept-6-enoate (0.50 g) in methanol (10 ml) was hydrogenated for 4 hours at room temperature in the presence of 10% palladium on carbon (0.1 g). The reaction mixture was filtered and the filtrate was evaporated. The residue was dissolved in distilled water and freeze-dried to give sodium (±)-erythro-(E)-7-[5,6-dihydro-1-(4-fluorophenyl)-4-methyl-4H-pyrrolo[3,2,1-ij]quinolin-2-yl]-3,5-dihydroxyheptanoate (0.49 g).

IR (Nujol) : 3380, 1580 cm$^{-1}$.

NMR (CD$_3$OD, δ) : 1.33 (3H, d, J=6Hz), 1.4-2.4 (8H, m), 2.7-3.2 (4H, m), 3.6-4.2 (2H, m), 4.70 (1H, m), 6.8-7.6 (7H, m).

EXAMPLE 5

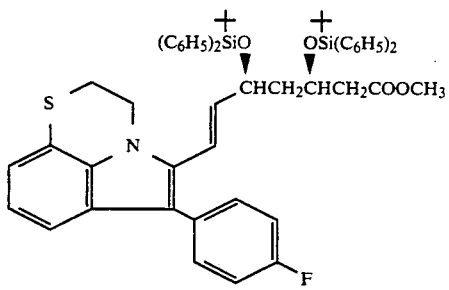

To a stirred solution of methyl (±)-erythro-(E)-7-[2,3-dihydro-6-[4-fluorophenyl)pyrrolo[1,2,3-de][1,4]-benzothiazin-5-yl]-3,5-dihydroxyhept-6-enoate (2.71 g) and imidazole (2.09 g) in N,N-dimethylformamide (30 ml) was added dropwise tert-butylchlorodiphenylsilane (3.71 g) at room temperature under nitrogen atomosphere. The mixture was stirred for 24 hours at the same temperature and then poured into water (70 ml). The mixture was extracted with ethyl acetate (60 ml) and the extract was washed with brine, dried and evaporated. The syrupy residue was chromatogrpahed on a column of silica gel (100 g) with hexane-ethyl acetate (20:1, V/V) eluent to give methyl (±)-erythro-(E)-3,5-bis(-tert-butyldiphenylsilyloxy)-7-[2,3-dihydro-6-(4-fluorophenyl)pyrrolo[1,2,3-de][1,4]-benzothiazin-5-yl]hept-6-enoate (5.05 g).

IR (Neat): 2950, 1735, 1530 cm$^{-1}$.

NMR (CDCl$_3$, δ) : 0.90 (9H, s), 0.96 (9H, s), 1.69-1.96 (2H, m), 2.40-2.68 (2H, m), 2.9-3.1 (2H, m), 3.57 (3H, s), 3.8-4.0 (2H, m), 4.2-4.5 (2H, m), 5.38 (1H, dd, J=6.5 and 16.4Hz), 6.07 (1H, d, J=16.4Hz), 7.0-7.8 (27H, m).

MASS m/z: 917.

EXAMPLE 6-1

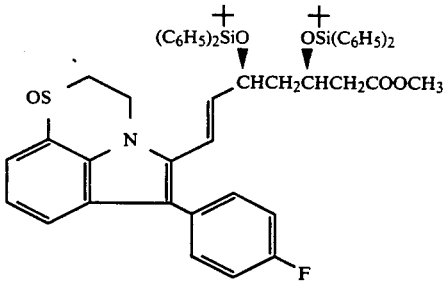

To a solution of methyl (±)-erythro-(E)-3,5-bis(tert-butyldiphenylsilyloxy)-7-[2,3-dihydro-6-[4-fluorophenyl)pyrrolo[ 1,2,3-de][1,4]benzothiazin-5-yl]hept-6-enoate (2.20 g) in dichloromethane (25 ml) was added m-chloroperbenzoic acid (80%, 0.57 g) below −20° C. The mixture was stirred for minutes at the same temperature. After addition of 5% aqueous sodium bisulfite (10 ml) and saturated aqueous sodium bicarbonate (25 ml), the mixture was extracted with dichloromethane (30 ml×3). The extracts were combined, dried and evaporated. The syrupy residue was chromatographed on a column of silica gel with toluene-ethyl acetate (4:1, V/V) eluent to give methyl (±)-erythro-(E)-3,5-bis(-tert-butyldiphenylsilyloxy)-7-[2,3-dihydro-6-(4-fluorophenyl)-1-oxopyrrolo[1,2,3-de][1,4]benzothiazin-5-yl]-hept-6-enoate (1.88 g).

IR (Neat) : 2950, 2860, 1735, 1535 cm$^{-1}$.

NMR (CDCl$_3$, δ) : 0.88 (9H, s), 0.98 (9H, s), 1.6-2.0 (2H, m), 2.4-2.8 (2H, m), 3.2-3.4 (2H, m), 3.56 and 3.60 (3H, each s), 3.8-4.5 (4H, m), 5.3-5.7 (1H, m), 6.08 (1H, d, J=16Hz), 7.0-7.8 (27H, m).

EXAMPLE 6-2

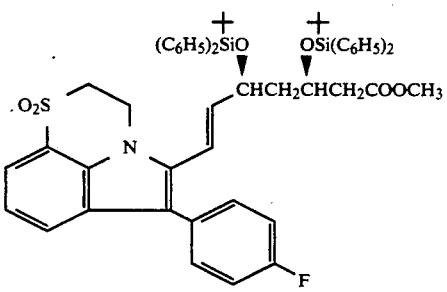

To a stirred solution of methyl (±)-erythro-(E)-3,5-bis(tert-butyldiphenylsilyloxy)-7-[2,3-dihydro-6-(4-fluorophenyl)pyrrolo[1,2,3-de][1,4]benzothiazin-5-yl]hept-6-enoate (2.30 g) in dichloromethane (20 ml) was added m-chloroperbenzoic acid (80%, 1.20 g) below 5° C. The mixture was stirred for 2 hours at 0° C. After addition of 5% aqueous sodium bisulfite (10 ml) and saturated aqueous sodium bicarbonate (25 ml), the mixture was extracted with dichloromethane (50 ml). The extract was washed with brine, dried and evaporated to give a syrupy residue, which was chromatographed on a column of silica gel (50 g) with toluene-ethyl acetate eluent to give methyl (±)-erythro-(E)-3,5-bis(tert-butyldiphenylsilyloxy)-7-[2,3-dihydro-6-(4-fluorophenyl)-1,1-dioxopyrrolo[1,2,3-de][1,4]-benzothiazin-5-yl]hept-6-enoate (1.29 g).

IR (Neat) : 3050, 2940, 2860, 1735, 1535, 1500 cm$^{-1}$

NMR (CDCl$_3$, δ) : 0.88 (9H, s), 0.97 (9H, s), 1.7-2.0 (2H, m), 2.4-2.8 (2H, m), 3.2-3.3 (2H, m), 3.59 (3H, s), 4.0-4.3 (3H, m), 4.4-4.5 (1H, m), 5.37 (1H, dd, J=6.2 and 16.4Hz), 6.05 (1H, d, J=16.4Hz), 7.0-7.8 (27H, m).

MASS m/z: 949.

EXAMPLE 7-1

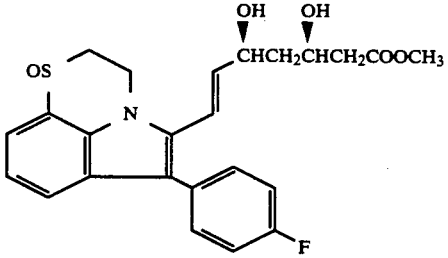

To an ice-cooled solution of 1N tetrabutylammonium fluoride in tetrahydrofuran (40 ml) was added dropwise acetic acid (2.4 ml), and then the mixture was added to an ice-cooled solution of methyl (±)-erythro-(E)-3,5-bis(tert-butyldiphenylsilyloxy)-7-[2,3-dihydro-6-(4- fluorophenyl)-1-oxopyrrolo[1,2,3-de][1,4]benzothiazin-5-yl]hept-6-enoate (1.99 g) in tetrahydrofuran (10 ml). The resultant mixture was stirred for 40 hours at room temperature and diluted with ethyl acetate (100 ml).

The solution was washed with brine 3 times, dried and evaporated to give a syrupy residue. The residue was chromatographed on a column of silica gel with ethyl acetate-methanol (40:1, V/V) eluent to give methyl (±)-erythro-(E)-7-[2,3-dihydro-6-(4-fluorophenyl)-1-oxopyrrolo[1,2,3-de][1,4]benzothiazin-5-yl]-3,5-dihydroxyhept-6-enoate (0.69 g).

IR (Neat): 3370, 3000, 2950, 1730, 1530, 1530, 1500 cm$^{-1}$.

NMR (CDCl$_3$, δ): 1.5–1.8 (2H, m), 2.50 (2H, d, J=5.9Hz), 2.8–3.0 (1H, m), 3.5–3.7 (1H, m), 3.72 (3H, s), 4.2–4.8 (4H, m), 6.04 (1H, dd, J=5.5 and 16Hz), 6.70 (1H, d, J=16Hz), 7.0–7.8 (7H, m).

EXAMPLE 7-2

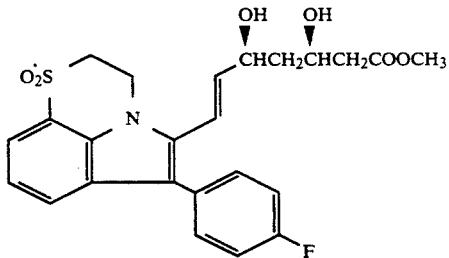

Methyl (±)-erythro-(E)-7-[2,3-dihydro-6-(4-fluorophenyl)-1,1-dioxopyrrolo[1,2,3-de][1,4]benzothiazin-5-yl]-3,5-dihydroxyhept-6-enoate (0.44 g) was obtained in substantially the same manner as that of Example 7-1).

IR (Neat) : 3450, 1730, 1535, 1500 cm$^{-1}$.

NMR (CDCl$_3$, δ) : 1.6–1.8 (2H, m), 2.51 (2H, d, J=6.2Hz), 3.5–3.7 (2H, m), 3.73 (3H, s), 3.76 (1H, s), 3.82 (1H, s), 4.2–4.7 (2H, m), 4.8–4.9 (2H, m), 5.90 (1H, dd, J=5.3 and 16.2Hz), 6.70 (1H, d, J=16.2Hz), 7.1–7.8 (7H, m).

EXAMPLE 8

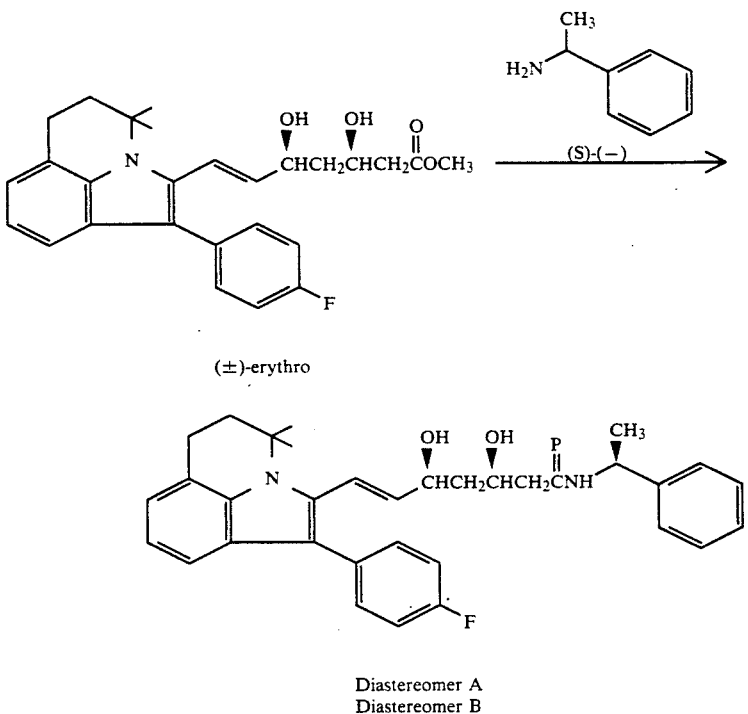

(±)-erythro

Diastereomer A
Diastereomer B

A mixture of methyl (±)-erythro-(E)-7-[5,6-dihydro-4,4-dimethyl-1-(4-fluorophenyl)-4H-pyrrolo[3,2,1-ij]quinolin-2-yl]-3,5-dihydroxyhept-6-enoate (1.0 g) and (S)-(−)-1-phenylethylamine (1.34 g) was stirred at 90° C. for 6 hours and then cooled to room temperature. The reaction mixture was diluted with ethyl acetate and poured into diluted hydrochloric acid. The mixture was extracted with ethyl acetate and the extract was washed in turn with saturated aqueous sodium bicarbonate and brine. The organic layer was dried and evaporated to give a diastereomeric mixture of N-(S)-(1-phenylethyl)-erythro-(E)-7-[5,6-dihydro-4,4-dimethyl-1-(4-fluorophenyl)-4H-pyrrolo[3,2,1-ij]quinolin-2-yl]-3,5-dihydroxyhept-6-enamide (1.27 g). The diastereomeric mixture was separated by using medium pressure chromatography on a column of silica gel. Elution with a mixture of hexane and ethyl acetate (2:3, V/V) gave diastereomer A (0.43 g) of N-(S)-(1-phenylethyl)-erythro-(E)-7-[5,6-dihydro-4,4-dimethyl-1-(4-fluorophenyl)-4H-pyrrolo[3,2,1-ij]quinolin-2-yl]-3,5-dihydroxyhept-6-enamide as a syrup.

[α]$_D^{25}$−15.6° (C 1.0, CHCl$_3$).

IR (film) : 3320, 2990, 2950, 1640, 1535, 1500 cm$^{-1}$.

NMR (CDCl$_3$, δ) : 1.38–1.57 (2H, m), 1.49 (3H, d, J=7.0Hz), 1.62 (6H, s), 2.09 (2H, t, J=6.2Hz), 2.20–2.40 (2H, m), 3.00 (2H, t, J=6.2Hz), 4.13 (1H, m), 4.45 (1H, m), 5.11 (1H, m), 5.54 (1H, dd, J=5.3 and 15.8Hz), 6.09 (1H, bd, J=7.9Hz), 6.83 (1H, dd, J=1.5 and 15.8Hz), 6.90–7.40 (12H, m).

Elution with a mixture of hexane and ethyl acetate (1:2, V/V) was continued to provide diastereomer B (0.49 g) thereof as a syrup, which was crystallized from a mixture of hexane and ethyl acetate to give colorless needles (0.34 g).

[α]$_D^{26}$−36.3° (C 1.0, CHCl$_3$).

mp : 133°–135° C.

IR (Nujol) : 3420, 3200, 1650, 1530, 1500 cm$^{-1}$.

NMR (CDCl$_3$, δ) : 1.25–1.54 (2H, m), 1.49 (3H, d, J=7.0Hz), 1.62 (6H, s), 2.09 (2H, t, J=6.2Hz), 2.20–2.40 (2H, m), 3.00 (2H, t, J=6.2Hz), 4.13 (1H, m), 4.44 (1H, m), 5.11 (1H, m), 5.53 (1H, dd, J=5.3 and 15.8Hz), 6.06 (1H, bd, J=7.8Hz), 6.82 (1H, dd, J=1.3 and 15.8Hz), 6.87–7.41 (12H, m).

EXAMPLE 9-1

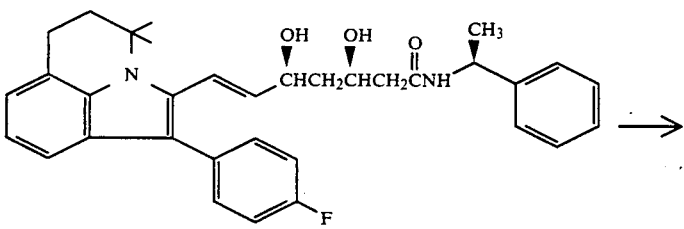

Diastereomer A

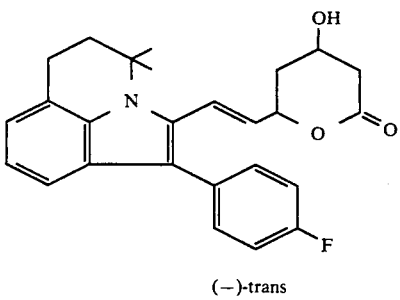

(−)-trans

Diastereomer A (0.37 g) of N-(S)-(1-phenylethyl)-erythro-(E)-7-[5,6-dihydro-4,4-dimethyl-1-(4-fluorophenyl)-4H-pyrrolo[3,2,1-ij]quinolin-2-yl]-3,5-dihydroxyhept-6-enamide was dissolved in ethanol (4 ml) containing 1N sodium hydroxide (3.4 ml) and the solution was refluxed for 15 hours. The solvent was removed in vacuo to give a residue which was mixed with water (10 ml) and acidified with 1N hydrochloric acid (4.4 ml). The resulting mixture was extracted with ethyl acetate. The extract was washed with brine twice, dried and evaporated to give diastereomer A acid of erythro-(E)-7-[5,6-dihydro-4,4-dimethyl-1-(4-fluorophenyl)-4H-pyrrolo[3,2,1-ij]quinolin-2-yl]-3,5-dihydroxyhept-6-enoic acid as a yellow syrup. To a cooled solution of the syrup in tetrahydrofuran (2 ml) were added 1-hydroxybenzotriazole (0.046 g) and N-(3-dimethylaminopropyl)-N'-ethylcarbodiimide (0.11 g) and the solution was allowed to stand overnight at room temperature. The reaction mixture was diluted with ethyl acetate and the resulting suspension was washed in turn with saturated aqueous sodium bicarbonate and brine. The organic layer was dried and evaporated to give a syrup (0.33 g). Crystallization of the syrup from a mixture of ethyl acetate and isopropyl ether gave (−)-(E)-6-[2-{5,6-dihydro-4,4-dimethyl-1-(4-fluorophenyl)-4H-pyrrolo[3,2,1-ij]quinolin-2-yl}ethenyl]-4-hydroxy-3,4,5,6-tetrahydro-2H-pyran-2-one (trans isomer) (0.19 g).

[α]$_D^{24}$ −6.1° (C 1.0, acetone).

mp: 171°–173° C. (dec.).

IR (Nujol) : 3500, 1735, 1535, 1500 cm$^{-1}$.

NMR (Acetone-d$_6$, δ) : 1.66 (6H, s), 1.70–2.00 (2H, m), 2.12 (2H, t, J=6.9Hz), 2.45–2.76 (2H, m), 3.00 (2H, t, J=6.9Hz), 4.31 (1H, m), 4.42 (1H, d, J=3.1Hz), 5.30 (1H, m), 5.65 (1H, dd, J=6.4 and 15.8Hz), 6.90–7.51 (8H, m).

EXAMPLE 9-2

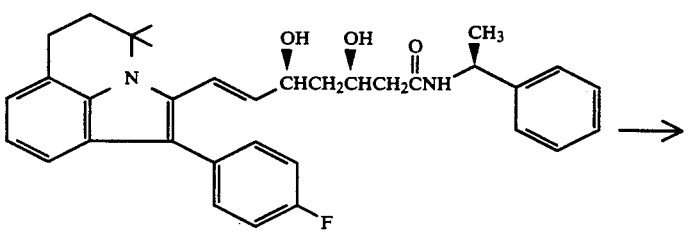

Diastereomer B

-continued

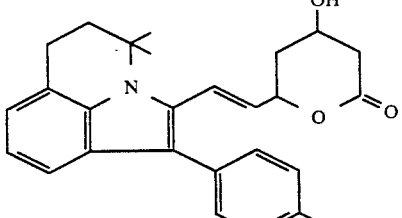

(+)-trans

Diastereomer B (0.28 g) of N-(S)-(1-phenylethyl)-erythro-(E)-7-[5,6-dihydro-4,4-dimethyl-1-(4-fluorophenyl)-4H-pyrrolo[3,2,1-ij]quinolin-2-yl]-3,5-dihydroxyhept-6-enamide was hydrolyzed and the resulting diastereomer B acid was lactonized in substantially the same manner as Example 9-1) to give (+)-(E)-6-[2-{5,6-dihydro-4,4-dimethyl-1-(4-fluorophenyl)-4H-pyrrolo[3,2,1-ij]quinolin-2-yl}ethenyl]-4-hydroxy-3,4,5,6-tetrahydro-2H-pyran-2-one (trans isomer) (0.18 g) as crystals.

$[\alpha]_D^{26}$ +6.2° (C 1.0, acetone).
mp: 170°–172° C. (dec.),
IR (Nujol) : 3500, 1735, 1535, 1500 cm$^{-1}$.
NMR (Acetone-d6, δ) : 1.66 (6H, s), 1.70–2.00 2H, m), 2.12 (2H, t, J=6.9Hz), 2.45–2.76 (2H, m), 3.00 (2H, t, J=6.9Hz), 4.31 (1H, m), 4.42 (1H, d, J=3.1Hz), 5.30 (1H, m), 5.65 (1H, dd, J=6.4 and 15.8Hz), 6.90–7.51 (8H, m).

EXAMPLE 10-1

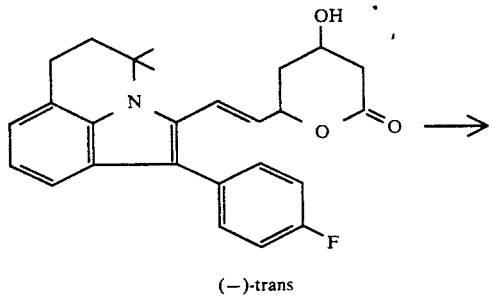

(−)-trans

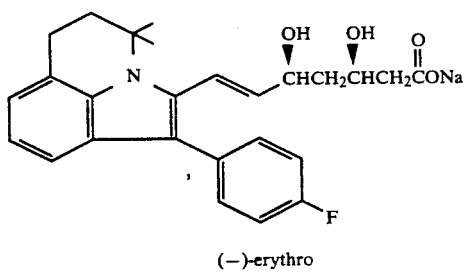

(−)-erythro

To an ice cooled suspension of (−)-(E)-6-[2-{5,6-dihydro-4,4-dimethyl-1-(4-fluorophenyl)-4H-pyrrolo[3,2,1-ij]quinolin-2-yl}ethenyl]-4-hydroxy-3,4,5,6-tetrahydro-2H-pyran-2-one (trans isomer) (0.12 g) in methanol was added dropwise 1N sodium hydroxide (0.29 ml). The mixture was stirred for 1 hour at room temperature. The solvent was removed in vacuo, and the residue was dissolved in water (7 ml) and freeze-dried to give sodium (−)-erythro-(E)-7-[5,6-dihydro-4,4-dimethyl-1-(4-fluorophenyl)-4H-pyrrolo[3,2,1-ij]quinolin-2-yl]-3,5-dihydroxyhept-6-enoate (0.13 g) as yellowish powder.

$[\alpha]_D^{29}$ −27.4° (C 0.5, methanol).
NMR (CD$_3$OD, δ) : 1.36–1.71 (2H, m), 1.64 (6H, s), 2.09 (2H, t, J=6.2Hz), 2.16–2.38 (2H, m), 2.98 (2H, t, J=6.2Hz), 3.91 (1H, m), 4.35 (1H, m), 5.57 (1H, dd, J=6.1 and 15.9Hz), 6.81–7.42 (8H, m).

EXAMPLE 10-2

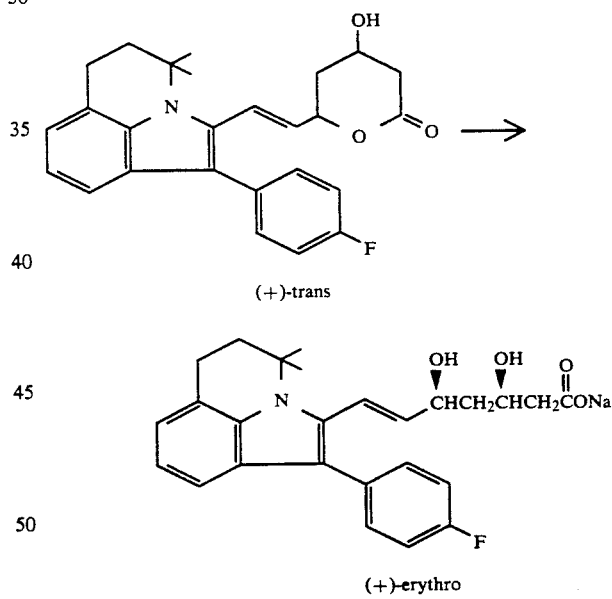

(+)-(E)-6-[2-{5,6-Dihydro-4,4-dimethyl-1-(4-fluorophenyl)-4H-pyrrolo[3,2,1-ij]quinolin-2-yl}ethenyl]-4-hydroxy-3,4,5,6-tetrahydro-2H-pyran-2-one (trans isomer) (0.09 g) was hydrolyzed in substantially the same manner as that of Example 10-1) to give sodium (+)-erythro-(E)-7-[5,6-dihydro-4,4-dimethyl-1-(4-fluorophenyl)-4H-pyrrolo[3,2,1-ij]quinolin-2-yl]-3,5-dihydroxyhept-6-enoate (0.10 g) as yellowish powder.

$[\alpha]_D^{29}$ +27.6° (C 0.5, methanol).
NMR (CD$_3$OD, δ): 1.36–1.71 (2H, m), 1.64 (6H, s), 2.09 (2H, t, J=6.2Hz), 2.16–2.38 (2H, m), 2.98 (2H, t, J=6.2Hz), 3.91 (1H, m), 4.35 (1H, m), 5.57 (1H, dd, J=6.1 and 15.9Hz), 6.81–7.42 (8H, m).

EXAMPLE 11

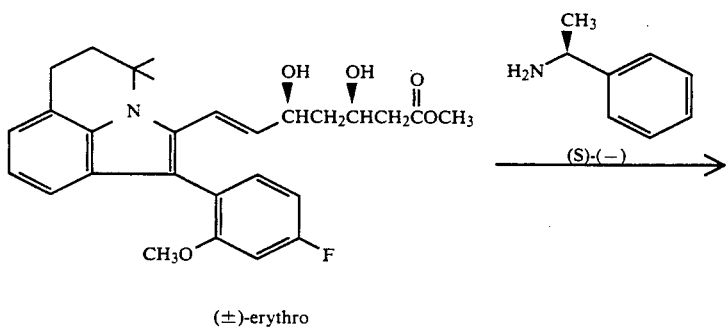

(±)-erythro

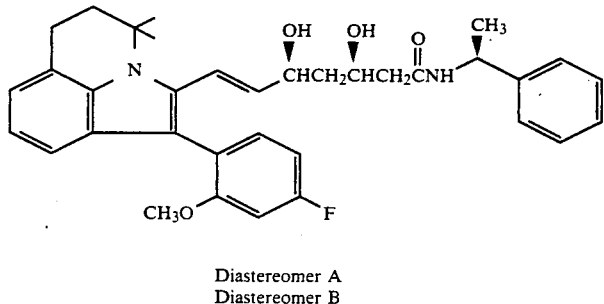

Diastereomer A
Diastereomer B

Condensation of (±)-erythro-(E)-7-[5,6-dihydro-4,4-dimethyl-1-(4-fluoro-2-methoxyphenyl)-4H-pyrrolo[3,2,1-ij]-quinolin-2-yl]-3,5-dihydroxyhept-6-enoate (2.0 g) and (S)-(−)-1-phenylethylamine (2.5 g), and separation of the resulting diastereomeric amides were carried out in substantially the same manner as that of Example 8 to give diastereomer A (0.71 g) of N-(S)-(1-phenylethyl)erythro-(E)-7-[5,6-dihydro-4,4-dimethyl-1-(4-fluoro-2-methoxyphenyl)-4H-pyrrolo[3,2,1-ij]quinolin-2-yl]-3,5-dihydroxyhept-6-enamide as a syrup.

$[\alpha]_D^{26}$ −24.8° (C 1.0, CHCl$_3$).

IR (film) : 3320, 2990, 2950, 1640, 1600, 1535 cm$^{-1}$.

NMR (CDCl$_3$, δ) : 1.30–1.60 (2H m). 1.50 (3H d J=6.9Hz), 1.64 (6H, s), 2.10 (2H, t, J=5.9Hz), 2.20–2.40 (2H, m), 2.99 (2H, t, J=5.9Hz), 3.71 (3H, s), 4.10 (1H, m), 4.41 (1H, m), 5.12 (1H, m), 5.48 (1H, dd, J=5.8 and 15.7Hz), 6.11 (1H, bd, J=7.6Hz), 6.60–7.40 (12H, m).

Diastereomer B (0.68 g) of N-(S)-1-phenylethyl)erythro-(E)-7-[5,6-dihydro-4,4-dimethyl-1-(4-fluoro-2-methoxyphenyl)- 4H-pyrrolo[3,2,1-ij]quinolin-2-yl]-3,5-dihydroxyhept-6-enamide was obtained as a syrup, in substantially the same manner as that of Example 8.

$[\alpha]_D^{26}$ −23.9° (C 1.0, CHCl$_3$).

IR (film) : 3320, 2990, 2950, 1645, 1605, 1540 cm$^{-1}$.

NMR (CDCl$_3$, δ) : 1.30–1.60 (2H, m), 1.50 (3H, d, J=6.9Hz), 1.63 (6H, s), 2.09 (2H, t, J=6.2Hz), 2.20–2.40 (2H, m), 2.99 (2H, t, J=6.2Hz), 3.71 (3H, s), 4.10 (1H, m), 4.40 (1H, m), 5.11 (1H, m), 5.46 (1H, dd, J=5.7 and 15.7Hz), 6.09 (1H, d, J=7.8Hz), 6.50–7.40 (12H, m).

EXAMPLE 12-1

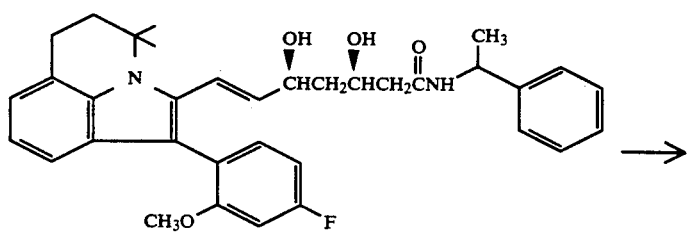

Diastereomer A

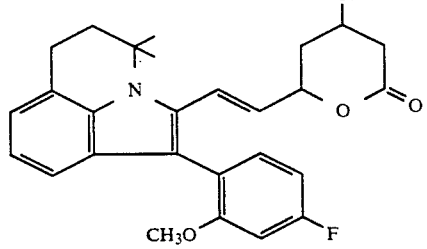

(−)-trans

Diastereomer A (0.50 g) of N-(S)-(1-phenylethyl)-erythro-(E)-7-[5,6-dihydro-4,4-dimethyl-1-(4-fluoro-2-methoxyphenyl)-4H-pyrrolo[3,2,1-ij]quinolin-2-yl]-3,5-dihydroxyhept-6-enamide was hydrolyzed and the resulting diastereomer A acid was lactonized in substantially the same manner as that of Example 9-1) to give (−)-(E)-6-[2-{5,6-dihydro-4,4-dimethyl-1-(4-fluoro-2-methoxyphenyl)-4H-pyrrolo[3,2,1-ij]quinolin-2-yl}ethenyl]-4-hydroxy-3,4,5,6-tetrahydro-2H-pyran-2-one (trans isomer) (0.24 g) as crystals.

$[\alpha]_D^{24} -12.2°$ (C 1.0, acetone).

mp: 144°-146° C. (dec.).

IR (Nujol) : 3450, 1720, 1605, 1540, 1500 cm$^{-1}$.

NMR (Acetone-d$_6$, δ) : 1.57-1.90 (2H, m), 1.65 (6H, s), 2.12 (2H, t, J=6.4Hz), 2.41-2.72 (2H, m), 2.99 (2H, t, J=6.4Hz), 3.76 (3H, s), 4.24 (1H, m), 4.37 (1H, d, J=3.2Hz), 5.22 (1H, m), 5.54 (1H, dd, J=6.6 and 15.7Hz), 6.71-7.30 (7H, m).

EXAMPLE 12-2

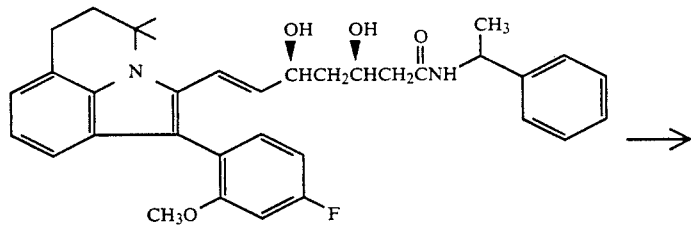

Diastereomer B

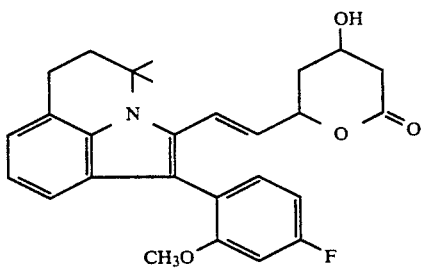

(+)-trans

Hydrolysis of diastereomer B (0.50 g) of N-(S)-(1-phenylethyl)-erythro-(E)-7-[5,6-dihydro-4,4-dimethyl-1-(4-fluoro-2-methoxyphenyl)-4H-pyrrolo[3,2,1-ij]quinolin-2-yl]-3,5-dihydroxyhept-6-enamide and lactonization of the resulting acid according to the method described in Example 9-1) gave (+)-(E)-6-[2-{5,6-dihydro-4,4-dimethyl-1-(4-fluoro-2-methoxyphenyl)-4H-pyrrolo[3,2,1-ij]quinolin-2-yl}ethenyl]-4-hydroxy-3,4,5,6-tetrahydro-2H-pyran-2-one (trans isomer) (0.25 g) as crystals.

$[\alpha]_D^{24} +14.3°$ (C 1.0, acetone).

mp: 152°-153.5° C. (dec.)

IR (Nujol) : 3450, 1720, 1605, 1540, 1500 cm$^{-1}$.

NMR (Acetone-d$_6$, δ) : 1.57-1.90 (2H, m), 1.65 (6H, s), 2.12 (2H, t, J=6.4Hz), 2.41-2.72 (2H, m), 2.99 (2H, t, J=6.4Hz), 3.76 (3H, s), 4.24 (1H, m), 4.37 (1H, d, J=3.2Hz), 5.22 (1H, m), 5.54 (1H, dd, J=6.6 and 15.7Hz), 6.71-7.30 (7H, m)

EXAMPLE 13-1

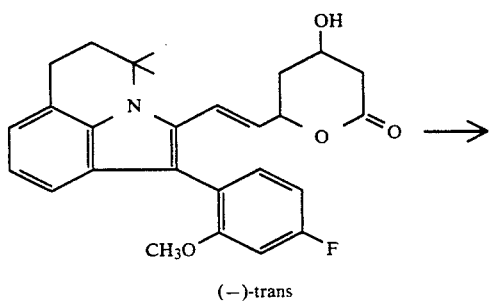

(−)-trans

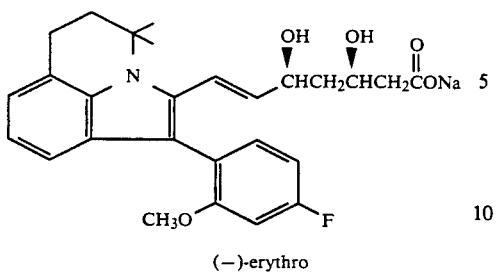

(−)-erythro

Hydrolysis of (−)-(E)-6-[2-{5,6-dihydro-4,4-dimethyl-1-(4-fluoro-2-methoxyphenyl)-4H-pyrrolo[3,2,1-ij]quinolin-2-yl }ethenyl]-4-hydroxy-3,4,5,6-tetrahydro-2H-pyran-2-one (trans isomer) (0.15 g) according to the method described in Example 10-1) gave sodium (−)-erythro-(E)-7-[5,6-dihydro-4,4-dimethyl-1-(4-fluoro-2-methoxyphenyl)-4H-pyrrolo-[3,2,1-ij]quinolin-2-yl]-3,5-dihydroxyhept-6-enoate (0.16 g) as yellowish powder.

$[\alpha]_D^{24} -43.6°$ (C 1.0, methanol).

NMR (CD$_3$OD, δ) : 1.14–1.58 (2H, m), 1.65 (6H, s), 2.09 (2H, t, J=6.4Hz), 2.11–2.34 (2H, m), 2.98 (2H, t, J=6.4Hz), 3.72 (3H, s), 3.79 (1H, m), 4.31 (1H, m), 5.49 (1H, dd, J=6.3 and 15.7Hz), 6.65–7.20 (7H, m).

EXAMPLE 13-2

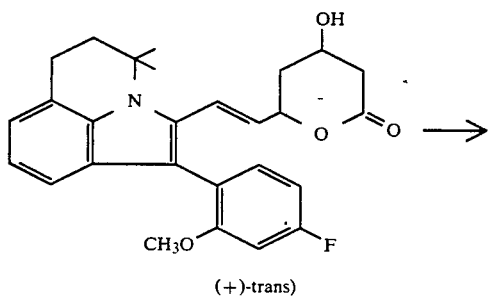

(+)-trans

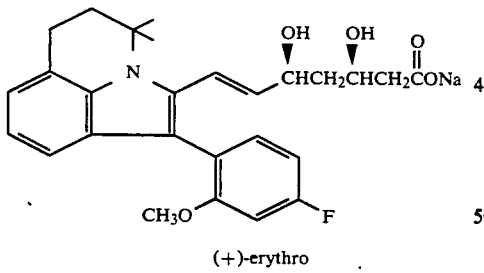

(+)-erythro

Hydrolysis of (+)-(E)-6-[2-{5,6-dihydro-4,4-dimethyl-1-(4-fluoro-2-methoxyphenyl)-4H-pyrrolo[3,2,1-ij]quinolin-2-yl}ethenyl]-4-hydroxy-3,4,5,6-tetrahydro-2H-pyran-2-one (trans isomer) (0.15 g) according to the method described in Example 10-1) gave sodium (+)-erythro-(E)-7-[5,6-dihydro-4,4-dimethyl-1-(4-fluoro-2-methoxyphenyl)-4H-pyrrolo[3,2,1-ij]quinolin-2-yl]-3,5-dihydroxyhept-6-enoate (0.16 g).

$[\alpha]_D^{24} +43.5°$ (C 1.0, methanol).

NMR (CD$_3$OD, δ) : 1.14–1.58 (2H, m), 1.65 (6H, s), 2.09 (2H, t, J=6.4Hz), 2.11–2.34 (2H, m), 2.98 (2H, t, J=6.4Hz), 3.72 (3H, s), 3.79 (1H, m), 4.31 (1H, m), 5.49 (1H, dd, J=6.3 and 15.7Hz), 6.65–7.20 (7H, m).

What is claimed is:

1. A compound of the formula:

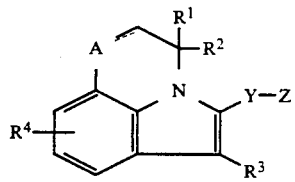

in which

R$^1$ and R$^2$ are each hydrogen or lower alkyl,

R$^3$ is aryl or unsaturated, 5 or 6-membered heterocyclic group containing a sulfur atom, each of which may be substituted by one or more substituent(s) selected from the group consisting of halogen, hydroxy, lower alkyl, aryloxy, trihalo(lower)alkyl, lower alkoxy and mono- or di(lower)alkylamino, R$^4$ is hydrogen, halogen or lower alkyl, A is methylene, methine, oxa, thia, sulfinyl or sulfonyl, Y is vinylene or ethylene, Z is a group of the formula:

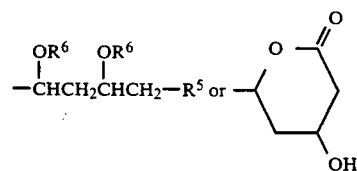

wherein

R$^5$ is carboxy or protected carboxy, and

R$^6$ is hydrogen or hydroxy-protective group, and the line of ▬ is a single or double bond, or a pharmaceutically acceptable salt thereof.

2. The compound of claim 1, wherein R$^3$ is phenyl, tolyl, xylyl, cumenyl, mesithyl, naphthyl or thienyl, each of which is substituted by one or more substituent(s) selected from a group consisting of halogen, hydroxy, lower alkyl, aryloxy, trihalo(lower)alkyl, lower alkoxy and mono- or di(lower) alkylamino, R$^5$ is carboxy, esterified carboxy or amidated carboxy, and R$^6$ is hydrogen, trisubstituted silyl or acyl derived from carboxylic, carbonic, sulfonic or carbamic acids.

3. The compound of claim 2, wherein

R$^3$ is phenyl, tolyl, xylyl, cumenyl, mesithyl, naphthyl or thienyl, each of which may be substituted by one to three substituent(s) selected from a group consisting of halogen, hydroxy, lower alkyl, phenoxy, tolyloxy, xylyloxy, cumenyloxy, mesithyloxy, naphthyloxy, trihalo(lower)alkyl, lower alkoxy and mono- or di(lower)alkylamino, R$^5$ is carboxy, lower alkoxycarbonyl or N-[ar(lower)alkyl]carboxamide, in which aryl is phenyl, tolyl, xylyl, cumenyl, mesithyl or naphthyl, and R$^6$ is hydrogen, a silyl group trisubstituted by a group consisting of lower alkyl, aryl and ar(lower)alkyl, carbamoyl, aliphatic acyl, aromatic acyl, or aliphatic acyl substituted with aromatic group(s) or thienyl derived from carboxylic, carbonic, sulfonic and carbamic acids, in which aryl is phenyl, tolyl, xylyl, cumenyl, mesithyl or naphthyl.

4. The compound of claim 3, wherein $R^3$ is phenyl, naphthyl or thienyl, each of which may be substituted by one to three substituent(s) selected from a group consisting of halogen, hydroxy, lower alkyl, phenoxy, trihalo(lower)alkyl, lower alkoxy and mono- or di(lower)alkylamino, $R^5$ is carboxy, lower alkoxycarbonyl or N-[phenyl(lower)alkyl]carboxamide, and $R^6$ is hydrogen or (lower alkyl)diphenylsilyl.

5. The compound of claim 4, wherein
$R^1$ and $R^2$ are each hydrogen or $C_1$-$C_4$ alkyl,
$R^3$ is phenyl, naphthyl or thienyl, each of which is substituted by one to three substituent(s) selected from a group consisting of halogen, hydroxy, $C_1$-$C_4$ alkyl, phenoxy, trihalo($C_1$-$C_4$)alkyl, $C_1$-$C_4$ alkoxy and mono- or di($C_1$-$C_4$)alkylamino,
$R^4$ is hydrogen, halogen or $C_1$-$C_4$ alkyl,
$R^5$ is carboxy, $C_1$-$C_4$ alkoxycarbonyl or N-[phenyl($C_1$-$C_4$)alkyl]carboxamide, and
$R^6$ is hydrogen or ($C_1$-$C_4$ alkyl)diphenylsilyl.

6. The compound of claim 5, wherein
Y is vinylene.

7. The compound of claim 6, wherein
A is methylene or methine.

8. The compound of claim 7, wherein
$R^3$ is phenyl, mono- or di- or trihalophenyl, mono- or di($C_1$-$C_4$)alkylphenyl, [mono- or di($C_1$-$C_4$)alkyl](halo)phenyl, phenoxyphenyl, naphthyl, trihalo($C_1$-$C_4$)alkylphenyl, [di($C_1$-$C_4$)alkylamino]phenyl, [mono- or di($C_1$-$C_4$)alkyl](hydroxy)phenyl, [($C_1$-$C_4$)alkoxy](halo)phenyl, thienyl, $C_1$-$C_4$ alkylthienyl or halothienyl,
A is methylene, and the line of ⸺ is a single bond.

9. The compound of claim 8, wherein
$R^5$ is carboxy, and
$R^6$ is hydrogen.

10. The compound of claim 9, wherein
$R^1$ and $R^2$ are each hydrogen or methyl,
$R^3$ is phenyl, 2-(or 3- or 4-)fluorophenyl, 2,4-(or 3,4-)difluorophenyl, 4-chlorophenyl, 3,4-dichlorophenyl, 2-chloro-4-fluorophenyl, 2,4,6-trifluorophenyl, m-tolyl, 2,4-(or 3,4- or 3,5-)xylyl, 4-fluoro-2-(or 3-)methylphenyl, 4-fluoro-3,5-dimethylphenyl, 4-phenoxyphenyl, 2-naphthyl, 3-trifluoromethylphenyl, 4-dimethylaminophenyl, 3,5-di-t-butyl-4-hydroxyphenyl, 2-methoxy-4-fluorophenyl, 5-methyl-2-thienyl or 5-chloro-2-thienyl,
$R^4$ is hydrogen, chlorine, fluorine or methyl.

11. The compound of claim 10, which is
(±)-erythro-(E)-7-[5,6-dihydro-4,4-dimethyl-1-(4-fluorophenyl)-4H-pyrrolo[3,2,1-ij]quinolin-2-yl]-3,5-dihydroxyhept-6-enoic acid, (±)-erythro-(E)-7-[5,6-dihydro-4,4-dimethyl-1-(4-fluoro-2-methoxyphenyl)-4H-pyrrolo[3,2,1-ij]quinolin-2-yl]-3,5-dihydroxyhept-6-enoic acid, (+)-erythro-(E)-7-[5,6-dihydro-4,4-dimethyl-1-(4-fluorophenyl)-4H-pyrrolo[3,2,1-ij]quinolin-2-yl]-3,5-dihydroxyhept-6-enoic acid, or (+)-erythro-(E)-7-[5,6-dihydro-4,4-dimethyl-1-(4-fluoro-2-methoxyphenyl)-4H-pyrrolo[3,2,1-ij]quinolin-2-yl]-3,5-dihydroxyhept-6-enoic acid, or sodium salts thereof.

12. A 3-hydroxy-3-methylglutaryl-coenzyme A reductase inhibitor pharmaceutical composition comprising, as an active ingredient, an effective amount of a compound of claim 1 or a pharmaceutically acceptable salt thereof in admixture with a pharmaceutically acceptable carrier or excipient.

13. A method for the treatment of hypercholesterolemic and hyperlipoproteinemic states and associated conditions which comprises administering an effective amount of a compound of claim 1 or a pharmaceutically acceptable salt thereof to a human being or animal.

14. A method for inhibiting 3-hydroxy-3-methylglutaryl-coenzyme A reductase which comprises administering an effective amount of a compound of claim 1 or a pharmaceutically acceptable salt thereof to a human being or animal.

* * * * *